(12) United States Patent
Bossenmaier et al.

(10) Patent No.: US 10,808,038 B2
(45) Date of Patent: Oct. 20, 2020

(54) HER3/HER2 BISPECIFIC ANTIBODIES BINDING TO THE BETA-HAIRPIN OF HER3 AND DOMAIN II OF HER2

(71) Applicant: Hoffmann-La Roche Inc., Little Falls, NJ (US)

(72) Inventors: Birgit Bossenmaier, Seefeld (DE); Richard Buick, Belfast (GB); Stefan Dengl, Munich (DE); Michael Gerg, Munich (DE); Carmen Peess, Tutzing (DE); Wolfgang Schaefer, Mannheim (DE); Michael Schraeml, Penzberg (DE); Claudio Sustmann, Munich (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/348,588

(22) Filed: Nov. 10, 2016

(65) Prior Publication Data

US 2017/0233490 A1    Aug. 17, 2017

Related U.S. Application Data

(63) Continuation of application No. PCT/EP2015/060488, filed on May 12, 2015.

(30) Foreign Application Priority Data

May 14, 2014 (EP) ..................... 14168323

(51) Int. Cl.
| | | |
|---|---|---|
| A61K 39/00 | (2006.01) | |
| C07K 16/32 | (2006.01) | |
| A61K 47/68 | (2017.01) | |
| C07K 16/46 | (2006.01) | |
| A61K 39/395 | (2006.01) | |

(52) U.S. Cl.
CPC .......... *C07K 16/32* (2013.01); *A61K 47/6829* (2017.08); *A61K 47/6879* (2017.08); *C07K 16/468* (2013.01); *A61K 39/39558* (2013.01); *A61K 2039/505* (2013.01); *A61K 2039/6068* (2013.01); *C07K 2317/24* (2013.01); *C07K 2317/31* (2013.01); *C07K 2317/33* (2013.01); *C07K 2317/34* (2013.01); *C07K 2317/35* (2013.01); *C07K 2317/73* (2013.01); *C07K 2317/76* (2013.01); *C07K 2317/77* (2013.01); *C07K 2317/92* (2013.01); *C07K 2317/94* (2013.01)

(58) Field of Classification Search
CPC .................. A61K 2039/505; A61K 39/39558
See application file for complete search history.

(56) References Cited

U.S. PATENT DOCUMENTS

| | | | |
|---|---|---|---|
| 8,597,652 B2 | 12/2013 | Fuh et al. | |
| 9,180,185 B2 | 11/2015 | Bauss et al. | |
| 9,611,331 B2 | 4/2017 | Bossenmaier et al. | |
| 9,725,511 B2 | 8/2017 | Bossenmaier et al. | |
| 9,725,512 B2 | 8/2017 | Bossenmaier et al. | |
| 9,783,611 B2 | 10/2017 | Bossenmaier et al. | |
| 9,840,565 B2 | 12/2017 | Bossenmaier et al. | |
| 2016/0002313 A1* | 1/2016 | Kaumaya ............. | C07K 14/721 424/489 |
| 2017/0233490 A1 | 8/2017 | Bossenmaier et al. | |

FOREIGN PATENT DOCUMENTS

| | | |
|---|---|---|
| EP | 2 727 942 A1 | 5/2014 |
| WO | 2003/000877 | 1/2003 |
| WO | 2007/0841181 A2 | 7/2007 |
| WO | 2009/074318 | 6/2009 |
| WO | 2010/059315 A1 | 5/2010 |
| WO | 11/056124 | 5/2011 |
| WO | 2012/022814 | 2/2012 |
| WO | 2012/125864 A2 | 9/2012 |
| WO | 2012/150320 | 11/2012 |
| WO | 2012/150321 | 11/2012 |
| WO | 2013/084148 A2 | 6/2013 |
| WO | WO2013134881 A1 * | 9/2013 |
| WO | 2014/067642 A1 | 5/2014 |
| WO | WO2014131019 A2 * | 8/2014 |
| WO | 2015/173248 | 11/2015 |

OTHER PUBLICATIONS

Alajati et al. (Cancer Res. Sep. 1, 2013; 73 (17): 5320-7).*
Omenn et al. (J. Proteomics. Jul. 31, 2014; 107: 103-12; pp. 1-22).*
George et al. (Circulation. 1998; 97: 900-906).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Beeram, M. et al., "MM-111—A novel bispecific antibody targeting HER-2/HER-3 heterodimer: Safety and tolerability in a first-inhuman Phase I/II study in patients with refractory HER-2-positive (HER-2+) cancers" Poster pp. 1 ( Dec. 10, 2012).

(Continued)

*Primary Examiner* — Stephen L Rawlings
(74) *Attorney, Agent, or Firm* — Genentech, Inc.

(57) ABSTRACT

The invention relates to HER3/HER2 bispecific antibodies binding to the beta-hairpin of HER3 and domain II of HER2, their preparation and use as medicament.

6 Claims, 25 Drawing Sheets

Specification includes a Sequence Listing.

(56) References Cited

OTHER PUBLICATIONS

Huhalov, A. et al., "MM-111, an ErbB2/ErbB3 bispecific antibody with potent activity in ErbB2-overexpressing cells, positively combines with trastuzumab to inhibit growth of breast cancer cells driven by ErbB2/ErbB3 oncogenic unit" Abstract AACR 101st Annual Meeting, pp. 845-846 (Apr. 20, 2010).
International Preliminary Report on Patentability—PCT/EP2015/060488 (dated Nov. 15, 2016).
Kang, J.C. et al., "Engineering multivalent antibodies to target heregulin-induced HER3 signaling in breast cancer cells" mAbs 6(2):340-353 (2014).
Robinson et al., "Targeting ErbB2 and ErbB3 with a bispecific single-chain Fv enhances.targeting selectivity and induces a therapeutic effect in vitro" Brit J Cancer 99:1415-1425 (2008).
Cho et al., "Structure of the Extracellular Region of HER3 Reveals an Interdomain Tether" Science 297:1330-1333 (Aug. 23, 2002).

* cited by examiner

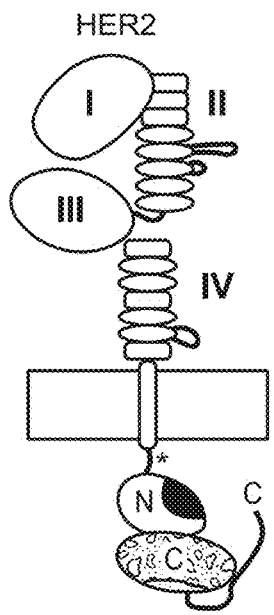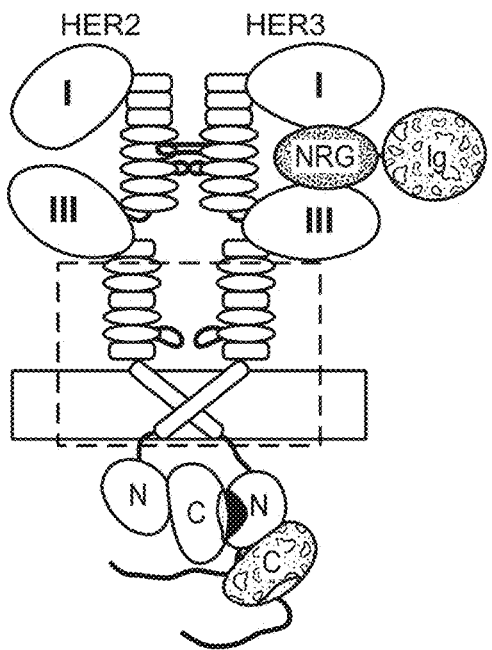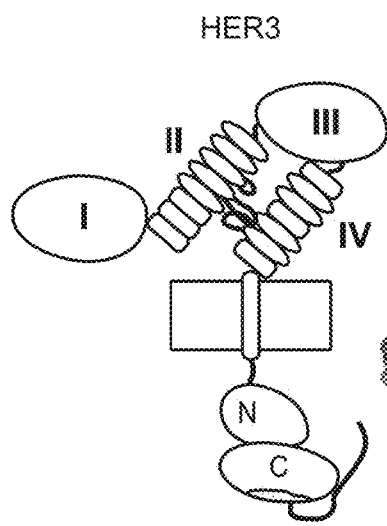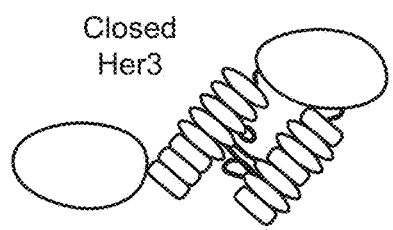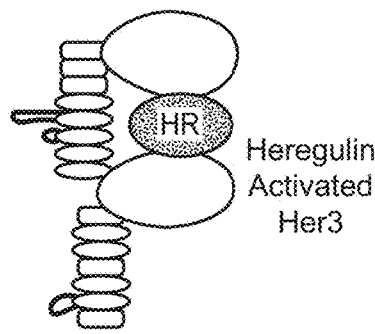
FIG. 1A — Constitutively Active
FIG. 1B — Activated Conformation Beta Hairpin Heterodimerization
FIG. 1C — Closed/Locked Conformation Beta Hairpin is Covered
FIG. 1D — Closed Her3
FIG. 1E — Heregulin Activated Her3

FIG. 13
M-074 HER3:  PQPLV<u>YNK</u>L<u>TF</u>Q<u>LE</u>PNPHTK
M-011 HER3:  PQ<u>PLVYNK</u>L<u>TF</u>Q<u>LE</u>PNPHTK
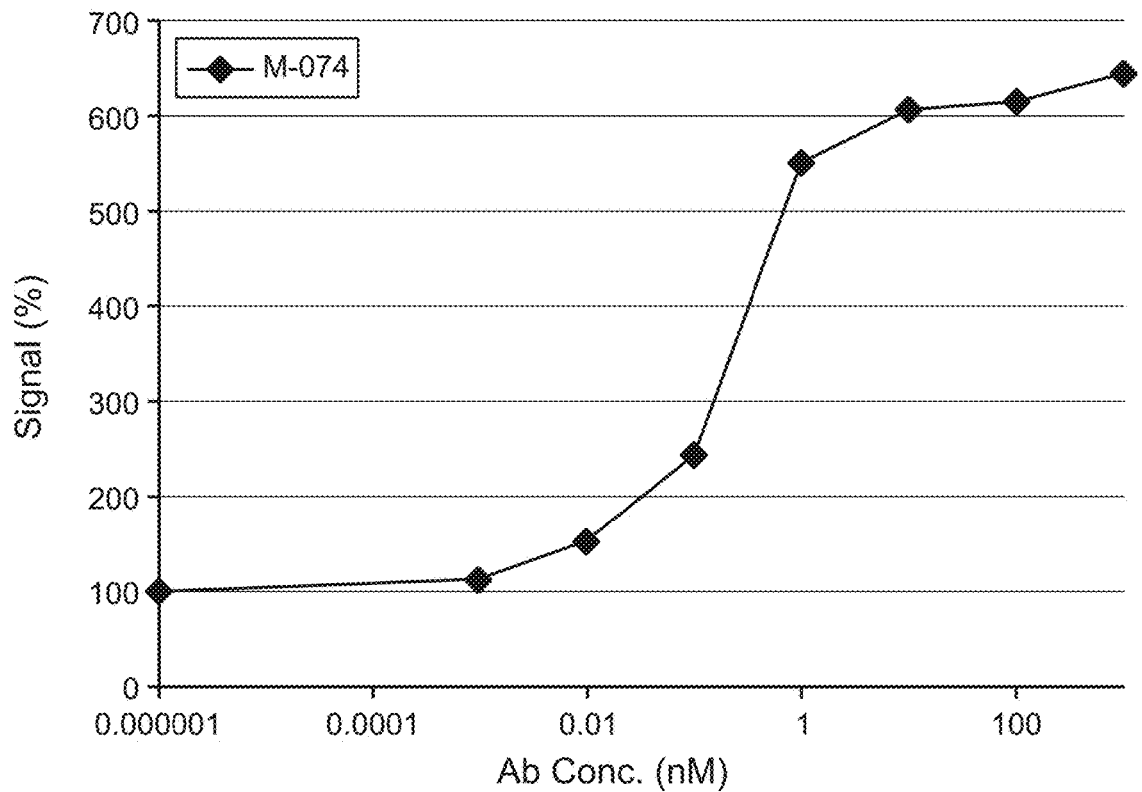
FIG. 14
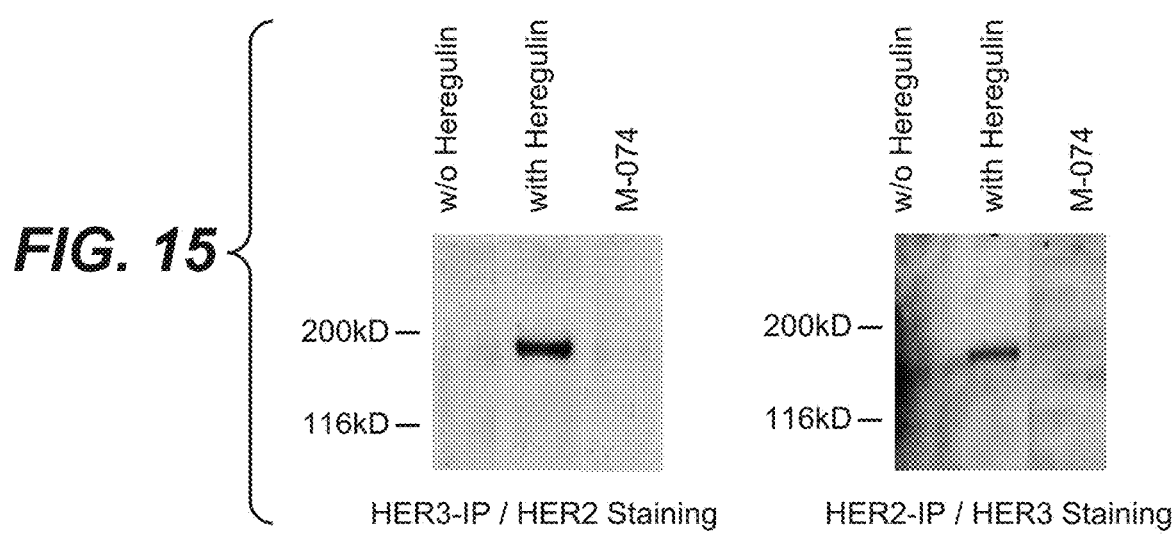
FIG. 15

SEQUENCE LISTING

```
<160> NUMBER OF SEQ ID NOS: 71

<210> SEQ ID NO 1
<211> LENGTH: 19
<212> TYPE: PRT
<213> ORGANISM: Homo Sapiens

<400> SEQUENCE: 1

Pro Gln Pro Leu Val Tyr Asn Lys Leu Thr Phe Gln Leu Glu Pro Asn
1               5                   10                  15

Pro His Thr

<210> SEQ ID NO 2
<211> LENGTH: 19
<212> TYPE: PRT
<213> ORGANISM: Homo Sapiens

<400> SEQUENCE: 2

Pro Gln Thr Phe Val Tyr Asn Pro Thr Thr Phe Gln Leu Glu His Asn
1               5                   10                  15

Phe Asn Ala

<210> SEQ ID NO 3
<211> LENGTH: 1323
<212> TYPE: PRT
<213> ORGANISM: Homo Sapiens

<400> SEQUENCE: 3

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
                20                  25                  30

Leu Tyr Glu Arg Cys Glu Val Val Met Gly Asn Leu Glu Ile Val Leu
            35                  40                  45

Thr Gly His Asn Ala Asp Leu Ser Phe Leu Gln Trp Ile Arg Glu Val
        50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95
```

```
Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
115                 120                 125

Tyr Ile Glu Lys Asn Asp Lys Leu Cys His Met Asp Thr Ile Asp Trp
        130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
        355                 360                 365

Arg Thr Val Arg Glu Ile Thr Gly Tyr Leu Asn Ile Gln Ser Trp Pro
370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
        435                 440                 445

Leu Asn Trp Thr Lys Val Leu Arg Gly Pro Thr Glu Glu Arg Leu Asp
450                 455                 460

Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
            500                 505                 510
```

-continued

```
His Cys Asn Phe Leu Asn Gly Glu Pro Arg Glu Phe Ala His Glu Ala
            515                 520                 525
Glu Cys Phe Ser Cys His Pro Glu Cys Gln Pro Met Glu Gly Thr Ala
    530                 535                 540
Thr Cys Asn Gly Ser Gly Ser Asp Thr Cys Ala Gln Cys Ala His Phe
545                 550                 555                 560
Arg Asp Gly Pro His Cys Val Ser Ser Cys Pro His Gly Val Leu Gly
                565                 570                 575
Ala Lys Gly Pro Ile Tyr Lys Tyr Pro Asp Val Gln Asn Glu Cys Arg
            580                 585                 590
Pro Cys His Glu Asn Cys Thr Gln Gly Cys Lys Gly Pro Glu Leu Gln
        595                 600                 605
Asp Cys Leu Gly Gln Thr Leu Val Leu Ile Gly Lys Thr His Leu Thr
    610                 615                 620
Met Ala Leu Thr Val Ile Ala Gly Leu Val Val Ile Phe Met Met Leu
625                 630                 635                 640
Gly Gly Thr Phe Leu Tyr Trp Arg Gly Arg Arg Ile Gln Asn Lys Arg
                645                 650                 655
Ala Met Arg Arg Tyr Leu Glu Arg Gly Glu Ser Ile Glu Pro Leu Asp
            660                 665                 670
Pro Ser Glu Lys Ala Asn Lys Val Leu Ala Arg Ile Phe Lys Glu Thr
        675                 680                 685
Glu Leu Arg Lys Leu Lys Val Leu Gly Ser Gly Val Phe Gly Thr Val
    690                 695                 700
His Lys Gly Val Trp Ile Pro Glu Gly Glu Ser Ile Lys Ile Pro Val
705                 710                 715                 720
Cys Ile Lys Val Ile Glu Asp Lys Ser Gly Arg Gln Ser Phe Gln Ala
                725                 730                 735
Val Thr Asp His Met Leu Ala Ile Gly Ser Leu Asp His Ala His Ile
            740                 745                 750
Val Arg Leu Leu Gly Leu Cys Pro Gly Ser Ser Leu Gln Leu Val Thr
        755                 760                 765
Gln Tyr Leu Pro Leu Gly Ser Leu Leu Asp His Val Arg Gln His Arg
    770                 775                 780
Gly Ala Leu Gly Pro Gln Leu Leu Leu Asn Trp Gly Val Gln Ile Ala
785                 790                 795                 800
Lys Gly Met Tyr Tyr Leu Glu Glu His Gly Met Val His Arg Asn Leu
                805                 810                 815
Ala Ala Arg Asn Val Leu Leu Lys Ser Pro Ser Gln Val Gln Val Ala
            820                 825                 830
Asp Phe Gly Val Ala Asp Leu Leu Pro Pro Asp Asp Lys Gln Leu Leu
        835                 840                 845
Tyr Ser Glu Ala Lys Thr Pro Ile Lys Trp Met Ala Leu Glu Ser Ile
    850                 855                 860
His Phe Gly Lys Tyr Thr His Gln Ser Asp Val Trp Ser Tyr Gly Val
865                 870                 875                 880
Thr Val Trp Glu Leu Met Thr Phe Gly Ala Glu Pro Tyr Ala Gly Leu
                885                 890                 895
Arg Leu Ala Glu Val Pro Asp Leu Leu Glu Lys Gly Glu Arg Leu Ala
            900                 905                 910
Gln Pro Gln Ile Cys Thr Ile Asp Val Tyr Met Val Met Val Lys Cys
        915                 920                 925
```

```
Trp Met Ile Asp Glu Asn Ile Arg Pro Thr Phe Lys Glu Leu Ala Asn
930                 935                 940

Glu Phe Thr Arg Met Ala Arg Asp Pro Arg Tyr Leu Val Ile Lys
945                 950                 955                 960

Arg Glu Ser Gly Pro Gly Ile Ala Pro Gly Pro Glu Pro His Gly Leu
                965                 970                 975

Thr Asn Lys Lys Leu Glu Glu Val Glu Leu Glu Pro Glu Leu Asp Leu
            980                 985                 990

Asp Leu Asp Leu Glu Ala Glu Glu Asp Asn Leu Ala Thr Thr Thr Leu
            995                 1000                1005

Gly Ser Ala Leu Ser Leu Pro Val Gly Thr Leu Asn Arg Pro Arg
    1010                1015                1020

Gly Ser Gln Ser Leu Leu Ser Pro Ser Ser Gly Tyr Met Pro Met
    1025                1030                1035

Asn Gln Gly Asn Leu Gly Glu Ser Cys Gln Glu Ser Ala Val Ser
    1040                1045                1050

Gly Ser Ser Glu Arg Cys Pro Arg Pro Val Ser Leu His Pro Met
    1055                1060                1065

Pro Arg Gly Cys Leu Ala Ser Glu Ser Ser Glu Gly His Val Thr
    1070                1075                1080

Gly Ser Glu Ala Glu Leu Gln Glu Lys Val Ser Met Cys Arg Ser
    1085                1090                1095

Arg Ser Arg Ser Arg Ser Pro Arg Pro Arg Gly Asp Ser Ala Tyr
    1100                1105                1110

His Ser Gln Arg His Ser Leu Leu Thr Pro Val Thr Pro Leu Ser
    1115                1120                1125

Pro Pro Gly Leu Glu Glu Glu Asp Val Asn Gly Tyr Val Met Pro
    1130                1135                1140

Asp Thr His Leu Lys Gly Thr Pro Ser Ser Arg Glu Gly Thr Leu
    1145                1150                1155

Ser Ser Val Gly Leu Ser Ser Val Leu Gly Thr Glu Glu Glu Asp
    1160                1165                1170

Glu Asp Glu Glu Tyr Glu Tyr Met Asn Arg Arg Arg Arg His Ser
    1175                1180                1185

Pro Pro His Pro Pro Arg Pro Ser Ser Leu Glu Glu Leu Gly Tyr
    1190                1195                1200

Glu Tyr Met Asp Val Gly Ser Asp Leu Ser Ala Ser Leu Gly Ser
    1205                1210                1215

Thr Gln Ser Cys Pro Leu His Pro Val Pro Ile Met Pro Thr Ala
    1220                1225                1230

Gly Thr Thr Pro Asp Glu Asp Tyr Glu Tyr Met Asn Arg Gln Arg
    1235                1240                1245

Asp Gly Gly Gly Pro Gly Gly Asp Tyr Ala Ala Met Gly Ala Cys
    1250                1255                1260

Pro Ala Ser Glu Gln Gly Tyr Glu Glu Met Arg Ala Phe Gln Gly
    1265                1270                1275

Pro Gly His Gln Ala Pro His Val His Tyr Ala Arg Leu Lys Thr
    1280                1285                1290

Leu Arg Ser Leu Glu Ala Thr Asp Ser Ala Phe Asp Asn Pro Asp
    1295                1300                1305

Tyr Trp His Ser Arg Leu Phe Pro Lys Ala Asn Ala Gln Arg Thr
    1310                1315                1320
```

```
<210> SEQ ID NO 4
<211> LENGTH: 624
<212> TYPE: PRT
<213> ORGANISM: Homo Sapiens

<400> SEQUENCE: 4

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
        355                 360                 365

Arg Thr Val Arg Glu Ile Thr Gly Tyr Leu Asn Ile Gln Ser Trp Pro
    370                 375                 380
```

```
Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
        435                 440                 445

Leu Asn Trp Thr Lys Val Leu Arg Gly Pro Thr Glu Glu Arg Leu Asp
    450                 455                 460

Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
            500                 505                 510

His Cys Asn Phe Leu Asn Gly Glu Pro Arg Glu Phe Ala His Glu Ala
        515                 520                 525

Glu Cys Phe Ser Cys His Pro Glu Cys Gln Pro Met Glu Gly Thr Ala
    530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
            580                 585                 590

Pro Cys His Glu Asn Cys Thr Gln Gly Cys Lys Gly Pro Glu Leu Gln
        595                 600                 605

Asp Cys Leu Gly Gln Thr Leu Val Leu Ile Gly Lys Thr His Leu Thr
    610                 615                 620

<210> SEQ ID NO 5
<211> LENGTH: 1283
<212> TYPE: PRT
<213> ORGANISM: Homo Sapiens

<400> SEQUENCE: 5

Gln Ser Val Cys Ala Gly Thr Glu Asn Lys Leu Ser Ser Leu Ser Asp
1               5                   10                  15

Leu Glu Gln Gln Tyr Arg Ala Leu Arg Lys Tyr Tyr Glu Asn Cys Glu
            20                  25                  30

Val Val Met Gly Asn Leu Glu Ile Thr Ser Ile Glu His Asn Arg Asp
        35                  40                  45

Leu Ser Phe Leu Arg Ser Val Arg Glu Val Thr Gly Tyr Val Leu Val
    50                  55                  60

Ala Leu Asn Gln Phe Arg Tyr Leu Pro Leu Glu Asn Leu Arg Ile Ile
65                  70                  75                  80

Arg Gly Thr Lys Leu Tyr Glu Asp Arg Tyr Ala Leu Ala Ile Phe Leu
                85                  90                  95

Asn Tyr Arg Lys Asp Gly Asn Phe Gly Leu Gln Glu Leu Gly Leu Lys
            100                 105                 110

Asn Leu Thr Glu Ile Leu Asn Gly Gly Val Tyr Val Asp Gln Asn Lys
        115                 120                 125

Phe Leu Cys Tyr Ala Asp Thr Ile His Trp Gln Asp Ile Val Arg Asn
    130                 135                 140
```

-continued

```
Pro Trp Pro Ser Asn Leu Thr Leu Val Ser Thr Asn Gly Ser Ser Gly
145                 150                 155                 160

Cys Gly Arg Cys His Lys Ser Cys Thr Gly Arg Cys Trp Gly Pro Thr
            165                 170                 175

Glu Asn His Cys Gln Thr Leu Thr Arg Thr Val Cys Ala Glu Gln Cys
        180                 185                 190

Asp Gly Arg Cys Tyr Gly Pro Tyr Val Ser Asp Cys Cys His Arg Glu
    195                 200                 205

Cys Ala Gly Gly Cys Ser Gly Pro Lys Asp Thr Asp Cys Phe Ala Cys
210                 215                 220

Met Asn Phe Asn Asp Ser Gly Ala Cys Val Thr Gln Cys Pro Gln Thr
225                 230                 235                 240

Phe Val Tyr Asn Pro Thr Thr Phe Gln Leu Glu His Asn Phe Asn Ala
                245                 250                 255

Lys Tyr Thr Tyr Gly Ala Phe Cys Val Lys Lys Cys Pro His Asn Phe
            260                 265                 270

Val Val Asp Ser Ser Cys Val Arg Ala Cys Pro Ser Ser Lys Met
        275                 280                 285

Glu Val Glu Glu Asn Gly Ile Lys Met Cys Lys Pro Cys Thr Asp Ile
290                 295                 300

Cys Pro Lys Ala Cys Asp Gly Ile Gly Thr Gly Ser Leu Met Ser Ala
305             310                 315                 320

Gln Thr Val Asp Ser Ser Asn Ile Asp Lys Phe Ile Asn Cys Thr Lys
                325                 330                 335

Ile Asn Gly Asn Leu Ile Phe Leu Val Thr Gly Ile His Gly Asp Pro
            340                 345                 350

Tyr Asn Ala Ile Glu Ala Ile Asp Pro Glu Lys Leu Asn Val Phe Arg
        355                 360                 365

Thr Val Arg Glu Ile Thr Gly Phe Leu Asn Ile Gln Ser Trp Pro Pro
    370                 375                 380

Asn Met Thr Asp Phe Ser Val Phe Ser Asn Leu Val Thr Ile Gly Gly
385                 390                 395                 400

Arg Val Leu Tyr Ser Gly Leu Ser Leu Leu Ile Leu Lys Gln Gln Gly
                405                 410                 415

Ile Thr Ser Leu Gln Phe Gln Ser Leu Lys Glu Ile Ser Ala Gly Asn
            420                 425                 430

Ile Tyr Ile Thr Asp Asn Ser Asn Leu Cys Tyr Tyr His Thr Ile Asn
        435                 440                 445

Trp Thr Thr Leu Phe Ser Thr Ile Asn Gln Arg Ile Val Ile Arg Asp
    450                 455                 460

Asn Arg Lys Ala Glu Asn Cys Thr Ala Glu Gly Met Val Cys Asn His
465                 470                 475                 480

Leu Cys Ser Ser Asp Gly Cys Trp Gly Pro Gly Pro Asp Gln Cys Leu
                485                 490                 495

Ser Cys Arg Arg Phe Ser Arg Gly Arg Ile Cys Ile Glu Ser Cys Asn
            500                 505                 510

Leu Tyr Asp Gly Glu Phe Arg Glu Phe Glu Asn Gly Ser Ile Cys Val
        515                 520                 525

Glu Cys Asp Pro Gln Cys Glu Lys Met Glu Asp Gly Leu Leu Thr Cys
    530                 535                 540

His Gly Pro Gly Pro Asp Asn Cys Thr Lys Cys Ser His Phe Lys Asp
545                 550                 555                 560
```

```
Gly Pro Asn Cys Val Glu Lys Cys Pro Asp Gly Leu Gln Gly Ala Asn
                565                 570                 575
Ser Phe Ile Phe Lys Tyr Ala Asp Pro Asp Arg Glu Cys His Pro Cys
            580                 585                 590
His Pro Asn Cys Thr Gln Gly Cys Asn Gly Pro Thr Ser His Asp Cys
        595                 600                 605
Ile Tyr Tyr Pro Trp Thr Gly His Ser Thr Leu Pro Gln His Ala Arg
    610                 615                 620
Thr Pro Leu Ile Ala Ala Gly Val Ile Gly Leu Phe Ile Leu Val
625                 630                 635                 640
Ile Val Gly Leu Thr Phe Ala Val Tyr Val Arg Arg Lys Ser Ile Lys
                645                 650                 655
Lys Lys Arg Ala Leu Arg Arg Phe Leu Glu Thr Glu Leu Val Glu Pro
            660                 665                 670
Leu Thr Pro Ser Gly Thr Ala Pro Asn Gln Ala Gln Leu Arg Ile Leu
        675                 680                 685
Lys Glu Thr Glu Leu Lys Arg Val Lys Val Leu Gly Ser Gly Ala Phe
    690                 695                 700
Gly Thr Val Tyr Lys Gly Ile Trp Val Pro Glu Gly Glu Thr Val Lys
705                 710                 715                 720
Ile Pro Val Ala Ile Lys Ile Leu Asn Glu Thr Thr Gly Pro Lys Ala
                725                 730                 735
Asn Val Glu Phe Met Asp Glu Ala Leu Ile Met Ala Ser Met Asp His
            740                 745                 750
Pro His Leu Val Arg Leu Leu Gly Val Cys Leu Ser Pro Thr Ile Gln
        755                 760                 765
Leu Val Thr Gln Leu Met Pro His Gly Cys Leu Leu Glu Tyr Val His
    770                 775                 780
Glu His Lys Asp Asn Ile Gly Ser Gln Leu Leu Leu Asn Trp Cys Val
785                 790                 795                 800
Gln Ile Ala Lys Gly Met Met Tyr Leu Glu Glu Arg Arg Leu Val His
                805                 810                 815
Arg Asp Leu Ala Ala Arg Asn Val Leu Val Lys Ser Pro Asn His Val
            820                 825                 830
Lys Ile Thr Asp Phe Gly Leu Ala Arg Leu Leu Glu Gly Asp Glu Lys
        835                 840                 845
Glu Tyr Asn Ala Asp Gly Gly Lys Met Pro Ile Lys Trp Met Ala Leu
    850                 855                 860
Glu Cys Ile His Tyr Arg Lys Phe Thr His Gln Ser Asp Val Trp Ser
865                 870                 875                 880
Tyr Gly Val Thr Ile Trp Glu Leu Met Thr Phe Gly Gly Lys Pro Tyr
                885                 890                 895
Asp Gly Ile Pro Thr Arg Glu Ile Pro Asp Leu Leu Glu Lys Gly Glu
            900                 905                 910
Arg Leu Pro Gln Pro Pro Ile Cys Thr Ile Asp Val Tyr Met Val Met
        915                 920                 925
Val Lys Cys Trp Met Ile Asp Ala Asp Ser Arg Pro Lys Phe Lys Glu
    930                 935                 940
Leu Ala Ala Glu Phe Ser Arg Met Ala Arg Asp Pro Gln Arg Tyr Leu
945                 950                 955                 960
Val Ile Gln Gly Asp Asp Arg Met Lys Leu Pro Ser Pro Asn Asp Ser
                965                 970                 975
```

```
Lys Phe Phe Gln Asn Leu Leu Asp Glu Glu Asp Leu Glu Asp Met Met
            980                 985                 990

Asp Ala Glu Glu Tyr Leu Val Pro  Gln Ala Phe Asn Ile  Pro Pro Pro
        995                1000                1005

Ile Tyr Thr Ser Arg Ala Arg Ile Asp Ser Asn Arg  Ser Glu Ile
   1010                1015                1020

Gly His Ser Pro Pro Ala Tyr Thr Pro Met Ser  Gly Asn Gln
   1025                1030                1035

Phe Val Tyr Arg Asp Gly Gly Phe Ala Ala Glu Gln  Gly Val Ser
   1040                1045                1050

Val Pro Tyr Arg Ala Pro Thr Ser Thr Ile Pro Glu  Ala Pro Val
   1055                1060                1065

Ala Gln Gly Ala Thr Ala Glu Ile Phe Asp Asp Ser  Cys Cys Asn
   1070                1075                1080

Gly Thr Leu Arg Lys Pro Val Ala Pro His Val Gln  Glu Asp Ser
   1085                1090                1095

Ser Thr Gln Arg Tyr Ser Ala Asp Pro Thr Val Phe  Ala Pro Glu
   1100                1105                1110

Arg Ser Pro Arg Gly Glu Leu Asp Glu Glu Gly Tyr  Met Thr Pro
   1115                1120                1125

Met Arg Asp Lys Pro Lys Gln Glu Tyr Leu Asn Pro  Val Glu Glu
   1130                1135                1140

Asn Pro Phe Val Ser Arg Arg Lys Asn Gly Asp Leu  Gln Ala Leu
   1145                1150                1155

Asp Asn Pro Glu Tyr His Asn Ala Ser Asn Gly Pro  Pro Lys Ala
   1160                1165                1170

Glu Asp Glu Tyr Val Asn Glu Pro Leu Tyr Leu Asn  Thr Phe Ala
   1175                1180                1185

Asn Thr Leu Gly Lys Ala Glu Tyr Leu Lys Asn Asn  Ile Leu Ser
   1190                1195                1200

Met Pro Glu Lys Ala Lys Lys Ala Phe Asp Asn Pro  Asp Tyr Trp
   1205                1210                1215

Asn His Ser Leu Pro Pro Arg Ser Thr Leu Gln His  Pro Asp Tyr
   1220                1225                1230

Leu Gln Glu Tyr Ser Thr Lys Tyr Phe Tyr Lys Gln  Asn Gly Arg
   1235                1240                1245

Ile Arg Pro Ile Val Ala Glu Asn Pro Glu Tyr Leu  Ser Glu Phe
   1250                1255                1260

Ser Leu Lys Pro Gly Thr Val Leu Pro Pro Pro  Tyr Arg His
   1265                1270                1275

Arg Asn Thr Val Val
   1280

<210> SEQ ID NO 6
<211> LENGTH: 626
<212> TYPE: PRT
<213> ORGANISM: Homo Sapiens

<400> SEQUENCE: 6

Gln Ser Val Cys Ala Gly Thr Glu Asn Lys Leu Ser Ser Leu Ser Asp
1               5                   10                  15

Leu Glu Gln Gln Tyr Arg Ala Leu Arg Lys Tyr Tyr Glu Asn Cys Glu
            20                  25                  30

Val Val Met Gly Asn Leu Glu Ile Thr Ser Ile Glu His Asn Arg Asp
        35                  40                  45
```

```
Leu Ser Phe Leu Arg Ser Val Arg Glu Val Thr Gly Tyr Val Leu Val
 50                  55                  60
Ala Leu Asn Gln Phe Arg Tyr Leu Pro Leu Glu Asn Leu Arg Ile Ile
 65                  70                  75                  80
Arg Gly Thr Lys Leu Tyr Glu Asp Arg Tyr Ala Leu Ala Ile Phe Leu
                 85                  90                  95
Asn Tyr Arg Lys Asp Gly Asn Phe Gly Leu Gln Glu Leu Gly Leu Lys
                100                 105                 110
Asn Leu Thr Glu Ile Leu Asn Gly Gly Val Tyr Val Asp Gln Asn Lys
                115                 120                 125
Phe Leu Cys Tyr Ala Asp Thr Ile His Trp Gln Asp Ile Val Arg Asn
130                 135                 140
Pro Trp Pro Ser Asn Leu Thr Leu Val Ser Thr Asn Gly Ser Ser Gly
145                 150                 155                 160
Cys Gly Arg Cys His Lys Ser Cys Thr Gly Arg Cys Trp Gly Pro Thr
                165                 170                 175
Glu Asn His Cys Gln Thr Leu Thr Arg Thr Val Cys Ala Glu Gln Cys
                180                 185                 190
Asp Gly Arg Cys Tyr Gly Pro Tyr Val Ser Asp Cys Cys His Arg Glu
                195                 200                 205
Cys Ala Gly Gly Cys Ser Gly Pro Lys Asp Thr Asp Cys Phe Ala Cys
210                 215                 220
Met Asn Phe Asn Asp Ser Gly Ala Cys Val Thr Gln Cys Pro Gln Thr
225                 230                 235                 240
Phe Val Tyr Asn Pro Thr Thr Phe Gln Leu Glu His Asn Phe Asn Ala
                245                 250                 255
Lys Tyr Thr Tyr Gly Ala Phe Cys Val Lys Lys Cys Pro His Asn Phe
                260                 265                 270
Val Val Asp Ser Ser Ser Cys Val Arg Ala Cys Pro Ser Ser Lys Met
                275                 280                 285
Glu Val Glu Glu Asn Gly Ile Lys Met Cys Lys Pro Cys Thr Asp Ile
290                 295                 300
Cys Pro Lys Ala Cys Asp Gly Ile Gly Thr Gly Ser Leu Met Ser Ala
305                 310                 315                 320
Gln Thr Val Asp Ser Ser Asn Ile Asp Lys Phe Ile Asn Cys Thr Lys
                325                 330                 335
Ile Asn Gly Asn Leu Ile Phe Leu Val Thr Gly Ile His Gly Asp Pro
                340                 345                 350
Tyr Asn Ala Ile Glu Ala Ile Asp Pro Glu Lys Leu Asn Val Phe Arg
                355                 360                 365
Thr Val Arg Glu Ile Thr Gly Phe Leu Asn Ile Gln Ser Trp Pro Pro
                370                 375                 380
Asn Met Thr Asp Phe Ser Val Phe Ser Asn Leu Val Thr Ile Gly Gly
385                 390                 395                 400
Arg Val Leu Tyr Ser Gly Leu Ser Leu Leu Ile Leu Lys Gln Gln Gly
                405                 410                 415
Ile Thr Ser Leu Gln Phe Gln Ser Leu Lys Glu Ile Ser Ala Gly Asn
                420                 425                 430
Ile Tyr Ile Thr Asp Asn Ser Asn Leu Cys Tyr Tyr His Thr Ile Asn
                435                 440                 445
Trp Thr Thr Leu Phe Ser Thr Ile Asn Gln Arg Ile Val Ile Arg Asp
450                 455                 460
```

```
Asn Arg Lys Ala Glu Asn Cys Thr Ala Glu Gly Met Val Cys Asn His
465                 470                 475                 480

Leu Cys Ser Ser Asp Gly Cys Trp Gly Pro Gly Pro Asp Gln Cys Leu
            485                 490                 495

Ser Cys Arg Arg Phe Ser Arg Gly Arg Ile Cys Ile Glu Ser Cys Asn
        500                 505                 510

Leu Tyr Asp Gly Glu Phe Arg Glu Phe Glu Asn Gly Ser Ile Cys Val
    515                 520                 525

Glu Cys Asp Pro Gln Cys Glu Lys Met Glu Asp Gly Leu Leu Thr Cys
530                 535                 540

His Gly Pro Gly Pro Asp Asn Cys Thr Lys Cys Ser His Phe Lys Asp
545                 550                 555                 560

Gly Pro Asn Cys Val Glu Lys Cys Pro Asp Gly Leu Gln Gly Ala Asn
            565                 570                 575

Ser Phe Ile Phe Lys Tyr Ala Asp Pro Asp Arg Glu Cys His Pro Cys
        580                 585                 590

His Pro Asn Cys Thr Gln Gly Cys Asn Gly Pro Thr Ser His Asp Cys
    595                 600                 605

Ile Tyr Tyr Pro Trp Thr Gly His Ser Thr Leu Pro Gln His Ala Arg
610                 615                 620

Thr Pro
625

<210> SEQ ID NO 7
<211> LENGTH: 1186
<212> TYPE: PRT
<213> ORGANISM: Homo Sapiens

<400> SEQUENCE: 7

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205
```

-continued

```
His Asn Gln Cys Ala Ala Gly Cys Thr Gly Pro Arg Glu Ser Asp Cys
    210                 215                 220
Leu Val Cys Arg Lys Phe Arg Asp Glu Ala Thr Cys Lys Asp Thr Cys
225                 230                 235                 240
Pro Pro Leu Met Leu Tyr Asn Pro Thr Thr Tyr Gln Met Asp Val Asn
            245                 250                 255
Pro Glu Gly Lys Tyr Ser Phe Gly Ala Thr Cys Val Lys Lys Cys Pro
                260                 265                 270
Arg Asn Tyr Val Val Thr Asp His Gly Ser Cys Val Arg Ala Cys Gly
            275                 280                 285
Ala Asp Ser Tyr Glu Met Glu Glu Asp Gly Val Arg Lys Cys Lys Lys
290                 295                 300
Cys Glu Gly Pro Cys Arg Lys Val Cys Asn Gly Ile Gly Ile Gly Glu
305                 310                 315                 320
Phe Lys Asp Ser Leu Ser Ile Asn Ala Thr Asn Ile Lys His Phe Lys
                325                 330                 335
Asn Cys Thr Ser Ile Ser Gly Asp Leu His Ile Leu Pro Val Ala Phe
            340                 345                 350
Arg Gly Asp Ser Phe Thr His Thr Pro Pro Leu Asp Pro Gln Glu Leu
        355                 360                 365
Asp Ile Leu Lys Thr Val Lys Glu Ile Thr Gly Phe Leu Leu Ile Gln
370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
            420                 425                 430
Ser Asp Gly Asp Val Ile Ile Ser Gly Asn Lys Asn Leu Cys Tyr Ala
        435                 440                 445
Asn Thr Ile Asn Trp Lys Lys Leu Phe Gly Thr Ser Gly Gln Lys Thr
    450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Arg Asn Val Ser Arg Gly Arg Glu Cys Val
            500                 505                 510
Asp Lys Cys Asn Leu Leu Glu Gly Glu Pro Arg Glu Phe Val Glu Asn
        515                 520                 525
Ser Glu Cys Ile Gln Cys His Pro Glu Cys Leu Pro Gln Ala Met Asn
    530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
                565                 570                 575
Gly Glu Asn Asn Thr Leu Val Trp Lys Tyr Ala Asp Ala Gly His Val
            580                 585                 590
Cys His Leu Cys His Pro Asn Cys Thr Tyr Gly Cys Thr Gly Pro Gly
        595                 600                 605
Leu Glu Gly Cys Pro Thr Asn Gly Pro Lys Ile Pro Ser Ile Ala Thr
    610                 615                 620
```

```
Gly Met Val Gly Ala Leu Leu Leu Leu Val Ala Leu Gly Ile
625                 630                 635                 640

Gly Leu Phe Met Arg Arg His Ile Val Arg Lys Arg Thr Leu Arg
        645                 650                 655

Arg Leu Leu Gln Glu Arg Glu Leu Val Glu Pro Leu Thr Pro Ser Gly
            660                 665                 670

Glu Ala Pro Asn Gln Ala Leu Leu Arg Ile Leu Lys Glu Thr Glu Phe
        675                 680                 685

Lys Lys Ile Lys Val Leu Gly Ser Gly Ala Phe Gly Thr Val Tyr Lys
690                 695                 700

Gly Leu Trp Ile Pro Glu Gly Glu Lys Val Lys Ile Pro Val Ala Ile
705                 710                 715                 720

Lys Glu Leu Arg Glu Ala Thr Ser Pro Lys Ala Asn Lys Glu Ile Leu
            725                 730                 735

Asp Glu Ala Tyr Val Met Ala Ser Val Asp Asn Pro His Val Cys Arg
            740                 745                 750

Leu Leu Gly Ile Cys Leu Thr Ser Thr Val Gln Leu Ile Thr Gln Leu
        755                 760                 765

Met Pro Phe Gly Cys Leu Leu Asp Tyr Val Arg Glu His Lys Asp Asn
770                 775                 780

Ile Gly Ser Gln Tyr Leu Leu Asn Trp Cys Val Gln Ile Ala Lys Gly
785                 790                 795                 800

Met Asn Tyr Leu Glu Asp Arg Arg Leu Val His Arg Asp Leu Ala Ala
            805                 810                 815

Arg Asn Val Leu Val Lys Thr Pro Gln His Val Lys Ile Thr Asp Phe
            820                 825                 830

Gly Leu Ala Lys Leu Leu Gly Ala Glu Glu Lys Glu Tyr His Ala Glu
        835                 840                 845

Gly Gly Lys Val Pro Ile Lys Trp Met Ala Leu Glu Ser Ile Leu His
850                 855                 860

Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
            885                 890                 895

Ser Glu Ile Ser Ser Ile Leu Glu Lys Gly Glu Arg Leu Pro Gln Pro
        900                 905                 910

Pro Ile Cys Thr Ile Asp Val Tyr Met Ile Met Val Lys Cys Trp Met
        915                 920                 925

Ile Asp Ala Asp Ser Arg Pro Lys Phe Arg Glu Leu Ile Ile Glu Phe
930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
            965                 970                 975

Leu Met Asp Glu Glu Asp Met Asp Asp Val Val Asp Ala Asp Glu Tyr
            980                 985                 990

Leu Ile Pro Gln Gln Gly Phe Phe Ser Ser Pro Ser Thr Ser Arg Thr
        995                 1000                1005

Pro Leu Leu Ser Ser Leu Ser Ala Thr Ser Asn Asn Ser Thr Val
        1010                1015                1020

Ala Cys Ile Asp Arg Asn Gly Leu Gln Ser Cys Pro Ile Lys Glu
        1025                1030                1035
```

-continued

Asp Ser Phe Leu Gln Arg Tyr Ser Ser Asp Pro Thr Gly Ala Leu
    1040                1045                1050

Thr Glu Asp Ser Ile Asp Asp Thr Phe Leu Pro Val Pro Glu Tyr
    1055                1060                1065

Ile Asn Gln Ser Val Pro Lys Arg Pro Ala Gly Ser Val Gln Asn
    1070                1075                1080

Pro Val Tyr His Asn Gln Pro Leu Asn Pro Ala Pro Ser Arg Asp
    1085                1090                1095

Pro His Tyr Gln Asp Pro His Ser Thr Ala Val Gly Asn Pro Glu
    1100                1105                1110

Tyr Leu Asn Thr Val Gln Pro Thr Cys Val Asn Ser Thr Phe Asp
    1115                1120                1125

Ser Pro Ala His Trp Ala Gln Lys Gly Ser His Gln Ile Ser Leu
    1130                1135                1140

Asp Asn Pro Asp Tyr Gln Gln Asp Phe Phe Pro Lys Glu Ala Lys
    1145                1150                1155

Pro Asn Gly Ile Phe Lys Gly Ser Thr Ala Glu Asn Ala Glu Tyr
    1160                1165                1170

Leu Arg Val Ala Pro Gln Ser Ser Glu Phe Ile Gly Ala
    1175                1180                1185

<210> SEQ ID NO 8
<211> LENGTH: 621
<212> TYPE: PRT
<213> ORGANISM: Homo Sapiens

<400> SEQUENCE: 8

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

```
His Asn Gln Cys Ala Ala Gly Cys Thr Gly Pro Arg Glu Ser Asp Cys
210                 215                 220
Leu Val Cys Arg Lys Phe Arg Asp Glu Ala Thr Cys Lys Asp Thr Cys
225                 230                 235                 240
Pro Pro Leu Met Leu Tyr Asn Pro Thr Thr Tyr Gln Met Asp Val Asn
                245                 250                 255
Pro Glu Gly Lys Tyr Ser Phe Gly Ala Thr Cys Val Lys Lys Cys Pro
                260                 265                 270
Arg Asn Tyr Val Val Thr Asp His Gly Ser Cys Val Arg Ala Cys Gly
            275                 280                 285
Ala Asp Ser Tyr Glu Met Glu Glu Asp Gly Val Arg Lys Cys Lys Lys
290                 295                 300
Cys Glu Gly Pro Cys Arg Lys Val Cys Asn Gly Ile Gly Ile Gly Glu
305                 310                 315                 320
Phe Lys Asp Ser Leu Ser Ile Asn Ala Thr Asn Ile Lys His Phe Lys
                325                 330                 335
Asn Cys Thr Ser Ile Ser Gly Asp Leu His Ile Leu Pro Val Ala Phe
                340                 345                 350
Arg Gly Asp Ser Phe Thr His Thr Pro Pro Leu Asp Pro Gln Glu Leu
            355                 360                 365
Asp Ile Leu Lys Thr Val Lys Glu Ile Thr Gly Phe Leu Leu Ile Gln
370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
                420                 425                 430
Ser Asp Gly Asp Val Ile Ile Ser Gly Asn Lys Asn Leu Cys Tyr Ala
            435                 440                 445
Asn Thr Ile Asn Trp Lys Lys Leu Phe Gly Thr Ser Gly Gln Lys Thr
450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Arg Asn Val Ser Arg Gly Arg Glu Cys Val
                500                 505                 510
Asp Lys Cys Asn Leu Leu Glu Gly Glu Pro Arg Glu Phe Val Glu Asn
            515                 520                 525
Ser Glu Cys Ile Gln Cys His Pro Glu Cys Leu Pro Gln Ala Met Asn
530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
                565                 570                 575
Gly Glu Asn Asn Thr Leu Val Trp Lys Tyr Ala Asp Ala Gly His Val
                580                 585                 590
Cys His Leu Cys His Pro Asn Cys Thr Tyr Gly Cys Thr Gly Pro Gly
            595                 600                 605
Leu Glu Gly Cys Pro Thr Asn Gly Pro Lys Ile Pro Ser
610                 615                 620
```

<210> SEQ ID NO 9
<211> LENGTH: 1233
<212> TYPE: PRT
<213> ORGANISM: Homo Sapiens

<400> SEQUENCE: 9

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380
```

```
Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
            405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
        450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
            485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
        530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
            565                 570                 575

Arg Cys Pro Ser Gly Val Lys Pro Asp Leu Ser Tyr Met Pro Ile Trp
        580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
        610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
            645                 650                 655

Gln Gln Lys Ile Arg Lys Tyr Thr Met Arg Arg Leu Leu Gln Glu Thr
            660                 665                 670

Glu Leu Val Glu Pro Leu Thr Pro Ser Gly Ala Met Pro Asn Gln Ala
            675                 680                 685

Gln Met Arg Ile Leu Lys Glu Thr Glu Leu Arg Lys Val Lys Val Leu
        690                 695                 700

Gly Ser Gly Ala Phe Gly Thr Val Tyr Lys Gly Ile Trp Ile Pro Asp
705                 710                 715                 720

Gly Glu Asn Val Lys Ile Pro Val Ala Ile Lys Val Leu Arg Glu Asn
            725                 730                 735

Thr Ser Pro Lys Ala Asn Lys Glu Ile Leu Asp Glu Ala Tyr Val Met
            740                 745                 750

Ala Gly Val Gly Ser Pro Tyr Val Ser Arg Leu Leu Gly Ile Cys Leu
            755                 760                 765

Thr Ser Thr Val Gln Leu Val Thr Gln Leu Met Pro Tyr Gly Cys Leu
        770                 775                 780

Leu Asp His Val Arg Glu Asn Arg Gly Arg Leu Gly Ser Gln Asp Leu
785                 790                 795                 800
```

-continued

Leu Asn Trp Cys Met Gln Ile Ala Lys Gly Met Ser Tyr Leu Glu Asp
            805                 810                 815

Val Arg Leu Val His Arg Asp Leu Ala Ala Arg Asn Val Leu Val Lys
        820                 825                 830

Ser Pro Asn His Val Lys Ile Thr Asp Phe Gly Leu Ala Arg Leu Leu
        835                 840                 845

Asp Ile Asp Glu Thr Glu Tyr His Ala Asp Gly Gly Lys Val Pro Ile
850                 855                 860

Lys Trp Met Ala Leu Glu Ser Ile Leu Arg Arg Arg Phe Thr His Gln
865                 870                 875                 880

Ser Asp Val Trp Ser Tyr Gly Val Thr Val Trp Glu Leu Met Thr Phe
                885                 890                 895

Gly Ala Lys Pro Tyr Asp Gly Ile Pro Ala Arg Glu Ile Pro Asp Leu
            900                 905                 910

Leu Glu Lys Gly Glu Arg Leu Pro Gln Pro Pro Ile Cys Thr Ile Asp
        915                 920                 925

Val Tyr Met Ile Met Val Lys Cys Trp Met Ile Asp Ser Glu Cys Arg
    930                 935                 940

Pro Arg Phe Arg Glu Leu Val Ser Glu Phe Ser Arg Met Ala Arg Asp
945                 950                 955                 960

Pro Gln Arg Phe Val Val Ile Gln Asn Glu Asp Leu Gly Pro Ala Ser
                965                 970                 975

Pro Leu Asp Ser Thr Phe Tyr Arg Ser Leu Leu Glu Asp Asp Met
            980                 985                 990

Gly Asp Leu Val Asp Ala Glu Glu Tyr Leu Val Pro Gln Gln Gly Phe
        995                 1000                1005

Phe Cys Pro Asp Pro Ala Pro Gly Ala Gly Gly Met Val His His
    1010                1015                1020

Arg His Arg Ser Ser Ser Thr Arg Ser Gly Gly Gly Asp Leu Thr
    1025                1030                1035

Leu Gly Leu Glu Pro Ser Glu Glu Glu Ala Pro Arg Ser Pro Leu
    1040                1045                1050

Ala Pro Ser Glu Gly Ala Gly Ser Asp Val Phe Asp Gly Asp Leu
    1055                1060                1065

Gly Met Gly Ala Ala Lys Gly Leu Gln Ser Leu Pro Thr His Asp
    1070                1075                1080

Pro Ser Pro Leu Gln Arg Tyr Ser Glu Asp Pro Thr Val Pro Leu
    1085                1090                1095

Pro Ser Glu Thr Asp Gly Tyr Val Ala Pro Leu Thr Cys Ser Pro
    1100                1105                1110

Gln Pro Glu Tyr Val Asn Gln Pro Asp Val Arg Pro Gln Pro Pro
    1115                1120                1125

Ser Pro Arg Glu Gly Pro Leu Pro Ala Ala Arg Pro Ala Gly Ala
    1130                1135                1140

Thr Leu Glu Arg Pro Lys Thr Leu Ser Pro Gly Lys Asn Gly Val
    1145                1150                1155

Val Lys Asp Val Phe Ala Phe Gly Gly Ala Val Glu Asn Pro Glu
    1160                1165                1170

Tyr Leu Thr Pro Gln Gly Gly Ala Ala Pro Gln Pro His Pro Pro
    1175                1180                1185

Pro Ala Phe Ser Pro Ala Phe Asp Asn Leu Tyr Tyr Trp Asp Gln
    1190                1195                1200

Asp Pro Pro Glu Arg Gly Ala Pro Pro Ser Thr Phe Lys Gly Thr
    1205                1210                1215

Pro Thr Ala Glu Asn Pro Glu Tyr Leu Gly Leu Asp Val Pro Val
    1220                1225                1230

<210> SEQ ID NO 10
<211> LENGTH: 630
<212> TYPE: PRT
<213> ORGANISM: Homo Sapiens

<400> SEQUENCE: 10

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

```
Ala Phe Leu Pro Glu Ser Phe Asp Gly Asp Pro Ala Ser Asn Thr Ala
            355                 360                 365

Pro Leu Gln Pro Glu Gln Leu Gln Val Phe Glu Thr Leu Glu Glu Ile
        370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
            530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
            610                 615                 620

Arg Ala Ser Pro Leu Thr
625                 630

<210> SEQ ID NO 11
<211> LENGTH: 231
<212> TYPE: PRT
<213> ORGANISM: Homo Sapiens

<400> SEQUENCE: 11

Gly Pro Gly Ser Ser Gly Lys Lys Pro Glu Ser Ala Ala Gly Ser Gln
1               5                   10                  15

Ser Pro Ala Leu Pro Pro Gln Leu Lys Glu Met Lys Ser Gln Glu Ser
            20                  25                  30

Ala Ala Gly Ser Lys Leu Val Leu Arg Cys Glu Thr Ser Ser Glu Tyr
        35                  40                  45

Ser Ser Leu Arg Phe Lys Trp Phe Lys Asn Gly Asn Glu Leu Asn Arg
    50                  55                  60

Lys Asn Lys Pro Gln Asn Ile Lys Ile Gln Lys Lys Pro Gly Lys Ser
65                  70                  75                  80

Glu Leu Arg Ile Asn Lys Ala Ser Leu Ala Asp Ser Gly Glu Tyr Met
                85                  90                  95
```

```
Cys Lys Val Ile Ser Lys Leu Gly Asn Asp Ser Ala Ser Ala Asn Ile
                100                 105                 110

Thr Ile Val Glu Ser Asn Glu Ile Ile Thr Gly Met Pro Ala Ser Thr
            115                 120                 125

Glu Gly Ala Tyr Val Ser Ser Glu Ser Pro Ile Arg Ile Ser Val Ser
        130                 135                 140

Thr Glu Gly Ala Asn Thr Ser Ser Ser Thr Ser Thr Ser Thr Thr Gly
145                 150                 155                 160

Thr Ser His Leu Val Lys Cys Ala Glu Lys Glu Lys Thr Phe Cys Val
                165                 170                 175

Asn Gly Gly Glu Cys Phe Met Val Lys Asp Leu Ser Asn Pro Ser Arg
            180                 185                 190

Tyr Leu Cys Lys Cys Pro Asn Glu Phe Thr Gly Asp Arg Cys Gln Asn
        195                 200                 205

Tyr Val Met Ala Ser Phe Tyr Lys His Leu Gly Ile Glu Phe Met Glu
    210                 215                 220

Ala Glu Glu Leu Tyr Gln Lys
225                 230

<210> SEQ ID NO 12
<211> LENGTH: 65
<212> TYPE: PRT
<213> ORGANISM: Homo Sapiens

<400> SEQUENCE: 12

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe Met Glu Ala
    50                  55                  60

Glu
65

<210> SEQ ID NO 13
<211> LENGTH: 133
<212> TYPE: PRT
<213> ORGANISM: Artificial
<220> FEATURE:
<223> OTHER INFORMATION: TtSlyD-FKBP-Her3

<400> SEQUENCE: 13

Met Arg Ser Lys Val Gly Gln Asp Lys Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Ala Gly Ser Pro Gln Pro Leu Val Tyr Asn Lys Leu Thr Phe
65                  70                  75                  80

Gln Leu Glu Pro Asn Pro His Thr Lys Gly Ser Ser Gly Lys Asp Leu
                85                  90                  95
```

Asp Phe Gln Val Glu Val Val Lys Val Arg Glu Ala Thr Pro Glu Glu
            100                 105                 110

Leu Leu His Gly His Ala His Gly Gly Gly Ser Arg Lys His His His
        115                 120                 125

His His His His His
        130

<210> SEQ ID NO 14
<211> LENGTH: 166
<212> TYPE: PRT
<213> ORGANISM: Thermus thermophilus

<400> SEQUENCE: 14

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro His Asp Pro Glu Gly Val Gln Val Pro Leu Ser
65                  70                  75                  80

Ala Phe Pro Glu Asp Ala Glu Val Val Pro Gly Ala Gln Phe Tyr Ala
                85                  90                  95

Gln Asp Met Glu Gly Asn Pro Met Pro Leu Thr Val Ala Val Glu
            100                 105                 110

Gly Glu Glu Val Thr Val Asp Phe Asn His Pro Leu Ala Gly Lys Asp
        115                 120                 125

Leu Asp Phe Gln Val Glu Val Val Lys Val Arg Glu Ala Thr Pro Glu
    130                 135                 140

Glu Leu Leu His Gly His Ala His Gly Gly Gly Ser Arg Lys His His
145                 150                 155                 160

His His His His His His
                165

<210> SEQ ID NO 15
<211> LENGTH: 113
<212> TYPE: PRT
<213> ORGANISM: Artificial
<220> FEATURE:
<223> OTHER INFORMATION: TtSlyDcas

<400> SEQUENCE: 15

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Ala Gly Ser Gly Ser Ser Gly Lys Asp Leu Asp Phe Gln Val
65                  70                  75                  80

Glu Val Val Lys Val Arg Glu Ala Thr Pro Glu Glu Leu Leu His Gly
                85                  90                  95

His Ala His Gly Gly Gly Ser Arg Lys His His His His His His
              100                 105                 110

His

<210> SEQ ID NO 16
<211> LENGTH: 128
<212> TYPE: PRT
<213> ORGANISM: Artificial
<220> FEATURE:
<223> OTHER INFORMATION: TgSlyDdeltaIF

<400> SEQUENCE: 16

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Glu Lys Lys Glu Val Val Pro Pro Glu Lys
65              70                  75                  80

Gly Tyr Gly Ala Thr Gly His Pro Gly Ile Ile Pro Pro His Ala Thr
                85                  90                  95

Ala Ile Phe Glu Ile Glu Val Val Glu Ile Lys Lys Ala Gly Glu Ala
            100                 105                 110

Leu Glu His His His His His His Leu Glu His His His His His His
        115                 120                 125

<210> SEQ ID NO 17
<211> LENGTH: 133
<212> TYPE: PRT
<213> ORGANISM: Artificial
<220> FEATURE:
<223> OTHER INFORMATION: TtSlyDcas-Her3

<400> SEQUENCE: 17

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Ala Gly Ser Pro Gln Pro Leu Val Tyr Asn Lys Leu Thr Phe
65              70                  75                  80

Gln Leu Glu Pro Asn Pro His Thr Lys Gly Ser Ser Gly Lys Asp Leu
            85                  90                  95

Asp Phe Gln Val Glu Val Val Lys Val Arg Glu Ala Thr Pro Glu Glu
        100                 105                 110

Leu Leu His Gly His Ala His Gly Gly Gly Ser Arg Lys His His His
    115                 120                 125

His His His His His
    130

```
<210> SEQ ID NO 18
<211> LENGTH: 130
<212> TYPE: PRT
<213> ORGANISM: Artificial
<220> FEATURE:
<223> OTHER INFORMATION: TtSlyDcys-Her3

<400> SEQUENCE: 18

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro Cys Gly Pro Gln Pro Leu Val Tyr Asn Lys Leu Thr
65                  70                  75                  80

Phe Gln Leu Glu Pro Asn Pro His Thr Gly Cys Gly Lys Asp Leu Asp
                85                  90                  95

Phe Gln Val Glu Val Val Lys Val Arg Glu Ala Thr Pro Glu Glu Leu
            100                 105                 110

Leu His Gly His Ala His Gly Gly Gly Ser His His His His His His
        115                 120                 125

His His
    130

<210> SEQ ID NO 19
<211> LENGTH: 142
<212> TYPE: PRT
<213> ORGANISM: Artificial
<220> FEATURE:
<223> OTHER INFORMATION: TgSlyDser-Her3

<400> SEQUENCE: 19

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Lys Lys Glu Val Val Pro Pro Glu Lys
65                  70                  75                  80

Gly Tyr Gly Met Pro Ser Gly Pro Gln Pro Leu Val Tyr Asn Lys Leu
                85                  90                  95

Thr Phe Gln Leu Glu Pro Asn Pro His Thr Gly Ser Ala Gly Lys Thr
            100                 105                 110

Ala Ile Phe Glu Ile Glu Val Val Glu Ile Lys Lys Ala Gly Glu Ala
        115                 120                 125

Gly Gly Gly Ser Arg Lys His His His His His His His
    130                 135                 140

<210> SEQ ID NO 20
<211> LENGTH: 143
<212> TYPE: PRT
<213> ORGANISM: Artificial
```

```
<220> FEATURE:
<223> OTHER INFORMATION: TgSlyDcys-Her3

<400> SEQUENCE: 20

Met Arg Gly Ser Lys Val Glu Arg Gly Asp Phe Val Leu Phe Asn Tyr
1               5                   10                  15

Val Gly Arg Tyr Glu Asn Gly Glu Val Phe Asp Thr Ser Tyr Glu Ser
            20                  25                  30

Val Ala Arg Glu Gln Gly Ile Phe Val Glu Arg Gly Tyr Ser Pro
        35                  40                  45

Ile Gly Val Thr Val Gly Ala Gly Glu Ile Ile Pro Gly Ile Glu Glu
    50                  55                  60

Ala Leu Leu Gly Met Glu Leu Gly Lys Lys Glu Val Val Val Pro
65                  70                  75                  80

Pro Glu Lys Gly Tyr Gly Met Pro Cys Gly Pro Gln Pro Leu Val Tyr
                85                  90                  95

Asn Lys Leu Thr Phe Gln Leu Glu Pro Asn Pro His Thr Gly Cys Ala
            100                 105                 110

Gly Lys Thr Ala Ile Phe Glu Ile Glu Val Val Glu Ile Lys Lys Ala
        115                 120                 125

Gly Glu Ala Gly Gly Gly Ser His His His His His His His
    130                 135                 140

<210> SEQ ID NO 21
<211> LENGTH: 133
<212> TYPE: PRT
<213> ORGANISM: Artificial
<220> FEATURE:
<223> OTHER INFORMATION: TtSlyDcas-Her4

<400> SEQUENCE: 21

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Ala Gly Ser Pro Gln Thr Phe Val Tyr Asn Pro Thr Thr Phe
65                  70                  75                  80

Gln Leu Glu His Asn Phe Asn Ala Lys Gly Ser Ser Gly Lys Asp Leu
                85                  90                  95

Asp Phe Gln Val Glu Val Val Lys Val Arg Glu Ala Thr Pro Glu Glu
            100                 105                 110

Leu Leu His Gly His Ala His Gly Gly Gly Ser Arg Lys His His His
        115                 120                 125

His His His His His
    130

<210> SEQ ID NO 22
<211> LENGTH: 130
<212> TYPE: PRT
<213> ORGANISM: Artificial
<220> FEATURE:
<223> OTHER INFORMATION: TtSlyDcys-Her4
```

<400> SEQUENCE: 22

Met Arg Gly Ser Lys Val Gly Gln Asp Lys Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro Cys Gly Pro Gln Thr Phe Val Tyr Asn Pro Thr Thr
65                  70                  75                  80

Phe Gln Leu Glu His Asn Phe Asn Ala Gly Cys Gly Lys Asp Leu Asp
                85                  90                  95

Phe Gln Val Glu Val Val Lys Val Arg Glu Ala Thr Pro Glu Glu Leu
            100                 105                 110

Leu His Gly His Ala His Gly Gly Gly Ser His His His His His His
        115                 120                 125

His His
    130

<210> SEQ ID NO 23
<211> LENGTH: 142
<212> TYPE: PRT
<213> ORGANISM: Artificial
<220> FEATURE:
<223> OTHER INFORMATION: TgSlyDser-Her4

<400> SEQUENCE: 23

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Glu Lys Lys Glu Val Val Pro Pro Glu Lys
65                  70                  75                  80

Gly Tyr Gly Met Pro Ser Gly Pro Gln Thr Phe Val Tyr Asn Pro Thr
                85                  90                  95

Thr Phe Gln Leu Glu His Asn Phe Asn Ala Gly Ser Ala Gly Lys Thr
            100                 105                 110

Ala Ile Phe Glu Ile Glu Val Val Glu Ile Lys Lys Ala Gly Glu Ala
        115                 120                 125

Gly Gly Gly Ser Arg Lys His His His His His His His
    130                 135                 140

<210> SEQ ID NO 24
<211> LENGTH: 143
<212> TYPE: PRT
<213> ORGANISM: Artificial
<220> FEATURE:
<223> OTHER INFORMATION: TgSlyDcys-Her4

```
<400> SEQUENCE: 24

Met Arg Gly Ser Lys Val Glu Arg Gly Asp Phe Val Leu Phe Asn Tyr
1               5                   10                  15

Val Gly Arg Tyr Glu Asn Gly Glu Val Phe Asp Thr Ser Tyr Glu Ser
            20                  25                  30

Val Ala Arg Glu Gln Gly Ile Phe Val Glu Glu Arg Glu Tyr Ser Pro
        35                  40                  45

Ile Gly Val Thr Val Gly Ala Gly Glu Ile Ile Pro Gly Ile Glu Glu
    50                  55                  60

Ala Leu Leu Gly Met Glu Leu Gly Glu Lys Lys Glu Val Val Val Pro
65                  70                  75                  80

Pro Glu Lys Gly Tyr Gly Met Pro Cys Gly Pro Gln Thr Phe Val Tyr
                85                  90                  95

Asn Pro Thr Thr Phe Gln Leu Glu His Asn Phe Asn Ala Gly Cys Ala
            100                 105                 110

Gly Lys Thr Ala Ile Phe Glu Ile Glu Val Val Glu Ile Lys Lys Ala
        115                 120                 125

Gly Glu Ala Gly Gly Gly Ser His His His His His His His
    130                 135                 140

<210> SEQ ID NO 25
<211> LENGTH: 6
<212> TYPE: PRT
<213> ORGANISM: Mus musculus

<400> SEQUENCE: 25

Asp Tyr Trp Ile His Trp
1               5

<210> SEQ ID NO 26
<211> LENGTH: 16
<212> TYPE: PRT
<213> ORGANISM: Mus musculus

<400> SEQUENCE: 26

Ile Asn Pro Tyr Thr Gly Tyr Thr Glu Ser Asn Gln Lys Phe Lys Asp
1               5                   10                  15

<210> SEQ ID NO 27
<211> LENGTH: 7
<212> TYPE: PRT
<213> ORGANISM: Mus musculus

<400> SEQUENCE: 27

Pro Tyr Tyr Tyr Gly Asp Tyr
1               5

<210> SEQ ID NO 28
<211> LENGTH: 10
<212> TYPE: PRT
<213> ORGANISM: Mus musculus

<400> SEQUENCE: 28

Ser Ala Ser Ser Ser Val Ser Tyr Met His
1               5                   10

<210> SEQ ID NO 29
<211> LENGTH: 7
<212> TYPE: PRT
<213> ORGANISM: Mus musculus
```

```
<400> SEQUENCE: 29

Ser Thr Ser Asn Leu Ala Ser
1               5

<210> SEQ ID NO 30
<211> LENGTH: 9
<212> TYPE: PRT
<213> ORGANISM: Mus musculus

<400> SEQUENCE: 30

Gln Gln Arg Ser Ser Tyr Pro Phe Thr
1               5

<210> SEQ ID NO 31
<211> LENGTH: 116
<212> TYPE: PRT
<213> ORGANISM: Mus musculus

<400> SEQUENCE: 31

Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Thr Leu Thr Asp Tyr
                20                  25                  30

Trp Ile His Trp Val Lys Gln Arg Pro Gly Gln Gly Leu Glu Trp Ile
            35                  40                  45

Gly Tyr Ile Asn Pro Tyr Thr Gly Tyr Thr Glu Ser Asn Gln Lys Phe
        50                  55                  60

Lys Asp Lys Ala Thr Leu Thr Ala Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95

Ala Arg Pro Tyr Tyr Tyr Gly Asp Tyr Trp Gly Gln Gly Thr Thr Leu
                100                 105                 110

Thr Val Ser Ser
            115

<210> SEQ ID NO 32
<211> LENGTH: 106
<212> TYPE: PRT
<213> ORGANISM: Mus musculus

<400> SEQUENCE: 32

Gln Ile Val Leu Thr Gln Ser Pro Ala Ile Met Ser Ala Ser Pro Gly
1               5                   10                  15

Glu Arg Val Thr Ile Thr Cys Ser Ala Ser Ser Ser Val Ser Tyr Met
                20                  25                  30

His Trp Phe Gln Gln Lys Pro Gly Thr Ser Pro Lys Leu Leu Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
                100                 105
```

```
<210> SEQ ID NO 33
<211> LENGTH: 116
<212> TYPE: PRT
<213> ORGANISM: Artificial
<220> FEATURE:
<223> OTHER INFORMATION: humanized variant A of heavy chain variable
      domain VH of M-05-74 (VH-A)

<400> SEQUENCE: 33

Gln Val Gln Leu Val Gln Ser Gly Ala Glu Leu Lys Lys Pro Gly Ala
1               5                   10                  15

Ser Val Lys Val Ser Cys Arg Thr Ser Gly Tyr Thr Leu Thr Asp Tyr
                20                  25                  30

Trp Ile His Trp Val Arg Gln Ala Pro Gly Gln Gly Leu Glu Trp Met
            35                  40                  45

Gly Tyr Ile Asn Pro Tyr Thr Gly Tyr Thr Glu Ser Asn Gln Lys Phe
        50                  55                  60

Lys Asp Arg Val Ala Met Thr Arg Asp Ala Ser Ile Asn Thr Ala Tyr
65                  70                  75                  80

Met Glu Leu Thr Ser Leu Arg Ser Asp Asp Thr Ala Val Tyr Tyr Cys
                85                  90                  95

Ala Arg Pro Tyr Tyr Tyr Gly Asp Tyr Trp Gly Gln Gly Thr Leu Val
                100                 105                 110

Thr Val Ser Ser
        115

<210> SEQ ID NO 34
<211> LENGTH: 116
<212> TYPE: PRT
<213> ORGANISM: Artificial
<220> FEATURE:
<223> OTHER INFORMATION: humanized variant B of heavy chain variable
      domain VH of M-05-74 (VH-B)

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Leu Thr Asp Tyr
                20                  25                  30

Trp Ile His Trp Val Arg Gln Ala Pro Gly Gln Arg Leu Glu Trp Met
            35                  40                  45

Gly Tyr Ile Asn Pro Tyr Thr Gly Tyr Thr Glu Ser Asn Gln Lys Phe
        50                  55                  60

Lys Asp Arg Val Thr Ile Thr Arg Asp Thr Ser Ala Asn Thr Ala Tyr
65                  70                  75                  80

Met Ala Leu Ser Ser Leu Thr Ser Glu Asp Thr Ala Val Tyr Tyr Cys
                85                  90                  95

Ala Arg Pro Tyr Tyr Tyr Gly Asp Tyr Trp Gly Gln Gly Thr Leu Val
                100                 105                 110

Thr Val Ser Ser
        115

<210> SEQ ID NO 35
<211> LENGTH: 116
<212> TYPE: PRT
<213> ORGANISM: Artificial
<220> FEATURE:
<223> OTHER INFORMATION: humanized variant C of heavy chain variable
      domain VH of M-05-74 (VH-C)
```

```
<400> SEQUENCE: 35

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Thr Leu Thr Asp Tyr
            20                  25                  30

Trp Ile His Trp Val Arg Gln Ala Pro Gly Gln Gly Leu Glu Trp Met
        35                  40                  45

Gly Tyr Ile Asn Pro Tyr Thr Gly Tyr Thr Glu Ser Asn Gln Lys Phe
    50                  55                  60

Lys Asp Arg Val Thr Leu Ile Arg Asp Thr Ser Thr Thr Val Tyr
65                  70                  75                  80

Met Glu Leu Thr Ser Leu Thr Ser Glu Asp Thr Ala Val Tyr Tyr Cys
                85                  90                  95

Ala Arg Pro Tyr Tyr Tyr Gly Asp Tyr Trp Gly Gln Gly Thr Leu Val
            100                 105                 110

Thr Val Ser Ser
        115

<210> SEQ ID NO 36
<211> LENGTH: 116
<212> TYPE: PRT
<213> ORGANISM: Artificial
<220> FEATURE:
<223> OTHER INFORMATION: humanized variant D of heavy chain variable
      domain VH of M-05-74 (VH-D)

<400> SEQUENCE: 36

Gln Val Gln Leu Val Gln Ser Gly Gly Glu Leu Lys Lys Pro Gly Ala
1               5                   10                  15

Ser Val Lys Val Ser Cys Lys Ala Ser Gly Tyr Thr Leu Thr Asp Tyr
            20                  25                  30

Trp Ile His Trp Val Arg Gln Ala Pro Gly Gln Gly Leu Glu Trp Met
        35                  40                  45

Gly Tyr Ile Asn Pro Tyr Thr Gly Tyr Thr Glu Ser Asn Gln Lys Phe
    50                  55                  60

Lys Asp Arg Val Thr Met Thr Ala Asp Ala Ser Thr Gly Thr Ala Tyr
65                  70                  75                  80

Ile Glu Leu Arg Ser Leu Arg Ser Asp Asp Thr Ala Val Tyr Tyr Cys
                85                  90                  95

Ala Arg Pro Tyr Tyr Tyr Gly Asp Tyr Trp Gly Gln Gly Thr Leu Val
            100                 105                 110

Thr Val Ser Ser
        115

<210> SEQ ID NO 37
<211> LENGTH: 116
<212> TYPE: PRT
<213> ORGANISM: Artificial
<220> FEATURE:
<223> OTHER INFORMATION: humanized variant E of heavy chain variable
      domain VH of M-05-74 (VH-E)

<400> SEQUENCE: 37

Gln Val Gln Leu Val Gln Ser Gly Val Glu Val Lys Lys Pro Gly Ala
1               5                   10                  15

Ser Val Lys Val Ser Cys Lys Thr Ser Gly Tyr Thr Leu Thr Asp Tyr
            20                  25                  30
```

-continued

```
Trp Ile His Trp Val Arg Gln Ala Pro Gly Gln Gly Leu Glu Trp Met
            35                  40                  45

Gly Tyr Ile Asn Pro Tyr Thr Gly Tyr Thr Glu Ser Asn Gln Lys Phe
 50                  55                  60

Lys Asp Arg Val Thr Met Thr Ser Asp Thr Ser Ile Asp Thr Ala Tyr
 65                  70                  75                  80

Met Glu Leu Thr Arg Leu Arg Ser Asp Asp Thr Ala Val Tyr Tyr Cys
                85                  90                  95

Ala Arg Pro Tyr Tyr Tyr Gly Asp Tyr Trp Gly Gln Gly Thr Thr Val
            100                 105                 110

Thr Val Ser Ser
        115

<210> SEQ ID NO 38
<211> LENGTH: 106
<212> TYPE: PRT
<213> ORGANISM: Artificial
<220> FEATURE:
<223> OTHER INFORMATION: humanized variant A of light chain variable
      domain VL of M-05-74 (VL-A)

<400> SEQUENCE: 38

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Tyr Met
                20                  25                  30

His Trp Tyr Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Arg Ser Ser Tyr Pro Phe Thr
                85                  90                  95

Phe Gly Gln Gly Thr Lys Leu Glu Ile Lys
            100                 105

<210> SEQ ID NO 39
<211> LENGTH: 106
<212> TYPE: PRT
<213> ORGANISM: Artificial
<220> FEATURE:
<223> OTHER INFORMATION: humanized variant B of light chain variable
      domain VL of M-05-74 (VL-B)

<400> SEQUENCE: 39

Glu Ile Val Leu Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
                20                  25                  30

His Trp Tyr Gln Gln Lys Pro Gly Lys Ala Pro Lys Leu Leu Ile Tyr
            35                  40                  45

Ser Thr Ser Asn Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80
```

```
Asp Phe Ala Thr Tyr Tyr Cys Gln Gln Arg Ser Ser Tyr Pro Phe Thr
                85                  90                  95

Phe Gly Gly Gly Thr Lys Val Asp Ile Lys
            100                 105

<210> SEQ ID NO 40
<211> LENGTH: 106
<212> TYPE: PRT
<213> ORGANISM: Artificial
<220> FEATURE:
<223> OTHER INFORMATION: humanized variant C of light chain variable
      domain VL of M-05-74 (VL-C)

<400> SEQUENCE: 40

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Phe Gln Gln Lys Pro Gly Lys Ala Pro Lys Ser Leu Ile Tyr
            35                  40                  45

Ser Thr Ser Asn Leu Ala Ser Gly Val Pro Ser Lys Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Ser Ser Tyr Pro Phe Thr
                85                  90                  95

Phe Gly Gln Gly Thr Lys Leu Glu Ile Lys
            100                 105

<210> SEQ ID NO 41
<211> LENGTH: 106
<212> TYPE: PRT
<213> ORGANISM: Artificial
<220> FEATURE:
<223> OTHER INFORMATION: humanized variant D of light chain variable
      domain VL of M-05-74 (VL-D)

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Phe Gln Gln Lys Pro Gly Gln Pro Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Gly Gly Thr Lys Val Glu Ile Lys
            100                 105

<210> SEQ ID NO 42
<211> LENGTH: 106
<212> TYPE: PRT
<213> ORGANISM: Artificial
<220> FEATURE:
<223> OTHER INFORMATION: humanized variant E of light chain variable
      domain VL of M-05-74 (VL-E)
```

```
<400> SEQUENCE: 42

Glu Ile Val Met Thr Gln Ser Pro Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Arg Ser Ser Tyr Pro Phe Thr
                85                  90                  95

Phe Gly Gln Gly Thr Lys Leu Glu Ile Lys
            100                 105

<210> SEQ ID NO 43
<211> LENGTH: 11
<212> TYPE: PRT
<213> ORGANISM: Homo Sapiens

<400> SEQUENCE: 43

Val Tyr Asn Lys Leu Thr Phe Gln Leu Glu Pro
1               5                   10

<210> SEQ ID NO 44
<211> LENGTH: 10
<212> TYPE: PRT
<213> ORGANISM: Homo Sapiens

<400> SEQUENCE: 44

Val Tyr Asn Pro Thr Thr Phe Gln Leu Glu
1               5                   10

<210> SEQ ID NO 45
<211> LENGTH: 234
<212> TYPE: PRT
<213> ORGANISM: Artificial
<220> FEATURE:
<223> OTHER INFORMATION: Pseudomonas exotoxin variant PE24LR8M_3G
      (including a GGG linker)

<400> SEQUENCE: 45

Met Gly Gly Gly Arg His Arg Gln Pro Arg Gly Trp Glu Gln Leu Tyr
1               5                   10                  15

Pro Thr Gly Ala Glu Phe Leu Gly Asp Gly Gly Ala Val Ser Phe Ser
            20                  25                  30

Thr Arg Gly Thr Gln Asn Trp Thr Val Glu Arg Leu Leu Gln Ala His
        35                  40                  45

Arg Gln Leu Glu Glu Gly Gly Tyr Val Phe Val Gly Tyr His Gly Thr
    50                  55                  60

Phe Leu Glu Ala Ala Gln Ser Ile Val Phe Gly Gly Val Arg Ala Arg
65                  70                  75                  80

Ser Gln Asp Leu Asp Ala Ile Trp Ala Gly Phe Tyr Ile Ala Gly Asp
                85                  90                  95

Pro Ala Leu Ala Tyr Gly Tyr Ala Gln Asp Gln Glu Pro Asp Ala Ala
            100                 105                 110

Gly Arg Ile Arg Asn Gly Ala Leu Leu Arg Val Tyr Val Pro Arg Ser
        115                 120                 125
```

```
Ser Leu Pro Gly Phe Tyr Ala Thr Ser Leu Thr Leu Ala Ala Pro Glu
    130                 135                 140

Ala Ala Gly Glu Val Glu Arg Leu Ile Gly His Pro Leu Pro Leu Arg
145                 150                 155                 160

Leu Asp Ala Ile Thr Gly Pro Glu Ser Gly Gly Arg Leu Glu Thr
                    165                 170                 175

Ile Leu Gly Trp Pro Leu Ala Glu Arg Thr Val Val Ile Pro Ser Ala
            180                 185                 190

Ile Pro Thr Asp Pro Arg Asn Val Gly Gly Asp Leu Asp Pro Ser Ser
                195                 200                 205

Ile Pro Asp Ser Glu Ala Ala Ile Ser Ala Leu Pro Asp Tyr Ala Ser
        210                 215                 220

Gln Pro Gly Lys Pro Pro Arg Glu Asp Leu
225                 230
```

<210> SEQ ID NO 46
<211> LENGTH: 213
<212> TYPE: PRT
<213> ORGANISM: Artificial
<220> FEATURE:
<223> OTHER INFORMATION: Light chain of M-05-74 (M-05-74_LC)

<400> SEQUENCE: 46

```
Gln Ile Val Leu Thr Gln Ser Pro Ala Ile Met Ser Ala Ser Pro Gly
1               5                   10                  15

Glu Arg Val Thr Ile Thr Cys Ser Ala Ser Ser Val Ser Tyr Met
                20                  25                  30

His Trp Phe Gln Gln Lys Pro Gly Thr Ser Pro Lys Leu Leu Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 47
<211> LENGTH: 238
<212> TYPE: PRT
<213> ORGANISM: Artificial

<220> FEATURE:
<223> OTHER INFORMATION: Heavy chain of M-05-74 HC with sortase tag
      (M-05-74_HC)

<400> SEQUENCE: 47

```
Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Thr Leu Thr Asp Tyr
            20                  25                  30

Trp Ile His Trp Val Lys Gln Arg Pro Gly Gln Gly Leu Glu Trp Ile
        35                  40                  45

Gly Tyr Ile Asn Pro Tyr Thr Gly Tyr Thr Glu Ser Asn Gln Lys Phe
    50                  55                  60

Lys Asp Lys Ala Thr Leu Thr Ala Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95

Ala Arg Pro Tyr Tyr Tyr Gly Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Ser Leu
    210                 215                 220

Pro Glu Thr Gly Gly Ser Gly Ser His His His His His
225                 230                 235
```

<210> SEQ ID NO 48
<211> LENGTH: 460
<212> TYPE: PRT
<213> ORGANISM: Artificial
<220> FEATURE:
<223> OTHER INFORMATION: Heavy chain of M-05-74 HC conjugated to
      Pseudomonas exotoxin variant PE24LR8M (Fab-074-PE heavy chain 1)

<400> SEQUENCE: 48

```
Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Thr Leu Thr Asp Tyr
            20                  25                  30

Trp Ile His Trp Val Lys Gln Arg Pro Gly Gln Gly Leu Glu Trp Ile
        35                  40                  45

Gly Tyr Ile Asn Pro Tyr Thr Gly Tyr Thr Glu Ser Asn Gln Lys Phe
    50                  55                  60

Lys Asp Lys Ala Thr Leu Thr Ala Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95
```

Ala Arg Pro Tyr Tyr Tyr Gly Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Ser Leu
    210                 215                 220

Pro Glu Thr Gly Gly Gly Arg His Arg Gln Pro Arg Gly Trp Glu Gln
225                 230                 235                 240

Leu Tyr Pro Thr Gly Ala Glu Phe Leu Gly Asp Gly Gly Ala Val Ser
                245                 250                 255

Phe Ser Thr Arg Gly Thr Gln Asn Trp Thr Val Glu Arg Leu Leu Gln
            260                 265                 270

Ala His Arg Gln Leu Glu Glu Gly Tyr Val Phe Val Gly Tyr His
        275                 280                 285

Gly Thr Phe Leu Glu Ala Ala Gln Ser Ile Val Phe Gly Gly Val Arg
    290                 295                 300

Ala Arg Ser Gln Asp Leu Asp Ala Ile Trp Ala Gly Phe Tyr Ile Ala
305                 310                 315                 320

Gly Asp Pro Ala Leu Ala Tyr Gly Tyr Ala Gln Asp Gln Glu Pro Asp
                325                 330                 335

Ala Ala Gly Arg Ile Arg Asn Gly Ala Leu Leu Arg Val Tyr Val Pro
            340                 345                 350

Arg Ser Ser Leu Pro Gly Phe Tyr Ala Thr Ser Leu Thr Leu Ala Ala
        355                 360                 365

Pro Glu Ala Ala Gly Glu Val Glu Arg Leu Ile Gly His Pro Leu Pro
    370                 375                 380

Leu Arg Leu Asp Ala Ile Thr Gly Pro Glu Glu Ser Gly Gly Arg Leu
385                 390                 395                 400

Glu Thr Ile Leu Gly Trp Pro Leu Ala Glu Arg Thr Val Val Ile Pro
                405                 410                 415

Ser Ala Ile Pro Thr Asp Pro Arg Asn Val Gly Gly Asp Leu Asp Pro
            420                 425                 430

Ser Ser Ile Pro Asp Ser Glu Ala Ala Ile Ser Ala Leu Pro Asp Tyr
        435                 440                 445

Ala Ser Gln Pro Gly Lys Pro Pro Arg Glu Asp Leu
    450                 455                 460

<210> SEQ ID NO 49
<211> LENGTH: 457
<212> TYPE: PRT
<213> ORGANISM: Artificial
<220> FEATURE:
<223> OTHER INFORMATION: Heavy chain of M-05-74 HC conjugated to
      Pseudomonas exotoxin variant PE24LR8M (Fab-074-PE heavy chain 2)
      as direct PE24LR8M fusion

```
<400> SEQUENCE: 49

Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Thr Leu Thr Asp Tyr
            20                  25                  30

Trp Ile His Trp Val Lys Gln Arg Pro Gly Gln Gly Leu Glu Trp Ile
        35                  40                  45

Gly Tyr Ile Asn Pro Tyr Thr Gly Tyr Thr Glu Ser Asn Gln Lys Phe
    50                  55                  60

Lys Asp Lys Ala Thr Leu Thr Ala Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95

Ala Arg Pro Tyr Tyr Gly Asp Tyr Trp Gly Gln Gly Thr Thr Leu
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Val Glu Pro Lys Ser Cys Lys Ala Ser Gly Gly
210                 215                 220

Arg His Arg Gln Pro Arg Gly Trp Glu Gln Leu Gly Gly Ser Pro Thr
225                 230                 235                 240

Gly Ala Glu Phe Leu Gly Asp Gly Gly Ala Val Ser Phe Ser Thr Arg
                245                 250                 255

Gly Thr Gln Asn Trp Thr Val Glu Arg Leu Leu Gln Ala His Arg Gln
            260                 265                 270

Leu Glu Glu Gly Gly Tyr Val Phe Val Gly Tyr His Gly Thr Phe Leu
            275                 280                 285

Glu Ala Ala Gln Ser Ile Val Phe Gly Val Arg Ala Arg Ser Gln
290                 295                 300

Asp Leu Asp Ala Ile Trp Ala Gly Phe Tyr Ile Ala Gly Asp Pro Ala
305                 310                 315                 320

Leu Ala Tyr Gly Tyr Ala Gln Asp Gln Glu Pro Asp Ala Ala Gly Arg
                325                 330                 335

Ile Arg Asn Gly Ala Leu Leu Arg Val Tyr Val Pro Arg Ser Ser Leu
            340                 345                 350

Pro Gly Phe Tyr Ala Thr Ser Leu Thr Leu Ala Ala Pro Glu Ala Ala
            355                 360                 365

Gly Glu Val Glu Arg Leu Ile Gly His Pro Leu Pro Leu Arg Leu Asp
370                 375                 380

Ala Ile Thr Gly Pro Glu Glu Ser Gly Gly Arg Leu Glu Thr Ile Leu
385                 390                 395                 400

Gly Trp Pro Leu Ala Glu Arg Thr Val Val Ile Pro Ser Ala Ile Pro
                405                 410                 415
```

```
Thr Asp Pro Arg Asn Val Gly Gly Asp Leu Asp Pro Ser Ser Ile Pro
            420                 425                 430

Asp Ser Glu Ala Ala Ile Ser Ala Leu Pro Asp Tyr Ala Ser Gln Pro
            435                 440                 445

Gly Lys Pro Pro Arg Glu Asp Leu Lys
        450                 455

<210> SEQ ID NO 50
<211> LENGTH: 147
<212> TYPE: PRT
<213> ORGANISM: Staphylococcus aureus

<400> SEQUENCE: 50

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Asn
        35                  40                  45

Glu Ser Leu Asp Asp Gln Asn Ile Ser Ile Ala Gly His Thr Phe Ile
 50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
130                 135                 140

Glu Val Lys
145

<210> SEQ ID NO 51
<211> LENGTH: 119
<212> TYPE: PRT
<213> ORGANISM: Mus musculus

<400> SEQUENCE: 51

Gln Ala Tyr Leu Gln Gln Ser Gly Ala Glu Leu Met Arg Pro Gly Ala
1               5                   10                  15

Ser Val Arg Met Ser Cys Gln Ala Ser Gly Tyr Thr Phe Thr Ser Tyr
            20                  25                  30

Thr Ile His Trp Leu Lys Gln Thr Pro Arg Gln Gly Leu Glu Trp Ile
        35                  40                  45

Gly Ala Ile Tyr Pro Arg Asn Gly Asp Phe Ser Tyr Asn Gln Lys Phe
 50                  55                  60

Lys Asp Lys Ala Ser Leu Thr Val Asp Thr Ser Ser Thr Ala Tyr
65                  70                  75                  80

Met His Leu Ser Ser Leu Thr Ser Glu Asp Ser Ala Val Tyr Phe Cys
                85                  90                  95

Ala Arg Thr Ile Asn Tyr Gly Asp Trp Phe Ala Tyr Trp Gly Gln Gly
            100                 105                 110

Thr Leu Val Thr Val Ser Ala
        115
```

-continued

```
<210> SEQ ID NO 52
<211> LENGTH: 107
<212> TYPE: PRT
<213> ORGANISM: Mus musculus

<400> SEQUENCE: 52

Asp Ile Gln Met Ile Gln Ser Pro Ala Ser Leu Phe Val Ser Glu Gly
1               5                   10                  15

Glu Thr Val Ile Ile Thr Cys Arg Ala Ser Glu Asn Ile Tyr Ser Asn
            20                  25                  30

Leu Ala Trp Tyr His Gln Lys Lys Gly Lys Ser Pro Gln Val Leu Val
        35                  40                  45

Tyr Ala Ala Ile Lys Leu Ala Asp Gly Val Pro Leu Arg Phe Ser Gly
    50                  55                  60

Ser Gly Ser Gly Thr Gln Phe Ser Leu Lys Ile Asn Ser Leu Gln Ser
65                  70                  75                  80

Glu Asp Phe Gly Ser Tyr Tyr Cys Gln His Phe Trp Gly Pro Pro Tyr
                85                  90                  95

Thr Phe Gly Ser Gly Thr Asn Leu Glu Ile Lys
            100                 105

<210> SEQ ID NO 53
<211> LENGTH: 107
<212> TYPE: PRT
<213> ORGANISM: Homo Sapiens

<400> SEQUENCE: 53

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 54
<211> LENGTH: 105
<212> TYPE: PRT
<213> ORGANISM: Homo Sapiens

<400> SEQUENCE: 54

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80
```

-continued

His Arg Ser Tyr Ser Cys Gln Val Thr His Glu Gly Ser Thr Val Glu
            85                  90                  95

Lys Thr Val Ala Pro Thr Glu Cys Ser
100                 105

<210> SEQ ID NO 55
<211> LENGTH: 330
<212> TYPE: PRT
<213> ORGANISM: Homo Sapiens

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 56
<211> LENGTH: 330
<212> TYPE: PRT
<213> ORGANISM: homo sapiens

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 330
<212> TYPE: PRT
<213> ORGANISM: homo sapiens

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 58
<211> LENGTH: 327
<212> TYPE: PRT
<213> ORGANISM: Homo Sapiens

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 59
<211> LENGTH: 157
<212> TYPE: PRT
<213> ORGANISM: Homo sapiens

<400> SEQUENCE: 59

Arg Ser Arg Ala Cys His Pro Cys Ser Pro Met Cys Lys Gly Ser Arg
1               5                   10                  15

Cys Trp Gly Glu Ser Ser Glu Asp Cys Gln Ser Leu Thr Arg Thr Val
            20                  25                  30

Cys Ala Gly Gly Cys Ala Arg Cys Lys Gly Pro Leu Pro Thr Asp Cys
        35                  40                  45

Cys His Glu Gln Cys Ala Ala Gly Cys Thr Gly Pro Lys His Ser Asp
    50                  55                  60
```

```
Cys Leu Ala Cys Leu His Phe Asn His Ser Gly Ile Cys Glu Leu His
 65                  70                  75                  80

Cys Pro Ala Leu Val Thr Tyr Asn Thr Asp Thr Phe Glu Ser Met Pro
                 85                  90                  95

Asn Pro Glu Gly Arg Tyr Thr Phe Gly Ala Ser Cys Val Thr Ala Cys
            100                 105                 110

Pro Tyr Asn Tyr Leu Ser Thr Asp Val Gly Ser Cys Thr Leu Val Cys
        115                 120                 125

Pro Leu His Asn Gln Glu Val Thr Ala Glu Asp Gly Thr Gln Arg Cys
    130                 135                 140

Glu Lys Cys Ser Lys Pro Cys Ala Arg Val Cys Tyr Gly
145                 150                 155

<210> SEQ ID NO 60
<211> LENGTH: 5
<212> TYPE: PRT
<213> ORGANISM: Artificial
<220> FEATURE:
<223> OTHER INFORMATION: heavy chain HVR-H1, pertuzumab

<400> SEQUENCE: 60

Asp Tyr Thr Met Asp
1               5

<210> SEQ ID NO 61
<211> LENGTH: 17
<212> TYPE: PRT
<213> ORGANISM: Artificial
<220> FEATURE:
<223> OTHER INFORMATION: heavy chain HVR-H2 pertuzumab

<400> SEQUENCE: 61

Asp Val Asn Pro Asn Ser Gly Gly Ser Ile Tyr Asn Gln Arg Phe Lys
1               5                   10                  15

Gly

<210> SEQ ID NO 62
<211> LENGTH: 10
<212> TYPE: PRT
<213> ORGANISM: Artificial
<220> FEATURE:
<223> OTHER INFORMATION: heavy chain HVR-H3, pertuzumab

<400> SEQUENCE: 62

Asn Leu Gly Pro Ser Phe Tyr Phe Asp Tyr
1               5                   10

<210> SEQ ID NO 63
<211> LENGTH: 11
<212> TYPE: PRT
<213> ORGANISM: Artificial
<220> FEATURE:
<223> OTHER INFORMATION: light chain HVR-L1, pertuzumab

<400> SEQUENCE: 63

Lys Ala Ser Gln Asp Val Ser Ile Gly Val Ala
1               5                   10

<210> SEQ ID NO 64
<211> LENGTH: 7
<212> TYPE: PRT
<213> ORGANISM: Artificial
<220> FEATURE:
<223> OTHER INFORMATION: light chain HVR-L2, pertuzumab
```

```
<400> SEQUENCE: 64

Ser Ala Ser Tyr Arg Tyr Thr
1               5

<210> SEQ ID NO 65
<211> LENGTH: 9
<212> TYPE: PRT
<213> ORGANISM: Artificial
<220> FEATURE:
<223> OTHER INFORMATION: light chain HVR-L3 pertuzumab

<400> SEQUENCE: 65

Gln Gln Tyr Tyr Ile Tyr Pro Tyr Thr
1               5

<210> SEQ ID NO 66
<211> LENGTH: 119
<212> TYPE: PRT
<213> ORGANISM: Artificial
<220> FEATURE:
<223> OTHER INFORMATION: heavy chain variable domain VH, pertuzumab

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 67
<211> LENGTH: 107
<212> TYPE: PRT
<213> ORGANISM: Artificial
<220> FEATURE:
<223> OTHER INFORMATION: light chain variable domain VL, pertuzumab

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 68
<211> LENGTH: 453
<212> TYPE: PRT
<213> ORGANISM: Artificial
<220> FEATURE:
<223> OTHER INFORMATION: heavy chain 1, bispecific HER3/HER2 antibody
      DIBxPERT

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
210                 215                 220

Glu Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

```
Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
            355                 360                 365

Val Ser Leu Ser Cys Ala Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 69
<211> LENGTH: 212
<212> TYPE: PRT
<213> ORGANISM: Artificial
<220> FEATURE:
<223> OTHER INFORMATION: light chain 1, bispecific HER3/HER2 antibody
      DIBxPERT

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
            85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
            165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
            195                 200                 205

Pro Lys Ser Cys
            210
```

<210> SEQ ID NO 70
<211> LENGTH: 446
<212> TYPE: PRT
<213> ORGANISM: Artificial
<220> FEATURE:
<223> OTHER INFORMATION: heavy chain 2, bispecific HER3/HER2 antibody DIBxPERT

<400> SEQUENCE: 70

```
Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Thr Leu Thr Asp Tyr
            20                  25                  30

Trp Ile His Trp Val Lys Gln Arg Pro Gly Gln Gly Leu Glu Trp Ile
        35                  40                  45

Gly Tyr Ile Asn Pro Tyr Thr Gly Tyr Thr Glu Ser Asn Gln Lys Phe
    50                  55                  60

Lys Asp Lys Ala Thr Leu Thr Ala Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95

Ala Arg Pro Tyr Tyr Tyr Gly Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365
```

```
Lys Gly Phe Tyr Pro Ser Asp Ile Ala Val Glu Trp Glu Ser Asn Gly
    370             375             380
Gln Pro Glu Asn Asn Tyr Lys Thr Thr Pro Pro Val Leu Asp Ser Asp
385             390             395             400
Gly Ser Phe Phe Leu Tyr Ser Lys Leu Thr Val Asp Lys Ser Arg Trp
            405             410             415
Gln Gln Gly Asn Val Phe Ser Cys Ser Val Met His Glu Ala Leu His
            420             425             430
Asn His Tyr Thr Gln Lys Ser Leu Ser Leu Ser Pro Gly Lys
            435             440             445

<210> SEQ ID NO 71
<211> LENGTH: 213
<212> TYPE: PRT
<213> ORGANISM: Artificial
<220> FEATURE:
<223> OTHER INFORMATION: light chain 2, bispecific HER3/HER2 antibody
      DIBxPERT

<400> SEQUENCE: 71

Gln Ile Val Leu Thr Gln Ser Pro Ala Ile Met Ser Ala Ser Pro Gly
1               5               10              15
Glu Arg Val Thr Ile Thr Cys Ser Ala Ser Ser Ser Val Ser Tyr Met
                20              25              30
His Trp Phe Gln Gln Lys Pro Gly Thr Ser Pro Lys Leu Leu Ile Tyr
            35              40              45
Ser Thr Ser Asn Leu Ala Ser Gly Val Pro Ala Arg Phe Ser Gly Ser
        50              55              60
Gly Ser Gly Thr Ser Tyr Ser Leu Thr Ile Ser Arg Met Glu Ala Glu
65              70              75              80
Asp Ala Ala Thr Tyr Tyr Cys Gln Gln Arg Ser Ser Tyr Pro Phe Thr
                85              90              95
Phe Gly Ser Gly Thr Lys Leu Glu Ile Lys Arg Thr Val Ala Ala Pro
            100             105             110
Ser Val Phe Ile Phe Pro Pro Ser Asp Glu Gln Leu Lys Ser Gly Thr
        115             120             125
Ala Ser Val Val Cys Leu Leu Asn Asn Phe Tyr Pro Arg Glu Ala Lys
    130             135             140
Val Gln Trp Lys Val Asp Asn Ala Leu Gln Ser Gly Asn Ser Gln Glu
145             150             155             160
Ser Val Thr Glu Gln Asp Ser Lys Asp Ser Thr Tyr Ser Leu Ser Ser
                165             170             175
Thr Leu Thr Leu Ser Lys Ala Asp Tyr Glu Lys His Lys Val Tyr Ala
            180             185             190
Cys Glu Val Thr His Gln Gly Leu Ser Ser Pro Val Thr Lys Ser Phe
            195             200             205
Asn Arg Gly Glu Cys
    210
```

HER3/HER2 BISPECIFIC ANTIBODIES BINDING TO THE BETA-HAIRPIN OF HER3 AND DOMAIN II OF HER2

CROSS REFERENCE TO RELATED APPLICATIONS

This application is a continuation of PCT/EP2015/060488 filed on May 12, 2015, publication number WO2015/173248, which claims priority to European Patent Application No. EP14168323.5 filed on May 14, 2014, the disclosures of which are all incorporated herein by reference in their entirety.

SEQUENCE LISTING

The present application contains a Sequence Listing which has been submitted in ASCII format via EFS-Web and is hereby incorporated by reference in its entirety. Said ASCII copy, created on Nov. 10, 2016, is named P32126 US_ST25.txt and is 146,013 bytes in size.

FIELD OF THE INVENTION

The invention relates to HER3/HER2 bispecific antibodies, that bind to the beta-hairpin of HER3 and domain II of HER2, their preparation and use as medicament.

BACKGROUND OF THE INVENTION

The HER protein family consists of 4 members: HER1, also named epidermal growth factor receptor (EGFR) or ErbB-1, HER2, also named ErbB-2, ErbB-3, also named HER3 and ErbB-4, also named HER4. The ErbB family proteins are receptor tyrosine kinases and represent important mediators of cell growth, differentiation and survival. The HER family represent receptors proteins of different ligands like the neuregulin (NRG) family, amphiregulin, EGF and (TGF-a). Heregulin (also called HRG or neuregulin NRG-1) is e.g. a ligand for HER3 and HER4.

Human HER3 (ErbB-3, ERBB3, c-erbB-3, c-erbB3, receptor tyrosine-protein kinase erbB-3, SEQ ID NO: 3) encodes a member of the epidermal growth factor receptor (EGFR) family of receptor tyrosine kinases which also includes HER1 (also known as EGFR), HER2, and HER4 (Kraus, M. H. et al, PNAS 86 (1989) 9193-9197; Plowman, G. D. et al, PNAS 87 (1990) 4905-4909; Kraus, M. H. et al, PNAS 90 (1993) 2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This membrane-bound protein has a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski M. X., et al, J. Biol. Chem. 269 (1994) 14661-14665; Alimandi M, et al, Oncogene. 10 (1995) 1813-1821; Hellyer, N.J., J. Biol. Chem. 276 (2001) 42153-4261; Singer, E., J. Biol. Chem. 276 (2001) 44266-44274; Schaefer, K. L., Neoplasia 8 (2006) 613-622) For an overview of HER3 and its various interactions within the HER receptor family and the NGR ligands family see e.g. G Sithanandam et al Cancer Gene Therapy (2008) 15, 413-448.

Amplification of this gene and/or overexpression of its protein have been reported in numerous cancers, including prostate, bladder, and breast tumors. Alternate transcriptional splice variants encoding different isoforms have been characterized. One isoform lacks the intermembrane region and is secreted outside the cell. This form acts to modulate the activity of the membrane-bound form. Additional splice variants have also been reported, but they have not been thoroughly characterized.

Interestingly in its equilibrium state, the HER3 receptor exists in its "closed confirmation", which does mean, the heterodimerization HER3beta-hairpin motive is tethered via non-covalent interactions to the HER3ECD domain IV (see FIGS. 1c and 1d). It is supposed, that the "closed" HER3 conformation can be opened via the binding of the ligand heregulin at a specific HER3 heregulin binding site. This takes place at the HER3 interface formed by the HER3 ECD domains I and domain III. By this interaction it is believed, that the HER3 receptor is activated and transferred into its "open conformation" (see FIGS. 1e and 1b and e.g. Baselga, J. et al, Nat Rev Cancer 9 (2009). 463-475 and Desbois-Mouthon, C., et al, Gastroenterol Clin Biol 34 (2010) 255-259). In this open conformation heterodimerization and transignal induction with HER2 is possible (see FIG. 1b).

WO 2003/013602 relates to inhibitors of HER activity, including HER antibodies. WO 2007/077028 and WO 2008/100624 also relate to HER3 antibodies.

WO 97/35885 and WO2010/127181 relate to HER3 antibodies.

Human HER4 (also known as ErbB-4 ERBB4, v-erb-a erythroblastic leukemia viral oncogene homolog 4, p180erbB4 avian erythroblastic leukemia viral (v-erb-b2) oncogene homolog 4; SEQ ID NO:5) is a single-pass type I transmembrane protein with multiple furin-like cysteine rich domains, a tyrosine kinase domain, a phosphotidylinositol-3 kinase binding site and a PDZ domain binding motif (Plowman G D, wt al, PNAS 90:1746-50(1993); Zimonjic D B, et al, Oncogene 10:1235-7(1995); Culouscou J M, et al, J. Biol. Chem. 268:18407-10(1993)). The protein binds to and is activated by neuregulins-2 and -3, heparin-binding EGF-like growth factor and betacellulin. Ligand binding induces a variety of cellular responses including mitogenesis and differentiation. Multiple proteolytic events allow for the release of a cytoplasmic fragment and an extracellular fragment. Mutations in this gene have been associated with cancer. Alternatively spliced variants which encode different protein isoforms have been described; however, not all variants have been fully characterized.

Anti-HER4 antibodies for use in anti-cancer therapy are known e.g. from U.S. Pat. Nos. 5,811,098, 7,332,579 or Hollmén M, et al, Oncogene. 28 (2009) 1309-19 (anti-ErbB-4 antibody mAb 1479).

So far it was not possible to select antibodies that specifically bind to the beta-hairpin of HER3 (and/or HER4) as these beta-hairpins of HER3 (or of HER4) both represent hidden epitopes, which are not accessible in the equilibrium state of these receptors (see FIG. 1).

Human HER2 is a transmembrane surface-bound receptor tyrosine kinase and is normally involved in the signal transduction pathways leading to cell growth and differentiation. HER2 is a promising target for treatment of breast cancer as it was found to be overexpressed in about one-quarter of breast cancer patients (Bange et al, 2001, Nature Medicine 7:548). HER2 an oncogene and overexpression or mutation of this receptor lead to its constitutive activation. This drives the formation of various cancers, like breast, oral, pancreas and lung carcinoma (Schneider et al. 1989, Weiner et al. 1990, Hou et al. 1992, Revillion et al. 1998). HER2 is the only receptor of the HER family, which is not expressed in the tethered conformation like HER1, HER3 and HER4 are. Instead it is expressed in an open, extended conformation on the cell surface. In this conformation the β-hairpin of subdomain II is accessible. The antibody Pertuzumab (Perjeta®) was shown to bind immediate to the HER2 extracellular domain (ECD) β-hairpin and surrounding region in subdomain II. The β-hairpin is essential for the formation of dimers with other HER receptors. By binding to this epitope, Pertuzumab is able to inhibit dimer formation and therefore the activation of subsequent signaling cascades.

The HER2/HER3 heterodimer induces one of the most important mitogenic signals via the PI3K and AKT pathway among HER family members (Sliwkowski M. X., et al, J. Biol. Chem. 269 (1994) 14661-14665; Alimandi M, et al, Oncogene. 10 (1995) 1813-1821; Hellyer, N.J., J. Biol. Chem. 276 (2001) 42153-4261; Singer, E., J. Biol. Chem. 276 (2001) 44266-44274; Schaefer, K. L., Neoplasia 8 (2006) 613-622). Especially the formation of HRG1β induced HER2/HER3 heterodimers plays a pivotal role in cancers with autocrine HRG loops (Gollamudi et al. 2004). Additionally, the results of current clinical studies indicate, that success of anti-HER2 antibody treatments is reduced in presence of HRG1β (McDonagh et al. 2012). Pertuzumab (rhuMab 2C4, U.S. Pat. No. 7,862,817, marketed e.g as PERJETA™) is a humanized monoclonal antibody, which is designed specifically to prevent the HER2 receptor from pairing (dimerising) with other HER receptors (EGFR/HER1, HER3 and HER4) on the surface of cells, a process that is believed to play a role in tumor growth and survival. Pertuzumab binds to domain II of HER2, essential for dimerization. Pertuzumab binds specifically to the 2C4 epitope, a different epitope on the extracellular domain of HER2 as trastuzumab. Pertuzumab is the first in a new class of HER dimerisation inhibitors (HDIs). Through its binding to the HER2 extracellular domain, pertuzumab blocks ligand-activated heterodimerisation of HER2 with other HER family members, thereby inhibiting downstream signalling pathways and cellular processes associated with tumor growth and progression (Franklin, M. C., et al. Cancer Cell 5 (2004) 317-328 and Friess, T, et al. Clin Cancer Res 11 (2005) 5300-5309). Pertuzumab is a recombinant humanized version of the murine anti-HER2 antibody 2C4 (referred to as rhuMAb 2C4 or pertuzumab) and it is described together with the respective method of preparation in WO 01/00245 and WO 2006/007398.

SUMMARY OF THE INVENTION

The present invention relates to bispecific antibodies which bind to the beta-hairpin of human HER3 (SEQ ID NO: 1) and domain II of human HER2 (SEQ ID NO: 59). Both domains are responsible for the dimerization of the respective HER receptors (homo- an/or heterodimerization).

The invention provides the use of the beta-hairpins of HER3 (and HER4) functionally presented in a 3-dimensional orientation within SlyD scaffolds (see e.g FIG. 2, and the polypeptides of SEQ ID NOs. 13, and 17 to 24) to obtain HER3 antibodies or binding for use in the generation of a bispecific HER3/HER2 antibody.

The invention provides the use of a) at least one polypeptide selected from the group consisting of:

| | |
|---|---|
| SEQ ID NO: 13 | TtSlyD-FKBP-Her3, |
| SEQ ID NO: 17 | TtSlyDcas-Her3, |
| SEQ ID NO: 18 | TtSlyDcys-Her3, |
| SEQ ID NO: 19 and | TgSlyDser-Her3, |
| SEQ ID NO: 20 | TgSlyDcys-Her3, | which comprises the amino acid sequence of SEQ ID NO:1;

(and, optionally b) at least one polypeptide selected from the group consisting of:

| | |
|---|---|
| SEQ ID NO: 21 | TtSlyDcas-Her4, |
| SEQ ID NO: 22 | TtSlyDcys-Her4, |
| SEQ ID NO: 23 and | TgSlyDser-Her4, |
| SEQ ID NO: 24 | TgSlyDcys-Her4,) | in a method for selecting an antibody, in particular an antibody that binds to human HER3 (and binds to human HER4) for use in the generation of a bispecific HER3/HER2 antibody,
wherein the antibody, binds within an amino acid sequence of PQPLVYNKLTFQLEPNPHT (SEQ ID NO:1) of human HER3;
and such HER3 antibody is then used to generate a bispecific HER3/HER2 antibody.

The invention provides a bispecific antibody which binds to human HER3 and to human HER2, wherein the antibody binds within an amino acid sequence of PQPLVYNKLTFQLEPNPHT (SEQ ID NO:1) which is comprised in a polypeptide selected from the group consisting of:

| | |
|---|---|
| SEQ ID NO: 13 | TtSlyD-FKBP-Her3, |
| SEQ ID NO: 17 | TtSlyDcas-Her3, |
| SEQ ID NO: 18 | TtSlyDcys-Her3, |
| SEQ ID NO: 19 and | TgSlyDser-Her3, |
| SEQ ID NO: 20 | TgSlyDcys-Her3. |

The invention provides a bispecific antibody which binds to human HER3 and to human HER2, wherein the antibody binds within an amino acid sequence of PQPLVYNKLTFQLEPNPHT (SEQ ID NO:1) which is comprised in a polypeptide of SEQ ID NO: 18 (TtSlyDcys-Her3).

One embodiment of the invention is a bispecific antibody that binds to the beta-hairpin of human HER3 PQPLVYNKLTFQLEPNPHT (SEQ ID NO:1) and that binds to domain II of human HER2 (SEQ ID NO: 59). One embodiment of the invention is a bispecific antibody which antibody binds to the polypeptide of SEQ ID NO: 18

(TtSlyDcys-Her3) which comprises the amino acid sequence PQPLVYNKLTFQLEPNPHT (SEQ ID NO:1) and which antibody binds to domain II of human HER2 n(SEQ ID NO: 59).

One embodiment of the invention is a bispecific antibodies that binds to the beta-hairpin of human HER3 PQPLVYNKLTFQLEPNPHT (SEQ ID NO:1) and that binds to the same epitope on human HER2 as pertuzumab. One embodiment of the invention is a bispecific antibody which antibody binds to the polypeptide of SEQ ID NO: 18 (TtSlyDcys-Her3) which comprises the amino acid sequence PQPLVYNKLTFQLEPNPHT (SEQ ID NO:1) and which antibody binds to the same epitope on human HER2 as pertuzumab.

One embodiment of the invention is a bispecific antibodies that binds to the beta-hairpin of human HER3 PQPLVYNKLTFQLEPNPHT (SEQ ID NO:1) and that competes for binding to human HER2 with pertuzumab. One embodiment of the invention is a bispecific antibody which antibody binds to the polypeptide of SEQ ID NO: 18 (TtSlyDcys-Her3) which comprises the amino acid sequence PQPLVYNKLTFQLEPNPHT (SEQ ID NO:1) and which antibody competes for binding to human HER2 with pertuzumab.

One embodiment of the invention is a bispecific antibody that binds to the beta-hairpin of human HER3 PQPLVYNKLTFQLEPNPHT (SEQ ID NO:1) and that binds to human HER2 and comprises all six heavy and light chains HVRs of pertuzumab (SEQ ID NO: 60, SEQ ID NO: 61, SEQ ID NO: 62, SEQ ID NO: 63, SEQ ID NO: 64, and SEQ ID NO: 65). One embodiment of the invention is a bispecific antibodies that binds to the beta-hairpin of human HER3 PQPLVYNKLTFQLEPNPHT (SEQ ID NO:1) and that binds to human HER2 and comprises the VH and VL of pertuzumab (SEQ ID NO: 66 and SEQ ID NO. 67)).

One embodiment is a multispecific antibody that binds to human HER3 and human HER2 as described above which binds also to human HER4. In one embodiment such multispecific antibody that binds to human HER3 and human HER2 binds also to the beta-hairpin of human HER4 PQTFVYNPTTFQLEHNFNA (SEQ ID NO:2). In one embodiment such multispecific antibody that binds to human HER3 and human HER2 also binds to the polypeptide of SEQ ID NO: 22 (TtSlyDcys-Her4) which comprises the amino acid sequence PQTFVYNPTTFQLEHNFNA (SEQ ID NO:2).

In one embodiment such bispecific HER3/HER2 does not crossreact with human HER4. In one embodiment such bispecific HER3/HER2 does not crossreact with the beta-hairpin of human HER4 PQTFVYNPTTFQLEHNFNA (SEQ ID NO:2). In one embodiment such bispecific HER3/HER2 does not crossreact with the polypeptide of SEQ ID NO: 22 (TtSlyDcys-Her4) which comprises the amino acid sequence PQTFVYNPTTFQLEHNFNA (SEQ ID NO:2).

One embodiment of the invention is a bispecific antibody
a) that binds to human HER3 and comprises the heavy chain HVRs of
SEQ ID NO: 25 heavy chain HVR-H1, M-05-74,
SEQ ID NO: 26 heavy chain HVR-H2, M-05-74, and
SEQ ID NO: 27 heavy chain HVR-H3, M-05-74,
and comprises the light chain heavy chain HVRs of
SEQ ID NO: 28 light chain HVR-L1, M-05-74,
SEQ ID NO: 29 light chain HVR-L2, M-05-74, and
SEQ ID NO: 30 light chain HVR-L3, M-05-74;
and
b) that binds to human HER2 and comprises the heavy chain HVRs of
SEQ ID NO: 60 heavy chain HVR-H1, pertuzumab,
SEQ ID NO: 61 heavy chain HVR-H2 pertuzumab,
SEQ ID NO: 62 heavy chain HVR-H3, pertuzumab,
and comprises the light chain heavy chain HVRs of
SEQ ID NO: 63 light chain HVR-L1, pertuzumab,
SEQ ID NO: 64 light chain HVR-L2, pertuzumab, and
SEQ ID NO: 65 light chain HVR-L3 pertuzumab.

One embodiment of the invention is a bispecific antibody
a) that binds to human HER3 and comprises
i) a variable heavy chain domain VH with the amino acid sequence of SEQ ID NO:33 and a variable light chain domain VL with the amino acid sequence of SEQ ID NO:41,
ii) a variable heavy chain domain VH with the amino acid sequence of SEQ ID NO:33 and a variable light chain domain VL with the amino acid sequence of SEQ ID NO:39, or
iii) a variable heavy chain domain VH with the amino acid sequence of SEQ ID NO:33 and a variable light chain domain VL with the amino acid sequence of SEQ ID NO:42; and
b) that binds to human HER2 and a variable heavy chain domain VH with the amino acid sequence of SEQ ID NO:66 and a variable light chain domain VL with the amino acid sequence of SEQ ID NO:67.

In one preferred embodiment such bispecific antibody is bivalent.

The invention further provides an isolated nucleic acid encoding such bispecific HER3/HER2 antibody.

The invention further provides a host cell comprising such nucleic acid.

The invention further provides a method of producing such antibody comprising culturing such host cell so that the antibody is produced.

In on embodiment such method further comprises recovering such antibody from the host cell.

The invention further provides an immunoconjugate comprising such bispecific HER3/HER2 and a cytotoxic agent.

The invention further provides a pharmaceutical formulation comprising such bispecific HER3/HER2 antibody and a pharmaceutically acceptable carrier.

The invention further provides the bispecific HER3/HER2 antibody described herein for use as a medicament. The invention further provides the bispecific HER3/HER2 antibody described herein, or the immunoconjugate comprising the bispecific HER3/HER2 antibody and a cytotoxic agent, for use in treating cancer. The invention further provides the bispecific HER3/HER2 antibody described herein for use in inhibition of HER3/HER2 dimerization and/or HER2/HER2 dimerization.

Use of such bispecific HER3/HER2 antibody, or an immunoconjugate comprising the bispecific HER3/HER2 antibody and a cytotoxic agent, in the manufacture of a medicament. Such use wherein the medicament is for treatment of cancer. Such use wherein the medicament is for the inhibition of HER3/HER2 dimerization and/or HER2/HER2 dimerization.

The invention further provides a method of treating an individual having cancer comprising administering to the individual an effective amount of the bispecific HER3/HER2 antibody described herein, or an immunoconjugate comprising the bispecific HER3/HER2 antibody and a cytotoxic agent.

The invention further provides a method of inhibiting growth of a tumor cell in an individual suffering from cancer comprising administering to the individual an effective amount of the bispecific HER3/HER2 antibody as described herein, thereby inhibiting growth of a tumor cell in the individual.

Disclosed is a polypeptide selected from the group consisting of:

| i) | SEQ ID NO: 13 | TtSlyD-FKBP-Her3, |
|---|---|---|
| ii) | SEQ ID NO: 17 | TtSlyDcas-Her3, |
| iii) | SEQ ID NO: 18 | TtSlyDcys-Her3, |
| iv) and | SEQ ID NO: 19 | TgSlyDser-Her3, |
| v) | SEQ ID NO: 20 | TgSlyDcys-Her3, | which polypeptide comprises the amino acid sequence of SEQ ID NO:1

Disclosed is a polypeptide selected from the group consisting of:

| i) | SEQ ID NO: 21 | TtSlyDcas-Her4, |
|---|---|---|
| ii) | SEQ ID NO: 22 | TtSlyDcys-Her4, |
| iii) and | SEQ ID NO: 23 | TgSlyDser-Her4, |
| iv) | SEQ ID NO: 24 | TgSlyDcys-Her4, | which polypeptide comprises the amino acid sequence of SEQ ID NO:2.

Using the beta-hairpins of HER3 (and HER4) functionally presented in a 3-dimensional orientation within SlyD scaffolds (see e.g FIG. 2, and the polypeptides of SEQ ID NOs. 13, and 17 to 24) the bispecific HER3/HER2 antibodies, described herein binding to these beta-hairpins could be selected.

It was found that the antibodies, according to the invention can have highly valuable properties such as strong growth inhibition of HER3 expressing cancer cells, strong inhibition of HER3 mediated signal transduction (such as e.g. HER3 phosphorylation) which is related to cancer cell proliferation, or very specific pharmacokinetic properties (such as faster association rates and higher Molar Ratios of the binding the activated HER3 in the presence of Heregulin ("open conformation) when compared to the absence of Heregulin ("closed conformation"). Furthermore they show strong tumor growth inhibition and are able to efficiently inhibit HER3/HER2 dimerization and/or HER2/HER2 dimerization.

BRIEF DESCRIPTION OF THE FIGURES

FIGS. 1A-E Schematic overview of "closed" and "open" HER3 conformation and the influence of the Neuregulin family ligands (like e.g. Heregulin abbreviated here as HR) on the conformation change.

FIG. 2 3D-structure of the beta-hairpin of HER3 functionally presented in a 3-dimensional orientation within a SlyD scaffold of *Thermus thermophiles*.

FIG. 13 Results from the CelluSpots™ Ala-Scan of anti HER3/HER4 antibody M-05-74 (named M-074 in the Figure) and anti-HER3 antibody M-08-11 (named M-011) with no HER4 crossreactivity)—the amino acids which are contributing most to the binding of anti-HER3/HER4 antibody M-05-74 to its HER3 ECD binding epitope VYNKLTFQ-LEP (SEQ ID NO:43) and to its HER4 ECD binding epitope VYNPTTFQLE (SEQ ID NO:44) are underlined/bold.

FIG. 14 Binding of M-05-74 (M-074) induces/promotes binding of HRG to the HER3-ECD.

FIG. 15 Inhibition of HER2/HER3 heterodimers/heterodimerization (Imunoprecipitation and Western Blot) in MCF7 cells (HER3-IP=immunoprecipitation with HER3 antibody/HER2-IP=immunoprecipitation with HER3 antibody).

DETAILED DESCRIPTION OF EMBODIMENTS OF THE INVENTION

I. Definitions

Figure 2:
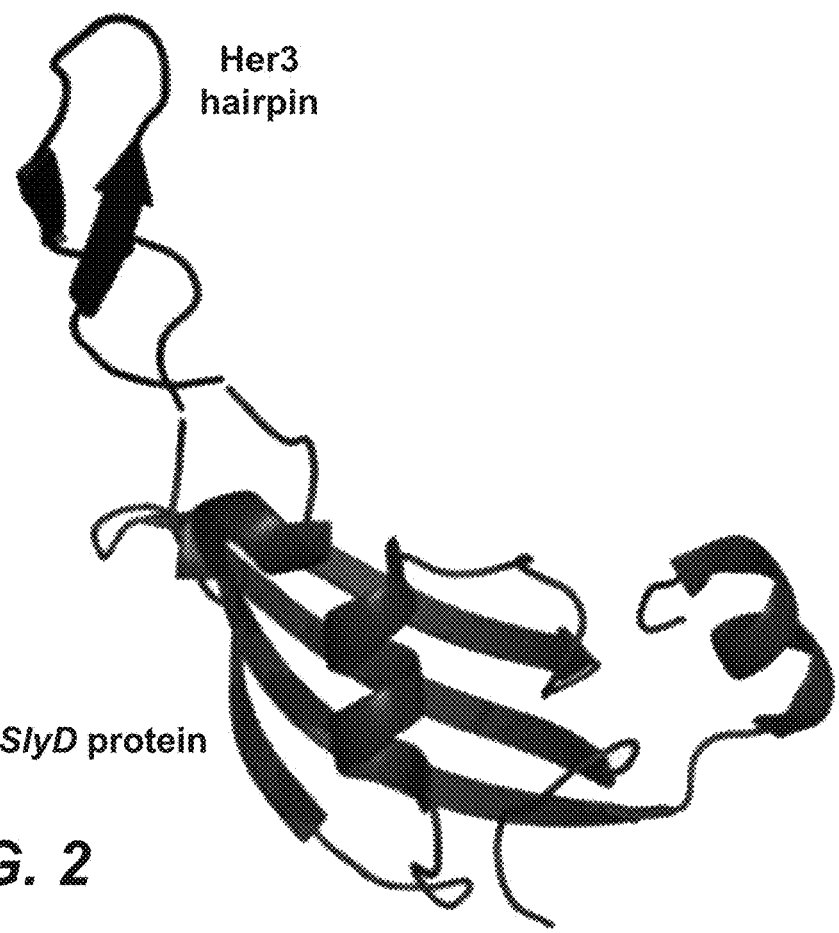

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "bispecific HER3/HER2 antibody", "a bispecific (HER3/HER2) antibody that binds to (human) HER3 and that binds to (human) HER2" and "a bispecific (HER3/HER2) antibody that specifically binds to (human) HER3 and that specifically binds to (human) HER2" refer to an antibody that is capable of binding HER3 with sufficient affinity such that the antibody is useful as a diagnostic and/or therapeutic agent in targeting HER3 and is capable of binding HER2 with sufficient affinity such that the antibody is useful as a diagnostic and/or therapeutic agent in targeting HER2. In one embodiment, the extent of binding of an bispecific HER3/HER2 antibody to an unrelated, non-HER3 protein (except of HER4) is less than about 10% of the binding of the antibody to HER3 or HER2 as measured, e.g., by a Surface Plasmon Resonance assay (e.g. BIACORE). In certain embodiments, an antibody that binds to human HER3 or HER2 has a KD value of the binding affinity for binding to human HER3 or HER2 of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments the antibody according to the invention, binds (also) to human HER4 and has a KD value of the binding affinity for binding to human HER4 of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In one preferred embodiment the respective KD value of the binding affinities is determined in a Surface Plasmon Resonance assay using the wildtype Extracellular domain (ECD) of human HER3 or HER2 (HER3-ECD or HER2-ECD) for the HER3 binding affinity or HER2 binding affinity, respectively. and wildtype human HER4-ECD for the HER4 binding affinity, respectively. In case the bispecific HER3/HER2 antibody also binds to (human) HER4, the terms "bispecific HER3/HER2 antibody", "an bispecific (HER3/HER2) antibody that binds to (human) HER3 and that binds to (human) HER2" and "an bispecific (HER3/HER2) antibody that specifically binds to (human) HER3 and that specifically binds to (human) HER2" refer to a "multispecific HER3/HER2 antibody that also binds to (human) HER4", "a multispecific (HER3/HER2) antibody that binds to (human) HER3 and that binds to (human) HER2 that also binds to (human) HER4" and "a multispecific (HER3/HER2) antibody that specifically binds to (human) HER3 and that specifically binds to (human) HER2 that also binds to (human) HER4".

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

Antibody specificity refers to selective recognition of the antibody for a particular epitope of an antigen. Natural antibodies, for example, are monospecific.

"Bispecific antibodies" according to the invention are antibodies which have two different antigen-binding specificities. Antibodies of the present invention are specific for two different antigens, VEGF as first antigen and ANG-2 as second antigen.

The term "monospecific" antibody as used herein denotes an antibody that has one or more binding sites each of which bind to the same epitope of the same antigen.

The term "valent" as used within the current application denotes the presence of a specified number of binding sites in an antibody molecule. As such, the terms "bivalent", "tetravalent", and "hexavalent" denote the presence of two binding site, four binding sites, and six binding sites, respectively, in an antibody molecule. In one preferred embodiment of the invention the bispecific antibodies according to the invention are "bivalent".

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. In one preferred embodiment such cancer is a breast cancer, ovarian cancer, cervical cancer, lung cancer or prostate cancer. In one preferred embodiment such cancers are further characterized by HER3 expression (or overexpression). In one preferred embodiment such cancers are additionally further characterized by HER2 expression (or overexpression). One further embodiment the invention are the bispecific HER3/HER2 antibodies of the present invention for use in the simultaneous treatment of primary tumors and new metastases.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ respectively.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof and the various antitumor or anticancer agents disclosed below. In one preferred embodiment the "cytotoxic agent" is *Pseudomonas* exotoxin A or variants thereof. In one preferred embodiment the "cytotoxic agent" is amatoxin or a variants thereof.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The term "Fc region" herein is used to define a C-terminal region of an immunoglobulin heavy chain that contains at least a portion of the constant region.

The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized variant" of an antibody, e.g., a non-human antibody, refers to an antibody that has undergone humanization. In one preferred embodiment, a murine HVR is grafted into the framework region of a human antibody to prepare the "humanized antibody." See e.g. Riechmann, L., et al., Nature 332 (1988) 323-327; and Neuberger, M. S., et al., Nature 314 (1985) 268-270. The murine variable region amino acid sequence is aligned to a collection of human germline antibody V-genes, and sorted according to sequence identity and homology. The acceptor sequence is selected based on high overall sequence homology and optionally also the presence of the right canonical residues already in the acceptor sequence (see Poul, M-A. and Lefranc, M-P., in "Ingénierie des anticorps banques combinatores" ed. by Lefranc, M-P. and Lefranc, G., Les Editions INSERM, 1997). The germline V-gene encodes only the region up to the beginning of HVR3 for the heavy chain, and till the middle of HVR3 of the light chain. Therefore, the genes of the germline V-genes are not aligned over the whole V-domain. The humanized construct comprises the human frameworks 1 to 3, the murine HVRs, and the human framework 4 sequence derived from the human JK4, and the JH4 sequences for light and heavy chain, respectively. Before selecting one particular acceptor sequence, the so-called canonical loop structures of the donor antibody can be determined (see Morea, V., et al., Methods, Vol 20, Issue 3 (2000) 267-279). These canonical loop structures are determined by the type of residues present at the so-called canonical positions. These positions lie (partially) outside of the HVR regions, and should be kept functionally equivalent in the final construct in order to retain the HVR conformation of the parental (donor) antibody.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an bispecific HER3/HER2 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Mab" refers to monoclonal antibodies, whereas the term "hMab" refers to humanized variants of such monoclonal antibodies.

A "naked antibody" refers to an antibody that is not conjugated to a heterologous moiety (e.g., a cytotoxic moiety) or radiolabel. The naked antibody may be present in a pharmaceutical formulation. (Include if Prior art has immunoconjugates).

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "HER3," as used herein, refers to any native HER3 from any vertebrate source, including mammals such as primates (e.g. humans) and rodents (e.g., mice and rats), unless otherwise indicated. The term encompasses "full-length," unprocessed HER3 as well as any form of HER3 that results from processing in the cell. The term also encompasses naturally occurring variants of HER3, e.g., splice variants or allelic variants. The amino acid sequence of an exemplary human HER3 is shown in SEQ ID NO:3. "Human HER3" (ErbB-3, ERBB3, c-erbB-3,c-erbB3, receptor tyrosine-protein kinase erbB-3, SEQ ID NO: 3) encodes a member of the epidermal growth factor receptor (EGFR) family of receptor tyrosine kinases which also includes HER1 (also known as EGFR), HER2, and HER4 (Kraus, M. H. et al, PNAS 86 (1989) 9193-9197; Plowman, G. D. et al, PNAS 87 (1990) 4905-4909; Kraus, M. H. et al, PNAS 90 (1993) 2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This membrane-bound protein has a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski M. X., et al, J. Biol. Chem. 269 (1994) 14661-14665; Alimandi M, et al, Oncogene. 10 (1995) 1813-1821; Hellyer, N.J., J. Biol. Chem. 276 (2001) 42153-4261; Singer, E., J. Biol. Chem. 276 (2001) 44266-44274; Schaefer, K. L., Neoplasia 8 (2006) 613-622) For an overview of HER3 and its various interactions within the HER receptor family and the NGR ligands family see e.g. G Sithanandam et al Cancer Gene Therapy (2008) 15, 413-448.

Interestingly in its equilibrium state, the HER3 receptors exists in its "closed confirmation", which does mean, the heterodimerization HER3 beta-hairpin motive is tethered via non-covalent interactions to the HER3 ECD domain IV (see FIG. 1c). It is supposed, that the "closed" HER3 conformation can be opened via the binding of the ligand heregulin at a specific HER3 heregulin binding site. This takes place at the HER3 interface formed by the HER3 ECD domains I and domain III. By this interaction it is believed, that the HER3 receptor is activated and transferred into its "open conformation" (see FIG. 1b and e.g. Baselga, J. et al, Nat Rev Cancer 9 (2009). 463-475 and Desbois-Mouthon, C., at al, Gastroenterol Clin Biol 34 (2010) 255-259). In this open conformation heterodimerization and transignal induction with HER2 is possible (see FIG. 1b).

The term "HER2," as used herein, refers to any native HER2 from any vertebrate source, including mammals such as primates (e.g., humans) and rodents (e.g., mice and rats), unless otherwise indicated. The term encompasses "full-length," unprocessed HER2 as well as any form of HER2 that results from processing in the cell. The term also encompasses naturally occurring variants of HER4, e.g., splice variants or allelic variants. The amino acid sequence of an exemplary human HER2 is shown in SEQ ID NO:5. "Human HER2" (also known as c-erb B2/neu protein, p185erbB2, proto-oncogene Neu, proto-oncogene c-ErbB-2, receptor tyrosine-protein kinase erbB-2, v-erb-b2 erythroblastic leukemia viral oncogene homolog 2, neuro/glioblastoma derived oncogene homolog; SEQ ID NO:9) is a transmembrane surface-bound receptor tyrosine kinase and is normally involved in the signal transduction pathways leading to cell growth and differentiation. HER2 is a promising target for treatment of breast cancer as it was found to be overexpressed in about one-quarter of breast cancer patients (Bange et al, 2001, Nature Medicine 7:548). HER2 an oncogene and overexpression or mutation of this receptor lead to its constitutive activation. This drives the formation of various cancers, like breast, oral, pancreas and lung carcinoma (Schneider et al. 1989, Weiner et al. 1990, Hou et al. 1992, Revillion et al. 1998). HER2 is the only receptor of the HER family, which is not expressed in the tethered conformation like HER1, HER3 and HER4 are. Instead it is expressed in an open, extended conformation on the cell surface. In this conformation the β-hairpin of subdomain II is accessible. The antibody Pertuzumab (Perjeta®) was shown to bind immediate to the HER2 extracellular domain (ECD) β-hairpin and surrounding region in subdomain II. The β-hairpin is essential for the formation of dimers with other HER receptors. By binding to this epitope, Pertuzumab is able to inhibit dimer formation and therefore the activation of subsequent signaling cascades.

The HER2/HER3 heterodimer induces one of the most important mitogenic signals via the PI3K and AKT pathway among HER family members (Sliwkowski M. X., et al, J. Biol. Chem. 269 (1994) 14661-14665; Alimandi M, et al, Oncogene. 10 (1995) 1813-1821; Hellyer, N.J., J. Biol. Chem. 276 (2001) 42153-4261; Singer, E., J. Biol. Chem. 276 (2001) 44266-44274; Schaefer, K. L., Neoplasia 8 (2006) 613-622). Especially the formation of HRG1β induced HER2/HER3 heterodimers plays a pivotal role in cancers with autocrine HRG loops (Gollamudi et al. 2004). Additionally, the results of current clinical studies indicate, that success of anti-HER2 antibody treatments is reduced in presence of HRG1β (McDonagh et al. 2012).

The "epitope of pertuzumab" is the region in the extracellular domain of HER2 to which the antibody pertuzumab binds. In order to screen for antibodies which bind to the same epitope as pertuzumab, a routine cross-blocking assay such as that described in "Ed. Harlow and David Lane, Antibodies, A Laboratory Manual, Cold Spring Harbor Laboratory, (1988)", can be performed. Alternatively, epitope mapping can be performed to assess whether the antibody binds to the pertuzumab epitope of HER2 (e.g. any one or more residues in the region from about residue 22 to about residue 584 of HER2, inclusive). The binding epitope of pertuzumab comprises residues from domain II in the extracellular domain of HER2. Pertuzumab bind to the extracellular domain of HER2 at the junction of domains I, II and III. See also Franklin, et al., Cancer Cell 5 (2004) 317-328.

The term "HER4," as used herein, refers to any native HER4 from any vertebrate source, including mammals such as primates (e.g. humans) and rodents (e.g., mice and rats), unless otherwise indicated. The term encompasses "full-length," unprocessed HER4 as well as any form of HER4 that results from processing in the cell. The term also encompasses naturally occurring variants of HER4, e.g., splice variants or allelic variants. The amino acid sequence of an exemplary human HER4 is shown in SEQ ID NO:5. "Human HER4" (also known as ErbB-4 ERBB4, v-erb-a erythroblastic leukemia viral oncogene homolog 4, p180erbB4 avian erythroblastic leukemia viral (v-erb-b2) oncogene homolog 4; SEQ ID NO:5) is a single-pass type I transmembrane protein with multiple furin-like cysteine rich domains, a tyrosine kinase domain, a phosphotidylinositol-3 kinase binding site and a PDZ domain binding motif (Plowman G D, wt al, PNAS 90:1746-50(1993); Zimonjic D B, et al, Oncogene 10:1235-7(1995); Culouscou J M, et al, J. Biol. Chem. 268:18407-10(1993)). The protein binds to and is activated by neuregulins-2 and -3, heparin-binding EGF-like growth factor and betacellulin. Ligand binding induces a variety of cellular responses including mitogenesis and differentiation. Multiple proteolytic events allow for the release of a cytoplasmic fragment and an extracellular fragment. Mutations in this gene have been associated with cancer. Alternatively spliced variants which encode different protein isoforms have been described; however, not all variants have been fully characterized.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on the finding that using the beta-hairpins of HER3 (and optionally HER4) functionally presented in a 3-dimensional orientation within SlyD scaffolds (see e.g FIG. 2, and the polypeptides of SEQ ID NO. 13, and 17 to 24) it was possible to select antibodies which are specific for the beta-hairpin of HER3 (and HER4). They are used together with antibodies against HER2, specifically to the domain II of human HER2, to generate bispecific antibody that to human HER3 and that binds to human HER2, wherein the antibody binds within an amino acid sequence of PQPLVYNKLTFQLEPNPHT (SEQ ID NO:1; beta-hairpin of human HER3) to human HER3 and which binds to domain II of human HER2 (SEQ ID NO: 59).

The bispecific antibodies of the invention are useful, e.g., for the diagnosis or treatment of cancer.

A. Exemplary Bispecific HER3/HER2 Antibodies

The invention provides an isolated bispecific antibody that binds to human HER3 and that binds to human HER2,
wherein the antibody binds within an amino acid sequence of PQPLVYNKLTFQLEPNPHT (SEQ ID NO:1) which is comprised in a polypeptide selected from the group consisting of:

| | |
|---|---|
| SEQ ID NO: 13 | TtSlyD-FKBP-Her3, |
| SEQ ID NO: 17 | TtSlyDcas-Her3, |
| SEQ ID NO: 18 | TtSlyDcys-Her3, |
| SEQ ID NO: 19 and | TgSlyDser-Her3, |
| SEQ ID NO: 20 | TgSlyDcys-Her3. |

The invention provides an isolated bispecific antibody that binds to human HER3 and that binds to human HER2, wherein the antibody binds within an amino acid sequence of PQPLVYNKLTFQLEPNPHT (SEQ ID NO:1) which is comprised in a polypeptide of SEQ ID NO: 18 (TtSlyDcys-Her3).

The invention provides an isolated bispecific antibody that binds to the beta-hairpin of human HER3 (SEQ ID NO: 1) and that binds to domain II of human HER2 (SEQ ID NO: 59).

The invention provides an isolated bispecific antibody that binds to human HER3 and that binds to human HER2, wherein the antibody binds to human HER3 within an amino acid sequence of PQPLVYNKLTFQLEPNPHT (SEQ ID NO:1) which is comprised in a polypeptide of SEQ ID NO: 18 (TtSlyDcys-Her3) and wherein the antibody binds to domain II of human HER2 (SEQ ID NO: 59).

The invention provides an isolated bispecific antibody that binds to the polypeptide of SEQ ID NO: 18 (TtSlyDcys-Her3) which comprises the amino acid sequence PQPLVYNKLTFQLEPNPHT (SEQ ID NO:1) and which antibody binds to domain II of human HER2 (SEQ ID NO: 59).

The invention provides an isolated bispecific antibody that binds to the beta-hairpin of human HER3 PQPLVYNKLTFQLEPNPHT (SEQ ID NO:1) and that binds to the same epitope on human HER2 as pertuzumab.

The invention provides an isolated bispecific antibody that binds to the polypeptide of SEQ ID NO: 18 (TtSlyDcys-Her3) which comprises the amino acid sequence PQPLVYNKLTFQLEPNPHT (SEQ ID NO:1) and which antibody binds to the same epitope on human HER2 as pertuzumab.

The invention provides an isolated bispecific antibody that binds to the beta-hairpin of human HER3 PQPLVYNKLTFQLEPNPHT (SEQ ID NO:1) and that competes for binding to human HER2 with pertuzumab.

The invention provides an bispecific isolated antibody that binds to the polypeptide of SEQ ID NO: 18 (TtSlyDcys-Her3) which comprises the amino acid sequence PQPLVYNKLTFQLEPNPHT (SEQ ID NO:1) and which antibody competes for binding to human HER2 with pertuzumab.

The invention provides an bispecific isolated antibody that binds to the beta-hairpin of human HER3 PQPLVYNKLTFQLEPNPHT (SEQ ID NO:1) and that binds to human HER2 and comprises all six heavy and light chains HVRs of pertuzumab (SEQ ID NO: 60, SEQ ID NO: 61, SEQ ID NO: 62, SEQ ID NO: 63, SEQ ID NO: 64, and SEQ ID NO: 65).

The invention provides an bispecific isolated antibody that binds to the beta-hairpin of human HER3 PQPLVYNKLTFQLEPNPHT (SEQ ID NO:1) and that binds to human HER2 and comprises the VH and VL of pertuzumab (SEQ ID NO: 66 and SEQ ID NO. 67)).

In one embodiment of the invention the bispecific HER3/HER2 antibody as described herein binds also to human HER4 (and is then designated as multispecific HER3/HER2 antibody antibody).

In one embodiment of the invention the multispecific HER3/HER2 antibody as described herein binds also to the beta-hairpin of human HER4 PQTFVYNPTTFQLEHNFNA (SEQ ID NO:2).

In one embodiment of the invention the multispecific HER3/HER2 antibody as described herein binds also to the polypeptide of SEQ ID NO: 22 (TtSlyDcys-Her4) which comprises the amino acid sequence PQTFVYNPTTFQLEHNFNA (SEQ ID NO:2).

An example antibody which binds to the beta-hairpin of human HER3 and also binds to human HER4, to the beta-hairpin of human HER4 PQTFVYNPTTFQLEHNFNA (SEQ ID NO:2) and to the polypeptide of SEQ ID NO: 22 (TtSlyDcys-Her4) which comprises the amino acid sequence PQTFVYNPTTFQLEHNFNA (SEQ ID NO:2) is antibody comprising the VH of SEQ ID NO: 31 (heavy chain variable domain VH, M-05-74) and the VL of SEQ ID NO: 32 (light chain variable domain VL, M-05-74).

In one embodiment of the invention the bispecific HER3/HER2 antibody as described herein does not crossreact with human HER4.

In one embodiment of the invention the bispecific HER3/HER2 antibody as described herein does not crossreact with the beta-hairpin of human HER4 PQTFVYNPTTFQLEHNFNA (SEQ ID NO:2).

In one embodiment of the invention the bispecific HER3/HER2 antibody as described herein does not crossreact with the polypeptide of SEQ ID NO: 22 (TtSlyDcys-Her4) which comprises the amino acid sequence PQTFVYNPTTFQLEHNFNA (SEQ ID NO:2).

An example antibody which binds to the beta-hairpin of human HER3 and does not crossreact with (does not bind to) human HER4, to the beta-hairpin of human HER4 PQTFVYNPTTFQLEHNFNA (SEQ ID NO:2) and to the polypeptide of SEQ ID NO: 22 (TtSlyDcys-Her4) which comprises the amino acid sequence PQTFVYNPTTFQLEHNFNA (SEQ ID NO:2) is antibody comprising the VH of SEQ ID NO: 51 (heavy chain variable domain VH, <Her3> M-08-11) and the VL of SEQ ID NO: 52 (light chain variable domain VL, <Her3> M-08-11).

The invention provides an bispecific isolated antibody
a) that binds to human HER3 and comprises the heavy chain HVRs of
SEQ ID NO: 25 heavy chain HVR-H1, M-05-74,
SEQ ID NO: 26 heavy chain HVR-H2, M-05-74, and
SEQ ID NO: 27 heavy chain HVR-H3, M-05-74,
and comprises the light chain heavy chain HVRs of
SEQ ID NO: 28 light chain HVR-L1, M-05-74,
SEQ ID NO: 29 light chain HVR-L2, M-05-74, and
SEQ ID NO: 30 light chain HVR-L3, M-05-74;
and
b) that binds to human HER2 and comprises the heavy chain HVRs of
SEQ ID NO: 60 heavy chain HVR-H1, pertuzumab,
SEQ ID NO: 61 heavy chain HVR-H2 pertuzumab,
SEQ ID NO: 62 heavy chain HVR-H3, pertuzumab,
and comprises the light chain heavy chain HVRs of
SEQ ID NO: 63 light chain HVR-L1, pertuzumab,
SEQ ID NO: 64 light chain HVR-L2, pertuzumab, and
SEQ ID NO: 65 light chain HVR-L3 pertuzumab.

The invention provides an bispecific isolated antibody
a) that binds to human HER3 and comprises
i) a variable heavy chain domain VH with the amino acid sequence of SEQ ID NO:33 and a variable light chain domain VL with the amino acid sequence of SEQ ID NO:41,
ii) a variable heavy chain domain VH with the amino acid sequence of SEQ ID NO:33 and a variable light chain domain VL with the amino acid sequence of SEQ ID NO:39, or
iii) a variable heavy chain domain VH with the amino acid sequence of SEQ ID NO:33 and a variable light chain domain VL with the amino acid sequence of SEQ ID NO:42;
and
b) that binds to human HER2 and a variable heavy chain domain VH with the amino acid sequence of SEQ ID NO:66 and a variable light chain domain VL with the amino acid sequence of SEQ ID NO:67.

In one embodiment of the invention the bispecific HER3/HER2 antibody as described herein wherein the bispecific antibody is bivalent.

In one embodiment of the invention the bispecific HER3/HER2 antibody as described herein has one or more of the following properties (either alone or in any combination): the antibody a) binds within an amino acid sequence of PQPLVYNKLT-FQLEPNPHT (SEQ ID NO:1) which is comprised in a polypeptide selected from the group consisting of:

| SEQ ID NO: 13 | TtSlyD-FKBP-Her3, |
|---|---|
| SEQ ID NO: 17 | TtSlyDcas-Her3, |
| SEQ ID NO: 18 | TtSlyDcys-Her3, |
| SEQ ID NO: 19 and | TgSlyDser-Her3, |
| SEQ ID NO: 20 | TgSlyDcys-Her3; | b) binds to a polypeptide selected from the group consisting of:

| SEQ ID NO: 13 | TtSlyD-FKBP-Her3, |
|---|---|
| SEQ ID NO: 17 | TtSlyDcas-Her3, |
| SEQ ID NO: 18 | TtSlyDcys-Her3, |
| SEQ ID NO: 19 and | TgSlyDser-Her3, |
| SEQ ID NO: 20 | TgSlyDcys-Her3; | c) inhibits the heterodimerisation of HER3/HER2 heterodimers in MCF-7 cells in a HER3/HER2 coprecipitation assay;
d) shows tumor growth inhibitory activity in vivo;
e) binds with an affinity of a KD value ≤1×10−8 M to HER3-ECD (in one embodiment with a KD value of 1×10−8 M to 1×10−13 M; (in one embodiment with a KD value of 1×10−9 M to 1×10−13 M);
f) binds with an affinity of a KD value ≤1×10−8 M to HER2-ECD (in one embodiment with a KD value of 1×10−8 M to 1×10−13 M; (in one embodiment with a KD value of 1×10−9 M to 1×10−13 M.

In one preferred embodiment the antibody is of IgG1 or IgG4 isotype. In one preferred embodiment the antibody comprises constant domains of human origin (human constant domains.). Typical human constant regions within the meaning of the present invention comprising the respective human constant domains have the amino acid sequences of SEQ ID NO: 53 to SEQ ID NO:58 (which are partly comprising amino acid substitutions).

1. Antibody Affinity

In certain embodiments, an antibody provided herein has a dissociation constant KD of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$M to $10^{-13}$ M).

In one preferred embodiment, KD is measured using surface plasmon resonance assays using a BIACORE® at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$ or ka) and dissociation rates ($k_{off}$ or kd) are calculated using a simple one-to-one Langmuir binding model (BIACORE® Evaluation Software version 3.2) by simultaneously fitting the association and dissociation sensorgrams. The equilibrium dissociation constant KD is calculated as the ratio kd/ka ($k_{off}/k_{on}$) See, e.g., Chen, Y. et al., J. Mol. Biol. 293 (1999) 865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

In one preferred embodiment the antibody fragment is a Fab fragment. In one preferred embodiment the antibody fragment (in case constant domains are contained in the fragment) comprises constant domains of human origin (human constant domains.).

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing SDR (a-CDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling). Morea, V., et al., Methods, Vol 20, Issue 3 (2000) 267-279) and WO2004/006955 (approach via canonical structures).

4. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for HER3/HER4 and the other is for any other antigen.

Multispecific antibodies may also be used to localize cytotoxic agents to cells which express HER3 and/or HER2 (and HER4). Bispecific or multispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to HER3 as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcgammaRI, FcgammaRII and FcgammaRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half life determinations can also be performed using methods known in the art (see, e.g., Petkova, S. B. et al., Int. Immunol. 18 (2006: 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an bispecific HER3/HER2 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an bispecific HER3/HER2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an bispecific HER3/HER2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Bispecific HER3/HER2 (and their parent anti-HER3 and anti-HER2) antibodies provided herein may be identified, screened for, or characterized for their physical/chemical properties and/or biological activities by various assays known in the art.

Disclosed is a method for selecting for an antibody that binds to human HER3 for use in generating bispecific HER3/HER2 antibodies wherein the anti-HER3 antibody binds within an amino acid sequence of PQPLVYNKLTFQLEPNPHT (SEQ ID NO:1) of human HER3; wherein
a) at least one polypeptide selected from the group consisting of:

| SEQ ID NO: 13 | TtSlyD-FKBP-Her3, |
| SEQ ID NO: 17 | TtSlyDcas-Her3, |
| SEQ ID NO: 18 | TtSlyDcys-Her3, |
| SEQ ID NO: 19 and | TgSlyDser-Her3, |
| SEQ ID NO: 20 | TgSlyDcys-Her3, | which comprises the amino acid sequence of SEQ ID NO:1; are used (in a binding assay) to select antibodies, which show binding to the at least one polypeptide under a) and thereby selecting an antibody that binds within an amino acid sequence of PQPLVYNKLTFQLEPNPHT (SEQ ID NO:1) (within human HER3).

In one embodiment the selection method further comprises a step wherein the selected antibodies are counter-screened with the polypeptides (tested for binding to the polypeptides) selected from the group consisting of:

| SEQ ID NO: 14 | TtSlyD-Wildtype |
| SEQ ID NO: 15 | TtSlyDcas |
| SEQ ID NO: 16 | TgSlyDΔIF | to confirm that the selected antibodies do not bind to the polypeptide scaffolds which are not comprising amino acid sequence of PQPLVYNKLTFQLEPNPHT (SEQ ID NO:1).

1. Binding Assays and Other Assays

In one aspect, an antibody of the invention is tested for its antigen binding activity, e.g., by known methods such as ELISA, Western blot, including surface plasmon resonance (e.g. BIACORE), etc.

In another aspect, competition assays may be used to identify an antibody that competes with M-05-74 for binding to HER3 (and/or to HER4) and also to identify an antibody that competes with pertuzumab for binding to HER2. In certain embodiments, such a competing antibody binds to the same epitope (e.g., a linear or a conformational epitope) that is bound by M-05-74. Detailed exemplary methods for mapping an epitope to which an antibody binds are provided in Morris, G. E. (ed.), Epitope Mapping Protocols, In: Methods in Molecular Biology, Vol. 66, Humana Press, Totowa, N.J. (1996). Further methods are described in detail in Example 4 using the CelluSpot™ technology.

In an exemplary competition assay, immobilized HER3(/HER4), or to HER2 is incubated in a solution comprising a first labeled antibody that binds to HER3(/HER4), or to HER2, respectively (e.g., M-05-74 or pertuzumab) and a second unlabeled antibody that is being tested for its ability to compete with the first antibody for binding to HER3(/HER4), or to HER2. The second antibody may be present in a hybridoma supernatant. As a control, immobilized HER3 or HER4 is incubated in a solution comprising the first labeled antibody but not the second unlabeled antibody. After incubation under conditions permissive for binding of the first antibody to HER3(/HER4), or to HER2, excess unbound antibody is removed, and the amount of label associated with immobilized HER3(/HER4), or to HER2 is measured. If the amount of label associated with immobilized HER3(/HER4), or to HER2 is substantially reduced in the test sample relative to the control sample, then that indicates that the second antibody is competing with the first antibody for binding to HER3(/HER4), or to HER2. See Harlow, E. and Lane, D., Antibodies: A Laboratory Manual, Chapter 14, Cold Spring Harbor Laboratory, Cold Spring Harbor, N.Y. (1988).

2. Activity Assays

In one aspect, assays are provided for identifying bispecific HER3/HER2 antibodies thereof having biological activity. Biological activity may include, e.g., inhibition of HER3 and/or HER2 phosphorylation, inhibition of cancer cell proliferation of HER3 and/or HER2 (and/or HER4) expressing or overexpressing cancer cells, inhibition of HER3/HER2 heterodimerization, (time-dependent) internalization via FACS assay, in vivo tumor growth inhibition in xenograft animal (e.g. mouse or rat) models with xenografted HER3 and/or HER2 (and/or HER4) expressing or overexpressing cancer cells. Antibodies having such biological activity in vivo and/or in vitro are also provided.

In certain embodiments, an antibody of the invention is tested for such biological activity. Exemplary vitro or in vivo assays for specified biological activities are described in Example 2e, 3, 5 to 9, and 11 or 17.

D. Immunoconjugates

The invention also provides immunoconjugates comprising an anti-HER3/HER4 antibody described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a *Pseudomonas* exotoxin A or variants thereof. *Pseudomonas* exotoxin A or variants thereof are described e.g in WO2011/32022, WO2009/32954, WO2007/031741, WO2007/016150, WO2005/052006 and Liu W, et al, PNAS 109 (2012) 11782-11787.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made a) either using recombination expression techniques (e.g for the expression of amino acid sequence based toxins fused to a Fab or Fv antibody fragment e.g. in *E. coli*) or b) using polypeptide coupling techniques (like sortase enzyme based coupling of amino acid sequence based toxins to a Fab or Fv antibody fragment) or c) using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the bispecific HER3/HER2 antibodies provided herein is useful for detecting the presence of HER3 and/or HER4, respectively in a biological sample. The term "detecting" as used herein encompasses quantitative or qualitative detection. In certain embodiments, a biological sample comprises a cell or tissue, such as tumor tissues.

In one embodiment, an bispecific HER3/HER2 antibody for use in a method of diagnosis or detection is provided. In a further aspect, a method of detecting the presence of HER3 or HER2, respectively, in a biological sample is provided. In certain embodiments, the method comprises contacting the biological sample with an bispecific HER3/HER2 antibody as described herein under conditions permissive for binding of the anti-bispecific HER3/HER2 antibody to HER3 or HER2, respectively, and detecting whether a complex is formed between the anti-bispecific HER3/HER2 antibody and HER3 or HER2, respectively. Such method may be an in vitro or in vivo method. In one embodiment, an bispecific HER3/HER2 antibody is used to select subjects eligible for therapy with an the bispecific HER3/HER2 antibodies antibody, e.g. where HER3 and HER2, respectively are both biomarkers for selection of patients.

Exemplary disorders that may be diagnosed using an antibody of the invention include cancer.

In certain embodiments, labeled bispecific HER3/HER2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an bispecific HER3/HER2 antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the bispecific HER3/HER2 antibodies or immunoconjugates of the anti-bispecific HER3/HER2 antibodies conjugated to a cytotoxic agent, provided herein may be used in therapeutic methods.

In one aspect, an bispecific HER3/HER2 antibody or immunoconjugate of the anti-v antibody conjugated to a cytotoxic agent for use as a medicament is provided. In further aspects, an bispecific HER3/HER2 antibody or immunoconjugate of the bispecific HER3/HER2 antibody conjugated to a cytotoxic agent for use in treating cancer is provided. In certain embodiments, an bispecific HER3/HER2 antibody or immunoconjugates of the bispecific HER3/HER2 antibody conjugated to a cytotoxic agent for use in a method of treatment is provided. In certain embodiments, the invention provides an bispecific HER3/HER2 antibody or immunoconjugate of the bispecific HER3/HER2 antibody conjugated to a cytotoxic agent for use in a method of treating an individual having cancer comprising administering to the individual an effective amount of the bispecific HER3/HER2 antibody or the immunoconjugate of the bispecific HER3/HER2 antibody conjugated to a cytotoxic agent. In further embodiments, the invention provides an bispecific HER3/HER2 antibody or immunoconjugate of the bispecific HER3/HER2 antibody conjugated to a cytotoxic agent for use in inducing apoptosis in a cancer cell/or inhibiting cancer cell proliferation. In certain embodiments, the invention provides an bispecific HER3/HER2 antibody or immunoconjugate of the bispecific HER3/HER2 antibody conjugated to a cytotoxic agent for use in a method of inducing apoptosis in a cancer cell/or inhibiting cancer cell proliferation in an individual comprising administering to the individual an effective of the bispecific HER3/HER2 antibody or immunoconjugate of the bispecific HER3/HER2 antibodies conjugated to a cytotoxic agent to induce apoptosis in a cancer cell/or to inhibit cancer cell proliferation. An "individual" according to any of the above embodiments is preferably a human.

In a further aspect, the invention provides for the use of an bispecific HER3/HER2 antibody or an immunoconjugate of the bispecific HER3/HER2 antibody conjugated to a cytotoxic agent in the manufacture or preparation of a medicament. In one embodiment, the medicament is for treatment of cancer. In a further embodiment, the medicament is for use in a method of treating cancer comprising administering to an individual having cancer an effective amount of the medicament. In a further embodiment, the medicament is for inducing apoptosis in a cancer cell/or inhibiting cancer cell proliferation. In a further embodiment, the medicament is for use in a method of inducing apoptosis in a cancer cell/or inhibiting cancer cell proliferation in an individual suffering from cancer comprising administering to the individual an amount effective of the medicament to induce apoptosis in a cancer cell/or to inhibit cancer cell proliferation. An "individual" according to any of the above embodiments may be a human.

In a further aspect, the invention provides a method for treating cancer. In one embodiment, the method comprises administering to an individual having cancer an effective amount of an bispecific HER3/HER2 antibody. An "individual" according to any of the above embodiments may be a human.

In a further aspect, the invention provides a method for inducing apoptosis in a cancer cell/or inhibiting cancer cell proliferation in an individual suffering from cancer. In one embodiment, the method comprises administering to the individual an effective amount of an bispecific HER3/HER2 antibody or an immunoconjugate of the bispecific HER3/HER2 antibody conjugated to a cytotoxic compound to induce apoptosis in a cancer cell/or to inhibit cancer cell proliferation in the individual suffering from cancer. In one embodiment, an "individual" is a human.

In a further aspect, the invention provides pharmaceutical formulations comprising any of the bispecific HER3/HER2 antibodies provided herein, e.g., for use in any of the above therapeutic methods. In one embodiment, a pharmaceutical formulation comprises any of the bispecific HER3/HER2 antibodies provided herein and a pharmaceutically acceptable carrier.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-HER3(and anti-HER4) antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-HER3 (and anti-HER4) antibody.

Description of the Amino Acid Sequences
SEQ ID NO: 1 ß-Hairpin of human HER3
SEQ ID NO: 2 ß-Hairpin of human HER4
SEQ ID NO: 3 human HER3
SEQ ID NO: 4 human HER3 Extracellular Domain (ECD)
SEQ ID NO: 5 human HER4
SEQ ID NO: 6 human HER4 Extracellular Domain (ECD)
SEQ ID NO: 7 human HER1
SEQ ID NO: 8 human HER1 Extracellular Domain (ECD)
SEQ ID NO: 9 human HER2
SEQ ID NO: 10 human HER2 Extracellular Domain (ECD)
SEQ ID NO: 11 Human Heregulin fragment (HRG)
SEQ ID NO: 12 Human Heregulin β-1 fragment (as provided from Preprotech)
SEQ ID NO: 13 TtSlyD-FKBP-Her3
SEQ ID NO: 14 TtSlyD-Wildtype
SEQ ID NO: 15 TtSlyDcas
SEQ ID NO: 16 TgSlyDΔIF
SEQ ID NO: 17 TtSlyDcas-Her3
SEQ ID NO: 18 TtSlyDcys-Her3
SEQ ID NO: 19 TgSlyDser-Her3
SEQ ID NO: 20 TgSlyDcys-Her3
SEQ ID NO: 21 TtSlyDcas-Her4
SEQ ID NO: 22 TtSlyDcys-Her4
SEQ ID NO: 23 TgSlyDser-Her4
SEQ ID NO: 24 TgSlyDcys-Her4
SEQ ID NO: 25 heavy chain HVR-H1, M-05-74
SEQ ID NO: 26 heavy chain HVR-H2, M-05-74
SEQ ID NO: 27 heavy chain HVR-H3, M-05-74
SEQ ID NO: 28 light chain HVR-L1, M-05-74
SEQ ID NO: 29 light chain HVR-L2, M-05-74
SEQ ID NO: 30 light chain HVR-L3, M-05-74
SEQ ID NO: 31 heavy chain variable domain VH, M-05-74
SEQ ID NO: 32 light chain variable domain VL, M-05-74
SEQ ID NO: 33 humanized variant A of heavy chain variable domain VH, M-05-74_VH-A
SEQ ID NO: 34 humanized variant B of heavy chain variable domain VH, M-05-74_VH-B
SEQ ID NO: 35 humanized variant 3 of heavy chain variable domain VH, M-05-74_VH-C
SEQ ID NO: 36 humanized variant A of heavy chain variable domain VH, M-05-74_VH-D
SEQ ID NO: 37 humanized variant B of heavy chain variable domain VH, M-05-74_VH-E
SEQ ID NO: 38 humanized variant A of light chain variable domain VL, M-05-74_VL-A
SEQ ID NO: 39 humanized variant B of light chain variable domain VL, M-05-74_VL-B
SEQ ID NO: 40 humanized variant C of light chain variable domain VL, M-05-74_VL-C
SEQ ID NO: 41 humanized variant D of light chain variable domain VL, M-05-74_VL-D
SEQ ID NO: 42 humanized variant E of light chain variable domain VL, M-05-74_VL-E
SEQ ID NO:43 binding epitope within ß-hairpin of human HER3
SEQ ID NO:44 binding epitope within ß-hairpin of human HER4
SEQ ID NO:45 *Pseudomonas* exotoxin variant PE24LR8M 3_G (including a GGG linker)
SEQ ID NO:46 Light chain of M-05-74 (M-05-74_LC)
SEQ ID NO:47 Heavy chain of M-05-74 HC with sortase tag (M-05-74_HC)
SEQ ID NO:48 Heavy chain of M-05-74 HC conjugated to *Pseudomonas* exotoxin variant PE24LR8M (Fab-074-PE heavy chain 1)
SEQ ID NO:49 Heavy chain of M-05-74 HC conjugated to *Pseudomonas* exotoxin variant PE24LR8M (Fab-074-PE heavy chain 2) as direct PE24LR8M fusion
SEQ ID NO: 50 soluble *S. aureus* sortase A
SEQ ID NO: 51 heavy chain variable domain VH, <Her3> M-08-11
SEQ ID NO: 52 light chain variable domain VL, <Her3> M-08-11
SEQ ID NO: 53 human kappa light chain constant region
SEQ ID NO: 54 human lambda light chain constant region
SEQ ID NO: 55 human heavy chain constant region derived from IgG1

SEQ ID NO: 56 human heavy chain constant region derived from IgG1 mutated on L234A and L235A
SEQ ID NO: 57 human heavy chain constant region derived from IgG1 mutated on L234A, L235A and P329G
SEQ ID NO: 58 human heavy chain constant region derived from IgG4
SEQ ID NO: 59 domain II of human HER2
SEQ ID NO: 60 heavy chain HVR-H1, pertuzumab
SEQ ID NO: 61 heavy chain HVR-H2 pertuzumab
SEQ ID NO: 62 heavy chain HVR-H3, pertuzumab
SEQ ID NO: 63 light chain HVR-L1, pertuzumab
SEQ ID NO: 64 light chain HVR-L2, pertuzumab
SEQ ID NO: 65 light chain HVR-L3 pertuzumab
SEQ ID NO: 66 heavy chain variable domain VH, pertuzumab
SEQ ID NO: 67 light chain variable domain VL, pertuzumab
SEQ ID NO: 68 heavy chain 1, bispecific HER3/HER2 antibody DIB×PERT
SEQ ID NO: 69 light chain 1, bispecific HER3/HER2 antibody DIB×PERT
SEQ ID NO: 70 heavy chain 2, bispecific HER3/HER2 antibody DIB×PERT
SEQ ID NO: 71 light chain 2, bispecific HER3/HER2 antibody DIB×PERT The following examples and figures are provided to aid the understanding of the present invention, the true scope of which is set forth in the appended claims. It is understood that modifications can be made in the procedures set forth without departing from the spirit of the invention. The disclosures of all patent and scientific literature cited herein are expressly incorporated by reference in their entirety.

In the Following Several Embodiments of the Invention are Listed

1. Use of
   at least one polypeptide selected from the group consisting of:

SEQ ID NO: 13     TtSlyD-FKBP-Her3,
   SEQ ID NO: 17     TtSlyDcas-Her3,
   SEQ ID NO: 18     TtSlyDcys-Her3,
   SEQ ID NO: 19     TgSlyDser-Her3,
   and
   SEQ ID NO: 20     TgSlyDcys-Her3, which comprises the amino acid sequence of SEQ ID NO:1;
   in a method for selecting an antibody that binds to human HER3 for use in the generation of a bispecific HER3/HER2 antibody,
   wherein the HER3 antibody binds within an amino acid sequence of PQPLVYNKLTFQLEPNPHT (SEQ ID NO:1) of human HER3;
   and such HER3 antibody is then used to generate a bispecific HER3/HER2 antibody.

2. An isolated bispecific antibody which to human HER3 and to human HER2, wherein the antibody binds within an amino acid sequence of PQPLVYNKLTFQLEPNPHT (SEQ ID NO:1) which is comprised in a polypeptide selected from the group consisting of:

SEQ ID NO: 13     TtSlyD-FKBP-Her3,
   SEQ ID NO: 17     TtSlyDcas-Her3,
   SEQ ID NO: 18     TtSlyDcys-Her3,
   SEQ ID NO: 19     TgSlyDser-Her3,
   and
   SEQ ID NO: 20     TgSlyDcys-Her3.

3. An isolated bispecific antibody which to human HER3 and to human HER2, wherein the antibody binds within an amino acid sequence of PQPLVYNKLTFQLEPNPHT (SEQ ID NO:1) which is comprised in a polypeptide of SEQ ID NO: 18 (TtSlyDcys-Her3).

4. An isolated bispecific antibody that binds to the beta-hairpin of human HER3 (SEQ ID NO: 1) and that binds to domain II of human HER2 (SEQ ID NO: 59).

5. An isolated bispecific antibody which to human HER3 and to human HER2, wherein the antibody binds to human HER3 within an amino acid sequence of PQPLVYNKLTFQLEPNPHT (SEQ ID NO:1) which is comprised in a polypeptide of SEQ ID NO: 18 (TtSlyDcys-Her3) and wherein the antibody binds to domain II of human HER2 (SEQ ID NO: 59).

6. An isolated bispecific antibody which antibody binds to the polypeptide of SEQ ID NO: 18 (TtSlyDcys-Her3) which comprises the amino acid sequence PQPLVYNKLTFQLEPNPHT (SEQ ID NO:1) and which antibody binds to domain II of human HER2 (SEQ ID NO: 59).

7. An isolated bispecific antibodies that binds to the beta-hairpin of human HER3 PQPLVYNKLTFQLEPNPHT (SEQ ID NO:1) and that binds to the same epitope on human HER2 as pertuzumab.

8. An isolated bispecific antibody which antibody binds to the polypeptide of SEQ ID NO: 18 (TtSlyDcys-Her3) which comprises the amino acid sequence PQPLVYNKLTFQLEPNPHT (SEQ ID NO:1) and which antibody binds to the same epitope on human HER2 as pertuzumab.

9. An isolated bispecific antibodies that binds to the beta-hairpin of human HER3 PQPLVYNKLTFQLEPNPHT (SEQ ID NO:1) and that competes for binding to human HER2 with pertuzumab.

10. An isolated bispecific antibody which antibody binds to the polypeptide of SEQ ID NO: 18 (TtSlyDcys-Her3) which comprises the amino acid sequence PQPLVYNKLTFQLEPNPHT (SEQ ID NO:1) and which antibody competes for binding to human HER2 with pertuzumab.

11. An isolated bispecific antibodies that binds to the beta-hairpin of human HER3 PQPLVYNKLTFQLEPNPHT (SEQ ID NO:1) and that binds to human HER2 and comprises all six heavy and light chains HVRs of pertuzumab (SEQ ID NO: 60, SEQ ID NO: 61, SEQ ID NO: 62, SEQ ID NO: 63, SEQ ID NO: 64, and SEQ ID NO: 65).

12. An isolated bispecific antibodies that binds to the beta-hairpin of human HER3 PQPLVYNKLTFQLEPNPHT (SEQ ID NO:1) and that binds to human HER2 and comprises the VH and VL of pertuzumab (SEQ ID NO: 66 and SEQ ID NO. 67).

13. The bispecific HER3/HER2 antibody according to any one of the preceding embodiments that binds also to human HER4.

14. The bispecific HER3/HER2 antibody according to any one of the preceding embodiments that binds also to the beta-hairpin of human HER4 PQTFVYNPTTFQLEHNFNA (SEQ ID NO:2).

15. The bispecific HER3/HER2 antibody according to any one of the preceding embodiments that binds also to the polypeptide of SEQ ID NO: 22 (TtSlyDcys-Her4) which comprises the amino acid sequence PQTFVYNPT-TFQLEHNFNA (SEQ ID NO:2).
16. The bispecific HER3/HER2 antibody according to any one of the preceding embodiments that does not crossreact with human HER4.
17. The bispecific HER3/HER2 antibody according to any one of the preceding embodiments that does not crossreact with the beta-hairpin of human HER4 PQTFVYNPT-TFQLEHNFNA (SEQ ID NO:2).
18. The bispecific HER3/HER2 antibody according to any one of the preceding embodiments that does not crossreact with the polypeptide of SEQ ID NO: 22 (TtSlyDcys-Her4) which comprises the amino acid sequence PQT-FVYNPTTFQLEHNFNA (SEQ ID NO:2).
19. An isolated bispecific antibody
   a) that binds to human HER3 and comprises the heavy chain HVRs of
   SEQ ID NO: 25 heavy chain HVR-H1, M-05-74,
   SEQ ID NO: 26 heavy chain HVR-H2, M-05-74, and
   SEQ ID NO: 27 heavy chain HVR-H3, M-05-74,
   and comprises the light chain heavy chain HVRs of
   SEQ ID NO: 28 light chain HVR-L1, M-05-74,
   SEQ ID NO: 29 light chain HVR-L2, M-05-74, and
   SEQ ID NO: 30 light chain HVR-L3, M-05-74;
   and
   b) that binds to human HER2 and comprises the heavy chain HVRs of
   SEQ ID NO: 60 heavy chain HVR-H1, pertuzumab,
   SEQ ID NO: 61 heavy chain HVR-H2 pertuzumab,
   SEQ ID NO: 62 heavy chain HVR-H3, pertuzumab,
   and comprises the light chain heavy chain HVRs of
   SEQ ID NO: 63 light chain HVR-L1, pertuzumab,
   SEQ ID NO: 64 light chain HVR-L2, pertuzumab, and
   SEQ ID NO: 65 light chain HVR-L3 pertuzumab.
20. An isolated bispecific antibody
   a) that binds to human HER3 and comprises
   i) a variable heavy chain domain VH with the amino acid sequence of SEQ ID NO:33 and a variable light chain domain VL with the amino acid sequence of SEQ ID NO:41,
   ii) a variable heavy chain domain VH with the amino acid sequence of SEQ ID NO:33 and a variable light chain domain VL with the amino acid sequence of SEQ ID NO:39, or
   iii) a variable heavy chain domain VH with the amino acid sequence of SEQ ID NO:33 and a variable light chain domain VL with the amino acid sequence of SEQ ID NO:42;
   and
   b) that binds to human HER2 and a variable heavy chain domain VH with the amino acid sequence of SEQ ID NO:66 and a variable light chain domain VL with the amino acid sequence of SEQ ID NO:67.
21. The bispecific HER3/HER2 antibody according to any one of the preceding embodiments wherein the bispecific antibody is bivalent.
22. An isolated nucleic acid encoding the bispecific HER3/HER2 antibody according to any one of the preceding embodiments.
23. A host cell comprising the nucleic acid of embodiment 22.
24. A method of producing the bispecific HER3/HER2 antibody according to any one of the preceding embodiments comprising culturing such host cell so that the antibody is produced.
25. The method of embodiment 24 which further comprises recovering such antibody from the host cell.
26. An immunoconjugate comprising the bispecific HER3/HER2 antibody according to any one of the preceding embodiments and a cytotoxic agent.
27. A pharmaceutical formulation comprising The bispecific HER3/HER2 antibody according to any one of the preceding embodiments and a pharmaceutically acceptable carrier
28. The bispecific HER3/HER2 antibody according to any one of the preceding embodiments for use as a medicament.
29. The bispecific HER3/HER2 antibody according to any one of the preceding embodiments, or the immunoconjugate comprising the bispecific HER3/HER2 antibody and a cytotoxic agent, for use in treating cancer.
30. The bispecific HER3/HER2 antibody according to any one of the preceding embodiments for use in inhibition of HER3/HER2 dimerization and/or HER2/HER2 dimerization.
31. Use of the bispecific HER3/HER2 antibody according to any one of the preceding embodiments, or an immunoconjugate comprising the bispecific HER3/HER2 antibody and a cytotoxic agent, in the manufacture of a medicament.
32. Use of embodiment 31 wherein the medicament is for treatment of cancer.
33. Use of embodiment 31 wherein the medicament is for the inhibition of HER3/HER2 dimerization and/or HER2/HER2 dimerization.
34. A method of treating an individual having cancer comprising administering to the individual an effective amount of the bispecific HER3/HER2 antibody according to any one of the preceding embodiments, or an immunoconjugate comprising the bispecific HER3/HER2 antibody and a cytotoxic agent.
35. A method of inhibiting growth of a tumor cell in an individual suffering from cancer comprising administering to the individual an effective amount of the bispecific HER3/HER2 antibody according to any one of the preceding embodiments, thereby inhibiting growth of a tumor cell in the individual.

EXAMPLES

Materials & General Methods
Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.
Gene Synthesis Desired gene segments were prepared from oligonucleotides made by chemical synthesis. The 400-1600 bp long gene segments, which were flanked by singular restriction endonuclease cleavage sites, were assembled by annealing and ligating oligonucleotides including PCR amplification and subsequently cloned via the indicated restriction sites e.g. EcoRI/BlpI or BsmI/XhoI into the expression vectors described below. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at Sequiserve GmbH (Vaterstetten, Germany).

DNA and Protein Sequence Analysis and Sequence Data Management

Infomax's Vector NT1 Advance suite version 11.5.0 was used for sequence creation, mapping, analysis, annotation and illustration.

Example 1

Preparation of Antigen and Screening Proteins—Generation of Functional ß-Hairpin HER3 and ß-Hairpin HER4 Constructs for Selecting Antibodies Binding to the ß-Hairpin of HER3 and the ß-Hairpin of HER4

To generate functional ß-Hairpin HER3 and HER4 constructs, the amino acid sequences of the ß-Hairpins of HER3 (SEQ ID NO: 1) and HER4 (SEQ ID NO: 2), were grafted into a SlyD polypeptide framework comprising a FKBP domain. In such constructs the grafted ß-Hairpins are freely accessible in contrast to the hidden structure in the native unactivated conformation of HER3 or HER4 (in the absence of ligand as e.g. HRG) (see FIGS. 1c and 1d where the ß-Hairpin of HER3 is hidden).

Figure 3:
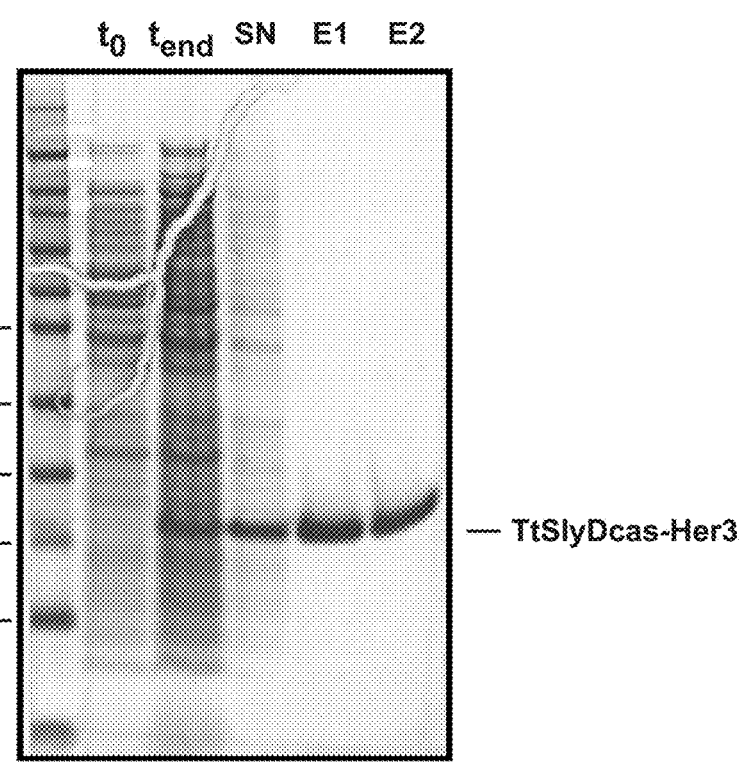
FIG. 3 SDS-PAGE analysis of Ni-NTA purification of TtSlyD-FKBP-Her3. E1 and E2 show the purified fractions 12 and 13.SN: *E. coli* lysate supernatant before purification.
Figure 4:
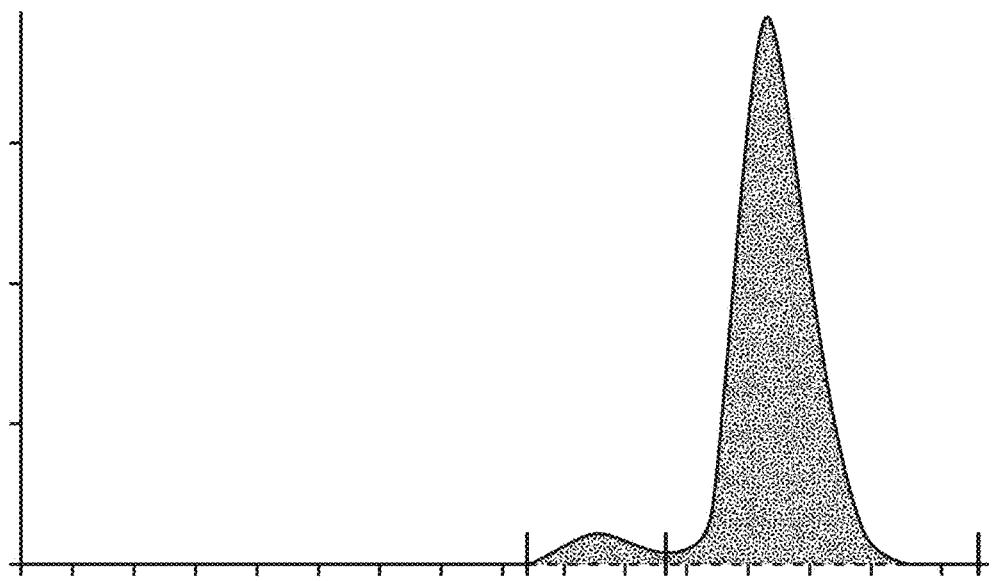
FIG. 4 SEC elution profile of a Ni-NTA purified fraction of *Thermus thermophilus* SlyD-FKBP-Her-3.

All fused SlyD polypeptides can be purified and refolded by using almost identical protocols. E. coli BL21 (DE3) cells transformed with the particular expression plasmid were grown at 37° C. in LB medium containing the respective antibiotic for selective growth (Kanamycin 30 µg/ml, or Ampicillin (100 µg/ml)) to an OD600 of 1.5, and cytosolic overexpression was induced by adding 1 mM isopropyl-ß-D-thiogalactoside (IPTG). Three hours after induction, cells were harvested by centrifugation (20 min at 5,000 g), frozen and stored at −20° C. For cell lysis, the frozen pellet was resuspended in chilled 50 mM sodium phosphate buffer (pH 8.0) supplemented with 7 M GdmCl and 5 mM imidazole. Thereafter the suspension was stirred for 2-10 hours on ice to complete cell lysis. After centrifugation (25,000 g, 1 h) and filtration (cellulose nitrate membrane, 8.0 µm, 1.2 µm, 0.2 µm), the lysate was applied onto a Ni-NTA column equilibrated with the lysis buffer. In the subsequent washing step the imidazole concentration was raised to 10 mM (in 50 mM sodium phosphate buffer (pH 8.0) comprising 7 M GdmCl) and 5 mM TCEP was added in order to keep the thiol moieties in a reduced form and to prevent premature disulfide bridging. At least 15 to 20 volumes of the reducing washing buffer were applied. Thereafter, the GdmCl solution was replaced by 50 mM sodium phosphate buffer (pH 8.0) comprising 100 mM NaCl, 10 mM imidazole, and 5 mM TCEP to induce conformational refolding of the matrix-bound SlyD fusion polypeptide. In order to avoid reactivation of co-purifying proteases, a protease inhibitor cocktail (Complete® EDTA-free, Roche) was added to the refolding buffer. A total of 15 to 20 column volumes of refolding buffer were applied in an overnight procedure. Thereafter, both TCEP and the Complete® EDTA-free inhibitor cocktail were removed by washing with 10 column volumes 50 mM sodium phosphate buffer (pH 8.0) comprising 100 mM NaCl and 10 mM imidazole. In the last washing step, the imidazole concentration was raised to 30 mM (10 column volumes) in order to remove tenacious contaminants. The refolded polypeptide was then eluted by applying 250 mM imidazole in the same buffer. Protein-containing fractions were assessed for purity by Tricine-SDS-PAGE (Schaegger, H. and von Jagow, G., Anal. Biochem. 166 (1987) 368-379). Subsequently, the protein was subjected to size-exclusion-chromatography (Superdex™ HiLoad, Amersham Pharmacia) using potassium phosphate as the buffer system (50 mM potassium phosphate buffer (pH 7.0), 100 mM KCl, 0.5 mM EDTA). Finally, the protein-containing fractions were pooled and concentrated in an Amicon cell (YM10) to a concentration of ~5 mg/ml. Exemplarily SDS-PAGE analysis of Ni-NTA purification of TtSlyD-FKBP-Her3 is shown in FIG. 3 and SEC elution profile of a Ni-NTA purified fraction of Thermus thermophilus SlyD-FKBP-Her-3 is shown in FIG. 4. The Thermus thermophilus SlyD (TtSlyD)-Her-3 fusion polypeptide could be purified successfully as a soluble and stable polypeptide in its monomeric form. The final yield was quantified at 16.4 mg purified protein from fraction 12 and 13.

Table 2: Summary of the amino acid sequences of the developed SlyD-based epitope scaffolds (which carry the HER3 dimerization domain fragment (ß-Hairpin of HER3 (SEQ ID NO: 1)) as insert or the HER4 dimerization domain fragment (ß-Hairpin of HER4 (SEQ ID NO: 2)) as insert).

TtSlyD-FKBP-Her3, TtSlyDcas-Her3, TtSlyDcys-Her3, Thermococcus gammatolerans TgSlyDser-Her3 and TgSly-Dcys-Her3 carry the Her3 dimerization domain fragment (ß-Hairpin of HER3 (SEQ ID NO: 1)) as insert and were used as immunogens and as positive controls in ELISA screening.

TtSlyD-Wildtype, TtSlyDcas, TgSlyDΔIF were used as negative controls in the ELISA screening (without the Her3 dimerization domain fragment (ß-Hairpin of HER3 (SEQ ID NO: 1)) or the Her4 dimerization domain fragment (ß-Hairpin of HER4 (SEQ ID NO: 2)) as insert).

TtSlyDcas-Her4, TtSlyDcys-Her4, TgSlyDser-Her4 and TgSlyDcys-Her4 (which carry the Her4 dimerization domain fragment (ß-Hairpin of HER4 (SEQ ID NO: 2)) as insert) were used in the ELISA screening to check the developed clones for HER4 crossreactivity.

As the epitope scaffolds are expressed in E. coli the N-terminal methionine residue can be present or not. (Nt=N-terminal; Ct=C-terminal)

TABLE 2

| | |
|---|---|
| TtSlyD-FKBP-Her3 | Nt-MRSKVGQDKVVTIRYTLQVEGEVLDQGELSYLHGHRNLIPGLE EALEGREEGEAFQAHVPAEKAYGAGSPQPLVYNKLTFQLEPNP HTKGSSGKDLDFQVEVVKVREATPEELLHGHAHG GGSRKHHHHH HHH-Ct |
| TtSlyD-Wild-type | Nt-MRGSKVGQDKVVTIRYTLQVEGEVLDQGELSYLHGHRNLIPGL EEALEGREEGEAFQAHVPAEKAYGPHDPEGVQVVPLSAFPEDA EVVPGAQFYAQDMEGNPMPLTVVAVEGEEVTVDFNHPLAGKD LDFQVEVVKVREATPEELLHGHAHGGGSRKHHHHHHHH-Ct |
| TtSly Dcas | Nt-MRSKVGQDKVVTIRYTLQVEGEVLDQGELSYLHGHRNLIPGLE EALEGREEGEAFQAHVPAEKAYGAGSGSSGKDLDFQVEVVKV REATPEELLHGHAHGGGSRKHHHHHHHH-Ct |
| TgSly DΔIF | Nt-MKVERGDFVLFNYVGRYENGEVFDTSYESVAREQGIFVEEREY SPIGVTVGAGEIIPGIEEALLGMELGEKKEVVVPPEKGYGATG HPGIIPPHATAIFEIEVVEIKKAGEALEHHHHHHLEHHHHHH-Ct |
| TtSly Dcas-Her3 | Nt-MRSKVGQDKVVTIRYTLQVEGEVLDQGELSYLHGHRNLIPGLE EALEGREEGEAFQAHVPAEKAYGAGSPQPLVYNKLTFQLEPNP HTKGSSGKDLDFQVEVVKVREATPEELLHGHAHGGGSRKHHH HHHHH-Ct |

TABLE 2-continued

| | |
|---|---|
| TtSly<br>Dcys-<br>Her3 | Nt-<br>MRGSKVGQDKVVTIRYTLQVEGEVLDQGELSYLHGHRNLIPGL<br>EEALEGREEGEAFQAHVPAEKAYGPCGPQPLVYNKLTFQLEPN<br>PHTGCGKDLDFQVEVVKVREATPEELLHGHAHGGGSHHHHHH<br>HH-Ct |
| TgSly<br>Dser-<br>Her3 | Nt-<br>MKVERGDFVLFNYVGRYENGEVFDTSYESVAREQGIFVEEREY<br>SPIGVTVGAGEIIPGIEEALLGMELGEKKEVVVPPEKGYGMPS<br>GPQPLVYNKLTFQLEPNPHTGSAGKTAIFEIEVVEIKKAGEAG<br>GGSRKHHHHHHHH-Ct |
| TgSly<br>Dcys-<br>Her3 | Nt-<br>MRGSKVERGDFVLFNYVGRYENGEVFDTSYESVAREQGIFVEE<br>REYSPIGVTVGAGEIIPGIEEALLGMELGEKKEVVVPPEKGYG<br>MPCGPQPLVYNKLTFQLEPNPHTGCAGKTAIFEIEVVEIKKAG<br>EAGGGSHHHHHHHH-Ct |
| TtSly<br>Dcas-<br>Her4 | Nt-<br>MRSKVGQDKVVTIRYTLQVEGEVLDQGELSYLHGHRNLIPGLE<br>EALEGREEGEAFQAHVPAEKAYGAGSPQTFVYNPTTFQLEHNF<br>NAKGSSGKDLDFQVEVVKVREATPEELLHGHAHGGGSRKHHH<br>HHHHH-Ct |
| TtSly<br>Dcys-<br>Her4 | Nt-<br>MRGSKVGQDKVVTIRYTLQVEGEVLDQGELSYLHGHRNLIPGL<br>EEALEGREEGEAFQAHVPAEKAYGPCGPQTFVYNPTTFQLEHN<br>FNAGCGKDLDFQVEVVKVREATPEELLHGHAHGGGSHHHHHH<br>HH-Ct |
| TgSly<br>Dser-<br>Her4 | Nt-<br>MKVERGDFVLFNYVGRYENGEVFDTSYESVAREQGIFVEEREY<br>SPIGVTVGAGEIIPGIEEALLGMELGEKKEVVV<br>PPEKGYGMPSGPQTFVYNPTTFQLEHNFNAGSAGKTAIFEIEV<br>VEIKKAGEAGGGSRKHHHHHHHH-Ct |
| TgSly<br>Dcys-<br>Her4 | Nt-<br>MRGSKVERGDFVLFNYVGRYENGEVFDTSYESVAREQGIFVEE<br>REYSPIGVTVGAGEIIPGIEEALLGMELGEKKEVVVPPEKGYG<br>MPCGPQTFVYNPTTFQLEHNFNAGCAGKTAIFEIEVVEIKKAG<br>EAGGGSHHHHHHHH-Ct |

Example 2 a) Immunisation and Selection of HER3 Antibodies

For the generation of antibodies against the ß-hairpin of HER3 and HER4, Balb/C, NMRI or SJL mice were immunized with different antigens. As antigens the following proteins were used: full length Her3 ECD, or the epitope scaffold proteins TtSlyD-FKBP12-Her3, TtSlyDcys-Her3, TtSlyDcas-Her3, TgSlyDcys-Her3 and TgSlyDser-Her3. The TtSlyD-FKBP12-Her3 variant represents the first generation epitope scaffold, used for generation of Her3 dimerization domain specific antibodies. Although the general principal of using SlyD variants as epitope scaffolds could already be demonstrated using the first generation SlyD-FKBP12 scaffold, improved variants of the scaffold with higher stability were developed. These SlyD variants are derived from *Thermos thermophilus* and *Thermococcus gammatolerans*.

All mice were subjected to 3 immunizations at the time points 0, 6 and 10 weeks after start of the immunization campaign. At each time point each mouse was immunized with 100 µg endotoxin free immunogen dissolved in 100 µl PBS. For the first immunization the immunogen was mixed with 100 µl CFA. For the second and third immunization the immunogen was mixed with IFA. The first and the third immunization were applied via the intraperitoneal route, the second immunization was applied subcutaneously. 2 and 3 days prior to the preparation of spleenocyte for antibody development using hybridoma technology, the mice were subjected to intravenous booster immunizations with 12.5 µg immunogen in 100 µl PBS and without adjuvant.

Titer Analysis

For the determination of serum titers against the respective immunogen and against the screening proteins a small amount of serum of each mouse was collected in week 11 after start of the immunization campaign. For the ELISA the immunogen or the screening scaffold proteins were immobilized on the plate surface. Her3 ECD was immobilized at a concentration of 1 µg/ml and the scaffold proteins TtSlyD-FKBP12-Her3, TtSlyD-FKBP12, TtSlyDcys-Her3, TtSlyD-cas-Her3, TtSlyDcas, TgSlyDcys-Her3, TgSlyDser-Her3 and TgSlyDΔIF were used at a concentration of 0.5 µg/ml. The scaffold proteins TtSlyDcas and TgSlyDΔIF were used as negative controls. The sera from each mouse were diluted in PBS with 1% BSA and the dilutions were added to the plates. The sera were tested at dilutions 1:300, 1:900, 1:2700, 1:8100, 1:24300, 1:72900, 1:218700 and 1:656100. Bound antibody was detected with a HRP-labeled F(ab')$_2$ goat anti-mouse Fcγ (Dianova) and ABTS (Roche) as a substrate.

Even on the level of serum titration it was already obvious that immunized mice developed antibodies against the Her3 ß-hairpin domain. In mice immunized with Her3 ECD this can be shown by titration against one of the scaffold proteins containing the dimerization ß-hairpin loop. The strongly reduced signal can be explained by the fact, that the majority of antibodies raised by immunization with Her3 ECD are targeting other parts within the ECD and only a small fraction is binding to the dimerization ß-hairpin domain. In mice immunized with Her3 dimerization loop containing scaffolds the fraction of antibodies targeting the loop can be shown by titration against Her3 ECD (positive control) and titration against an control scaffold without Her3 insertion (negative control).

b) Antibody Development and ELISA Screening/Selection

The use of the here described epitope scaffold technology offers in principal two strategies for the development of antibodies targeting the Her3 dimerization domain (ß-Hairpins of HER3 (SEQ ID NO: 1)). One strategy is to immunize with the full length Her3 ECD and to use the scaffolds to screen for the dimerization domain specific antibodies. The other strategy is the direct use of the scaffold for immunization and to use the Her3 ECD, a scaffold with another backbone or a scaffold without insertion for counter screening. Antibodies were developed with hybridoma technology by fusing primary B-cells with P3X63Ag8.653 myeloma cells. 2 days after the final booster immunization, immunized mice were sacrificed and spleen cell populations were prepared. The spleenocytes were fused with P3X63Ag8.653 by using the PEG fusion technology. The cellular batch culture from the fusion was incubated overnight at 37° C. under 5% CO$_2$. The following day the cellular batch containing fused cells was centrifuged for 10 min at 400 g. Thereafter, the cells were suspended in hybridoma selection media supplemented with 0.1× azaserine-hypoxanthine (Sigma) and were seeded at a concentration of 2.5×10$^4$ cells per well in 96 well plates. The plates were cultured for at least 1 week at 37° C. under 5% CO$_2$. 3 days prior to ELISA analysis the selection media was changed.

Primary culture supernatants were tested in ELISA against Her3 ECD and various scaffold proteins. The testing against the scaffold proteins was done to demonstrate that the selected clones are binding to the dimerization domain ß-hairpin of native Her3 ECD. The testing against the control scaffolds TtSlyDcas and TgSlyDΔIF was done to show that the selected clones are binding the inserted Her3 derived sequence and not the scaffold backbone. To check for cross reactivity the resulting clones were tested against the full length ECDs of the other members of the Her family namely, Her1, Her2 and Her4. As shown all selected clones are highly specific for Her3 and a highly specific cross reactivity to HER4 could be detected, while no cross reactivity to other members of the Her family were detected. For the ELISA the screening an antigen down format was used. Her3 ECD was immobilized at a concentration of 1 µg/ml and the scaffold proteins TtSlyD-FKBP12-Her3, TtSlyD-FKBP12, TtSlyDcys-Her3, TtSlyDcas-Her3, TtSlyDcas, TgSlyDcys-Her3, TgSlyDser-Her3 and TgSlyDΔIF were immobilized at a concentration of 0.5 µg/ml. Hybridoma Supernatant was added to the plates and incubated for 1 h at room temperature. Bound antibody was detected with a HRP-labeled F(ab')₂ goat anti-mouse Fcγ (Dianova) and ABTS (Roche) was used as a HRP-substrate.

d) DNA Sequencing of Selected Anti-Her3 Hybridoma

To obtain the DNA sequences of the selected hybridoma clones a 5' Race PCR was conducted. For the RT-PCR total RNA was prepared from $5 \times 10^6$ cells by using a total RNA purification kit (Qiagen). The reverse transcription and the PCR were conducted using a 5'prime RACE PCR kit (Roche). The resulting PCR fragments from heavy and light chain were purified by gel electrophoresis and subsequent gel purification. The PCR fragments were cloned using the Topo® Zero-Blunt® cloning kit (Invitrogen) and transformed into competent cells. Several clones from each hybridoma were submitted for sequencing to obtain a consensus sequences for the selected clones. M-05-74 M-15-02 M-15-04 were submitted for sequencing which resulted in identical VH and VL sequences for all 3 clones. M-15-03, M-15-05, M-15-08, M-15-09, M-15-11, M-16-01 were sequenced analogously and also resulted in identical VH and VL sequences for all clones.

TABLE 3

Evaluation of the selected clones by ELISA. The clones were tested against the scaffold proteins TtSlyDcas-Her3, TtSlyDcys-Her3, TgSlyDser-Her3 and TgSlyDcys-Her3 and the full length Her3 ECD to verify their Her3 dimerization domain insert (β-Hairpin of HER3 (SEQ ID NO: 1)) specificity. As negative controls the scaffold proteins TtSlyDcas and TgSlyDΔIF were used. Additionally, clones were tested against full length ECDs of Her1, Her2, Her3 and Her4 to verify potential cross reactivity. Clones show binding to full length Her3 ECD and are cross reactive against full length Her4 ECD.

| Clone | cas | TtSlyD- cas- Her3 | TtSlyD- cys- Her3 | ΔIF | TgSlyD- ser- Her3 | TgSlyD- cys- Her3 | Her1 ECD | Her2 ECD | Her3 ECD | Her4 ECD |
|---|---|---|---|---|---|---|---|---|---|---|
| M-05-74 | 0.023 | 3.133 | 3.150 | 0.020 | 3.159 | 3.159 | 0.018 | 0.020 | 3.152 | 3.170 |
| M-15-02 | 0.040 | 1.763 | 1.522 | 0.040 | 1.980 | 1.785 | 0.024 | 0.025 | 3.153 | 3.192 |
| M-15-03 | 0.045 | 1.772 | 1.850 | 0.039 | 1.628 | 1.461 | 0.020 | 0.024 | 3.171 | 3.234 |
| M-15-04 | 0.040 | 1.847 | 1.457 | 0.033 | 1.833 | 1.500 | 0.067 | 0.064 | 3.175 | 3.186 |
| M-15-05 | 0.041 | 1.443 | 1.482 | 0.046 | 1.886 | 1.485 | 0.020 | 0.021 | 3.156 | 3.216 |
| M-15-08 | 0.041 | 1.569 | 1.707 | 0.040 | 1.746 | 1.532 | 0.019 | 0.023 | 3.195 | 3.181 |
| M-15-09 | 0.057 | 1.870 | 1.929 | 0.076 | 1.799 | 1.640 | 0.024 | 0.037 | 3.234 | 3.200 |
| M-15-11 | 0.044 | 1.714 | 1.636 | 0.056 | 2.005 | 1.693 | 0.029 | 0.031 | 3.103 | 3.218 |
| M-16-01 | 0.039 | 1.653 | 1.793 | 0.037 | 1.860 | 1.637 | 0.024 | 0.032 | 3.184 | 3.212 | c) Immunohistochemistry

Figure 5:
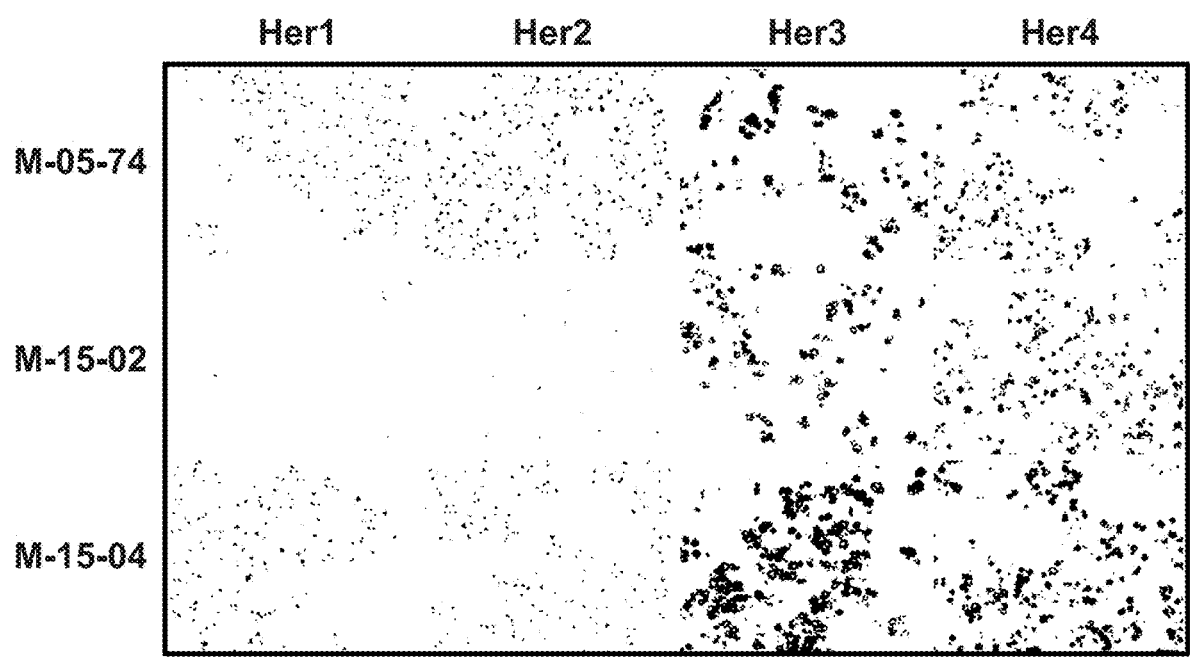
FIG. 5 Testing of specificity and reactivity in IHC of the selected clones. All three clones showed binding to Her3 and cross reactivity against Her4. No cross reactivity against Her1 and Her2 was detectable.

All selected clones were tested for reactivity and specificity in IHC. Therefore HEK293 cells were transiently transfected with plasmids coding for full length HER1, HER2, HER3 or HER4, respectively. 2 days after transfection the different cell lines now expressing HER1, HER2, HER3 or HER4 were harvested, subsequently fixed in formalin and embedded in Agarose for generation of IHC controls. After an additional fixation in formalin overnight the Agarose blocks were embedded in paraffin. Untransfected HEK293 cells were used as negative controls and treated accordingly to the transfected cells. After paraffin embedding 3 µm thin sections were prepared using a microtome. The sections were mounted on glass microscopy slides and dried for 2 h. All further steps of the immunohistochemical staining procedure were carried out using a Ventana Benchmark® XT. The slides were dewaxed and antigen retrieval was performed by applying heat for 1 hour. For antigen retrieval the Ventana buffer CC1 was used. The antibodies were used at a concentration of 1 µg/ml. For the detection of bound antibody the Ventana UltraView™ detection kit was used. Results are shown in FIG. 5. All three clones showed binding to HER3 and cross reactivity against HER4. No cross reactivity against HER1 and HER2 was detectable.

e) Time Dependent Internalization Analyses of M-05-74 Via FACS

Binding and internalization of HER3 by the selected clone M-05-74 to HER3 was analyzed in FACS using the HER3 expressing tumor cell line T47D. $5 \times 10^5$ cells were treated with 50 ng Recombinant Human Heregulin fragment (HRG) (SEQ ID NO: 11). The fragment including amino acid of SEQ ID NO: 11 was cloned in pCDNA.1 vector (Invitrogen). The HRG fragment was expressed in FreeStyle™ 293-F cells according to the protocol described by Invitrogen. (FreeStyle™ 293 Expression system Catalog no. K9000-01). Purified HRG fragment was solved in 20 mM Histidin, 140 mM NaCl; pH6.0 and stored by −80 C.

Figure 6:
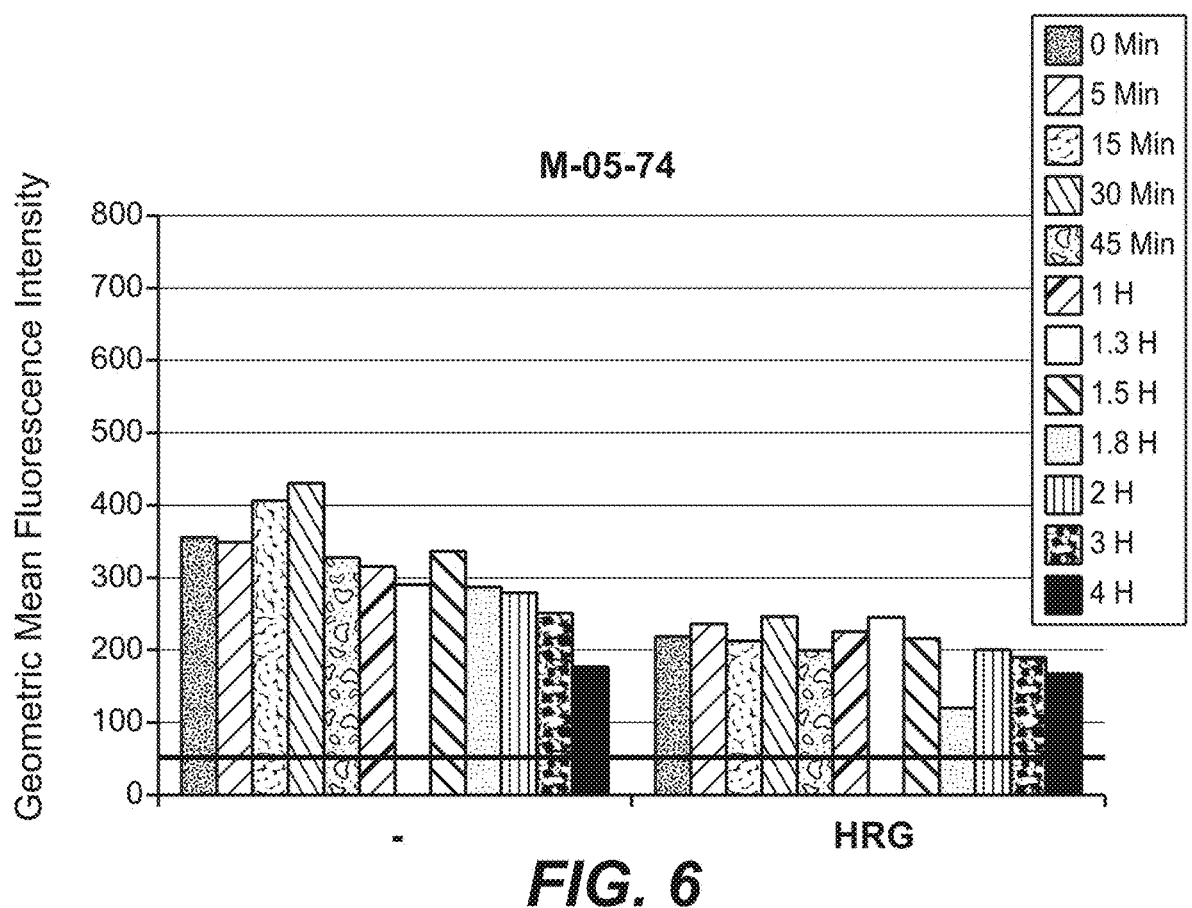
FIG. 6 FACS analysis of M-05-74 antibody induced time dependent HER3 internalization in T47D cells.

Untreated (−) cells were used as negative controls. Shortly after Heregulin induced activation, 1 µg of M-05-74 was added to the cells. The cells were incubated for 0, 5, 15, 30, 45, 60, 75, 90, 105, 120, 180 or 240 min at 37° C. After incubation the cells were immediately put on ice. The cells were washed with 3 ml FACS buffer once and then stained for 30 minutes with 1 µg of a R-Phycoerythrin Goat Anti-Mouse IgG (H+L) secondary antibody. Flow cytometry was carried out using a FACSCanto™ flow cytometer (BD Biosciences). Results are FACS analysis of M-05-74 induced, time dependent HER3 receptor internalization in T47D cells. M-05-74 shows binding to the expressed HER3 ECD, with or without supplemented recombinant human Heregulin fragment (HRG). M-05-74 leads to Her3 receptor internalization over a 4 h time period. Results are shown in FIG. 6. The isotype control is indicated as a constant horizontal black bar. M-05-74 shows binding to the expressed Her3 ECD, with or without Human Heregulin fragment (−) and (+HRG). M-05-74 leads to Her3 receptor internalization over a 4 h time period. The isotype control is indicated as a constant horizontal black bar. In the presence of HRG the antibody induced internalization of HER3 was faster (e.g after 1 h, at least 25% more HER3 were internalized in the presence of HRG (+HRG) when compared to the value in the absence of HRG (−).

Example 3 a) Kinetic Screening/Binding Properties of HER3 Antibodies

The kinetic screening was performed according to Schraeml et al. (Schraml, M. and M. Biehl, Methods Mol Biol 901 (2012) 171-181) on a Biacore™ 4000 instrument, mounted with a Biacore™ CM5 sensor. In all assay the test antibodies were captured. The system was under the control of the software version V1.1. The instrument buffer was HBS-EP (10 mM HEPES (pH 7.4), 150 mM NaCl, 1 mM EDTA, 0.05% (w/v) P20). The system operated at 25° C. 30 μg/ml Rabbit polyclonal antibody (RAM IgG, (Rabbit anti Mouse IgG with Fc gamma specificity) GE Healthcare) in 10 mM sodium acetate buffer (pH 4.5) was immobilized using EDC/NHS chemistry according to the manufacturer's instructions on the spots 1, 2, 4 and 5 in the flow cells 1, 2, 3 and 4. The sensor was saturated using 1M ethanolamine. In each flow cell, referenced signals were calculated using spots 1-2 and spots 5-4, spot 3 served as a blanc control. The antigen (human recombinant Her-3 ECD (68 kDa), and recombinant *Thermus thermophilus* SlyD FKBP-Her3 (15 kDa) comprising the ß-hairpin peptide of HER3 (SEQ ID NO:1)) was diluted at 150 nM in instrument buffer supplemented with 1 mg/ml CMD(Carboxymethyldextran, Sigma). to suppress unspecific binding. Prior to their application the hybridoma culture supernatants were diluted 1:5 in instrument buffer. The diluted mixtures were injected at a flow rate of 30 μl/min for 2 min. The antibody capture level (CL) in response units was monitored. Immediately thereafter the respective antigen was injected at a flow rate of 30 μl/min for 3 min association time. Thereafter, the antibody-antigen complex dissociation signal was recorded for 5 min. The sensor was regenerated by injecting a 10 mM glycine-HCl solution (pH 1.7) for 2 min at a flow rate of 30 μl/min. The recorded signal shortly before the end of the injection of the antigen was denoted as binding late (BL) in response units. The recorded signal shortly before the end of the recording of the dissociation is denoted as stability late (SL) in response units. The dissociation rate constants were determined calculated The antibody-antigen complex stability in minutes was calculated with the following formula: $\ln(2)/60*kd$. The Molar Ratio was calculated with the formula: MW (antibody)/MW (antigen) *BL (antigen)/CL (antibody).

Binding Late (BL) represents the response units at the end of the analyte injection. The amount of antibody captured as a ligand on the sensor surface is measured as Capture Level (CL) in response units. Together with the information of the molecular weights of the tested analytes, the antibody and the analyte in solution, the Molar Ratio can be calculated. In case the sensor was configured with a suitable amount of antibody ligand capture level, each antibody should be able to functionally bind at least to one analyte in solution, which is represented by a Molar Ratio of MR=1.0. Then, the Molar Ratio is also an indicator for the valence mode of analyte binding. The maximum valence can be MR=2 for an antibody binding two analytes, one with each Fab valence. In case of steric limitations or a dysfunctional analyte binding, the Molar Ratio can indicate understoichiometric binding, like it is the case when the Her-3 ECD is being bound in its "closed" conformation. The maximum assay deviation in the determination of the Molar Ratio is MR=0.2.

Screening/Selection of Anti-HER3/HER4 Antibody M-05-74:

In one experiment, the kinetic screening was driven with hybridoma primary cultures from different fusions, which were obtained from an immunization of mice with human recombinant Her-3 ECD. The aim was to select cultures with binding specificity for the Her-3 heterodimerization domain ß-hairpin peptide (SEQ ID NO:1). As antigens in solution human recombinant Her-3 ECD (68 kDa), and recombinant *Thermus thermophilus* SlyD FKBP-Her3 (15 kDa) comprising the ß-hairpin peptide of HER3 (SEQ ID NO:1) were used. A positive hit was classified as a primary culture supernatant with binding activity versus both antigens.

The Table 4 exemplarily shows primary culture supernatants, from which M-05-74 fulfills these requirements, indicating epitope specificity for the ß-hairpin of HER3. Therefore this is a suitable method of screening of anti-HER3 antibodies which bind to the Her-3 hairpin of SEQ ID NO:1.

TABLE 4

Exemplary results obtained from a kinetic screening experiment with a set of hybridoma primary cultures from fusions, wherein antibody M-05-74 was identified as binding to both HER3 ECD and the β-hairpin of HER3 (SEQ ID NO: 1) within the thermo SlyD-Her3 construct.

| Ligand | Analyte | binding late BL [RU] | stability late SL [RU] | kd [1/s] | t/2 diss [min] | T [° C.] | CL [RU] | MR [—] |
|---|---|---|---|---|---|---|---|---|
| M-04-06 | human-Her3-ECD | 17 | 16 | 4.13E−04 | 28 | 25 | 134 | 0.3 |
| M-04-06 | thermo SlyD-Her3 | −4 | −4 | n.d. | n.d. | 25 | 134 | −0.3 |
| M-04-140 | human-Her3-ECD | −1 | 1 | n.d. | n.d. | 25 | 110 | 0.0 |
| M-04-140 | thermo SlyD-Her3 | −6 | −5 | n.d. | n.d. | 25 | 112 | −0.5 |
| M-05-20 | human-Her3-ECD | 32 | 33 | 4.98E−05 | 232 | 25 | 623 | 0.1 |
| M-05-20 | thermo SlyD-Her3 | −9 | −6 | n.d. | n.d. | 25 | 625 | −0.1 |
| M-05-30 | human-Her3-ECD | 122 | 123 | 3.74E−05 | 309 | 25 | 521 | 0.5 |
| M-05-30 | thermo SlyD-Her3 | −3 | −2 | n.d. | n.d. | 25 | 525 | −0.1 |
| M-05-44 | human-Her3-ECD | 55 | 55 | 3.42E−05 | 337 | 25 | 373 | 0.3 |
| M-05-44 | thermo SlyD-Her3 | −7 | −6 | n.d. | n.d. | 25 | 369 | −0.2 |

TABLE 4-continued

Exemplary results obtained from a kinetic screening experiment with a set of hybridoma primary cultures from fusions, wherein antibody M-05-74 was identified as binding to both HER3 ECD and the β-hairpin of HER3 (SEQ ID NO: 1) within the thermo SlyD-Her3 construct.

| Ligand | Analyte | binding late BL [RU] | stability late SL [RU] | kd [1/s] | t/2 diss [min] | T [° C.] | CL [RU] | MR [—] |
|---|---|---|---|---|---|---|---|---|
| M-05-74 | human-Her3-ECD | 75 | 79 | <1.00E−05 | >1155 | 25 | 318 | 0.5 |
| M-05-74 | thermo SlyD-Her3 | 33 | 32 | 1.20E−04 | 96 | 25 | 315 | 1.1 |
| M-05-82 | human-Her3-ECD | 0 | 1 | n.d. | n.d. | 25 | 205 | 0.0 |
| M-05-82 | thermo SlyD-Her3 | −4 | −5 | n.d. | n.d. | 25 | 204 | −0.2 |

It has been found that M-05-74 shows a reduced Molar Ratio in its binding to the human Her-3 ECD analyte (MR=0.5), whereas in its binding to analyte *Thermus thermophilus* SlyD FKBP-Her3 comprising the ß-hairpin HER3 (SEQ ID NO:1) M-05-74 shows an improved Molar Ratio (MR=1.1), indicating a functional, stoichiometric 1:1 binding with improved epitope accessibility (compared to human Her-3 ECD).

b) Kinetics of HER3 Antibodies M-05-74, M-205 and M-208 Kinetics to Investigate the Mode of Action of M-05-74 in the Absence and Presence of Heregulin (HRG)

In its equilibrium state, the Her-3 ECD is in its "closed confirmation", which does mean, the heterodimerization Her-3 beta-hairpin motive is tethered via non-covalent interactions to the Her-3 ECD domain IV (see FIGS. 1c and d). It is supposed, that the "closed" Her-3 conformation can be opened via the binding of the ligand heregulin at a specific Her-3 heregulin binding site. This takes place at the Her-3 interface formed by the Her-3 ECD domains I and domain III. By this interaction it is believed, that the Her-3 receptor is activated and transferred into its "open conformation" (see FIGS. 1b and e). When this occurs, the Her-3 beta-hairpin is accessible for the described antibodies. This mode of action can be simulated in vitro by a Biacore™ experiment.

A Biacore™ T100 instrument (GE Healthcare) was used to kinetically assess the monoclonal antibodies for their behavior to the heregulin-activated Her-3 Extracellular Domain (Her3_ECD). A CM5 series sensor was mounted into the system and was normalized in HBS-ET buffer (10 mM HEPES pH 7.4, 150 mM NaCl, 3 mM EDTA, 0.005% w/v Tween 20) according to the manufacturer's instructions. The sample buffer was the system buffer supplemented with 1 mg/ml CMD (Carboxymethyldextran, Sigma #86524). The system operated at 25° C. 6500 RU RAM-Fcγ (relative units of Fcγ-fragment RamIgG, GE Healthcare) were immobilized according to the manufacturer's instructions using EDC/NHS chemistry on all four flow cells. The sensor was deactivated using 1M ethanolamine.

The binding activity of the respective antibody against the analytes was kinetically tested. Antibodies were captured at 35 nM concentration by a 1 min injection at 5 μl/min. The flow rate was set to 100 μl/min.

The analytes in solution tested were human Heregulin fragment (HRG) (SEQ ID NO:11), a 44 kDa homodimeric protein (prepared according to Example 2e), human recombinant HER2 ECD (SEQ ID NO:10) (69.6 kDa), human recombinant HER3 ECD (SEQ ID NO:4) (68 kDa), human recombinant HER4 ECD (SEQ ID NO:6), and 100 nM of the Her-3 ECD and the Her-4 ECD each incubated with a 5-fold molar excess of Heregulin for 60 min at room temperature resulting in HER3 ECD-HRG complex and HER4 ECD-HRG complex (Addition of MWs for complexes).

Analytes in solution were injected at different concentration steps of 0 nM, 1.1 nM, 3.7 nM, 11.1 nM, 33.1 nM and 90 nM for 3.5 min. The dissociation was monitored for 15 min. Where possible, kinetic signatures were evaluated according to a Langmuir fit.

TABLE 5a

SPR-resolved kinetic data of M-05-74 (=M-074), M-205 and M-208

| Antibody | CL RU | Analyte in solution | T ° C. | $k_a$ 1/Ms | $k_d$ 1/s | $K_D$ M | $K_D$ nM | BL RU | MR | Chi² RU² |
|---|---|---|---|---|---|---|---|---|---|---|
| M-074 | 535 | HRG | 25 | n.d. | n.d. | n.d. | n.d. | n.d. | n.d. | n.d. |
| M-074 | 530 | HER2_ECD | 25 | n.d. | n.d. | n.d. | n.d. | n.d. | n.d. | n.d. |
| M-074 | 648 | HER3-ECD | 25 | 1.3E+04 | 2.8E−05 | 2.2E−09 | 2 | 70 | 0.2 | 0.1 |
| M-074 | 712 | HER4-ECD | 25 | 6.7E+03 | 1.0E−03 | 1.5E−07 | 150 | 27 | 0.1 | 0.1 |
| M-074 | 546 | HER3-ECD-HRG | 25 | 6.3E+04 | 2.7E−04 | 4.2E−09 | 4 | 160 | 0.6 | 2.3 |
| M-074 | 719 | HER4-ECD-HRG | 25 | 1.6E+05 | 8.3E−04 | 5.2E−09 | 5 | 349 | 0.6 | 0.0 |
| M-205 | 591 | HRG | 25 | n.d. | n.d. | n.d. | n.d. | n.d. | n.d. | n.d. |
| M-205 | 588 | HER2_ECD | 25 | n.d. | n.d. | n.d. | n.d. | n.d. | n.d. | n.d. |
| M-205 | 605 | HER3-ECD | 25 | 4.9E+04 | 1.0E−04 | 2.0E−09 | 2 | 235 | 1.0 | 1.3 |
| M-205 | 597 | HER3-ECD-HRG | 25 | 3.7E+04 | 1.2E−04 | 3.2E−09 | 3 | 164 | 0.4 | 0.3 |
| M-208 | 777 | HRG | 25 | n.d. | n.d. | n.d. | n.d. | n.d. | n.d. | n.d. |
| M-208 | 771 | HER2_ECD | 25 | n.d. | n.d. | n.d. | n.d. | n.d. | n.d. | n.d. |
| M-208 | 822 | HER3-ECD | 25 | 5.8E+04 | 5.3E−05 | 9.1E−10 | 1 | 367 | 1.0 | 9.4 |

TABLE 5a-continued

SPR-resolved kinetic data of M-05-74 (=M-074), M-205 and M-208

| Antibody | CL RU | Analyte in solution | T °C. | $k_a$ 1/Ms | $k_d$ 1/s | $K_D$ M | $K_D$ nM | BL RU | MR | Chi² RU² |
|---|---|---|---|---|---|---|---|---|---|---|
| M-208 | 795 | HER3-ECD-HRG | 25 | 5.0E+04 | 1.4E−04 | 2.8E−09 | 3 | 390 | 1.1 | 17.6 |

MR = Molar Ratio, BL = Binding Late, CL = Capture Level; n.d. = not detectable = no binding The Molar Ratio was calculated with the formula: MW (antibody)/MW(antigen) *BL (antigen)/CL (antibody).

The antibody M-205 is a murine monoclonal antibody with binding activity versus an epitope nearby the Her-3 ECD Heregulin binding site (described as Mab205.10.2 in WO2011/076683). M-205 competes with Heregulin around its binding site on the Her-3 ECD.

The antibody M-208 is a murine monoclonal antibody with binding activity versus the Her-3 ECD domain IV. M-208 binds to the Her-3 ECD independently of the Her-3 ECD conformational state.

M-05-74 (=M-074 in Table 5) binds to the Her-3 ECD in its active "open" conformation (on the presence of ligand (e.g. heregulin HRG) with improved kinetics, due to a better accessibility of the Her-3 hairpin in its "open" conformation. The MR is at least two fold higher.

No antibody binding (n.d.) was observed versus the negative control analytes Heregulin beta (HRG) and the extracellular HER-2 domain (HER2_ECD). The tested antibodies showed all binding to the Her3-ECD (HER3_ECD), but with strongly differing BL values.

M-05-74 binds to the Her-3 ECD in its "closed" conformation with slower association rate constant $k_a$=1.3E+04 1/Ms and smaller BL (70 RU) than when compared to the clones M-205 with faster $k_a$=4.9 E+04 1/Ms and high signal amplitude at BL (235 RU) and M-208 with faster $k_a$=5.8E+04 1/Ms and also high signal amplitude at BL (367RU). This implicates on the stoichiometry of the binding (MR), where M-205 (MR=1.0) and M-208 (MR=1.0) both show a functional 1:1 binding for the HER3-ECD, whereas M-05-74 shows a non-functional binding (MR=0.2). Here it is supposed, that this interaction of M-05-74 versus the Her-3 ECD is residual binding of a portion of structurally handicapped Her-3 ECD analyte. This is also supposed for the interaction of M-05-74 versus the Her-4 ECD, which also shows a non-functional binding with BL (27 RU) and (MR=0.1).

A surprising result is the more than 4-fold increase (nearly 5 fold) of the M-05-74 association rate constant $k_a$ from the "closed" Her-3 ECD to the "open" Her-3 ECD/Heregulin complex; from $k_a$=1.3E+04 1/Ms (Her3 ECD) to $k_a$=6.3E+04 1/Ms (Her3-ECD-HRG). So M-05-74 binds to HER3-ECD with a ratio of the association constant ($K_a$) in presence of Heregulin (Ka (+Heregulin)) and absence of Heregulin (Ka (-Heregulin)) of 4.0 or higher (Ka (+Heregulin))/(Ka (−Heregulin)=ka (Her3-ECD-HRG)/ka (Her3-ECD)=6.3E+04 [1/Ms]/1.3E+04 [1/Ms])=4.85)). Thereby the Molar Ratio improves 3-fold, indicating now a 1:1 interaction of M-05-74 with the Her-3 ECD Heregulin complex. Thus binds M-05-74 to HER3-ECD with a ratio of the Molar Ratio MR of binding in presence of Heregulin (MR (+Heregulin)) and in absence of Heregulin (MR (−Heregulin)) of 3.0 (MR (+Heregulin))/(MR (−Heregulin)=0.6/0.2=3).

This is also valid for the Her-4 ECD/Heregulin complex, where the Molar Ratio improves 6-fold, indicating a 1:1 interaction of M-05-74 with the Her-4 ECD Heregulin complex. Thus binds M-05-74 to HER4-ECD with a ratio of the Molar Ratio MR of binding in presence of Heregulin (MR (+Heregulin)) and in absence of Heregulin (MR (−Heregulin)) of 3.0 (MR (+Heregulin))/(MR (−Heregulin)=0.6/0.1=6). And furthermore surprisingly the M-05-74 association rate constant ka increases from the "closed" Her-4 ECD to the "open" Her-4 ECD/Heregulin complex from ka=6.7E+03 1/Ms (Her3_ECD) to ka=1.6E+05 more than 20-fold. So M-05-74 binds to HER4-ECD with a ratio of the association constant (Ka) in presence of Heregulin (Ka (+Heregulin)) and absence of Heregulin (Ka (−Heregulin)) of 20.0 or higher (Ka (+Heregulin))/(Ka (−Heregulin)=ka (Her4-ECD-HRG)/ka (Her4-ECD)=6.7E+04 [1/Ms]/1.6E+05 [1/Ms])=23.88)).

As expected, the Heregulin displacer M-205, reduces its BLvalue and the Molar Ratio. The Molar Ratio is decreased 2.5-fold, from a fully functional 1:1 interaction with MR=1.0 (Her3-ECD) with 235 RU at BL into a less functional MR=0.4 (Her3-ECD-HRG) with 164 RU at BL. This indicates the loss in functionality due to the competing presence of excess Heregulin.

The antibody M-208, which binds to the Her-3 ECD domain IV remains completely unaffected by the presence of Heregulin. No significant change of the Molar Ratios MR could be detected.

Figure 7:
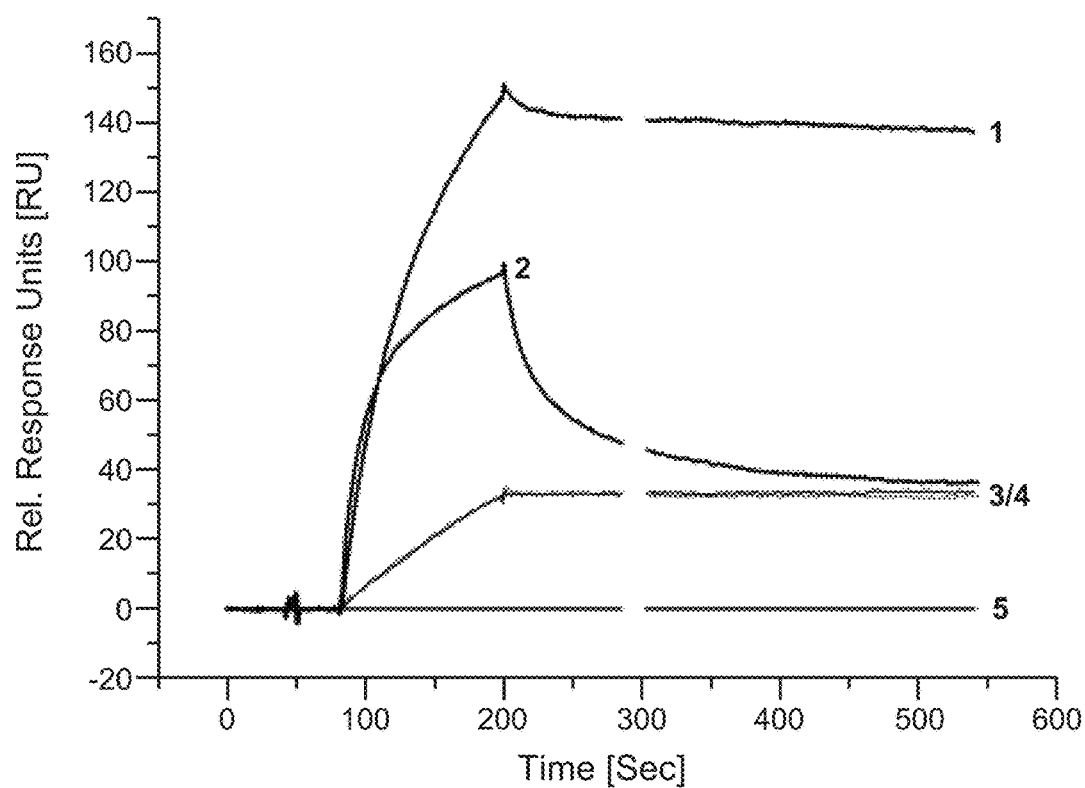
FIG. 7 Biacore™ sensorgram overlay plot. 1: 100 nM M-05-74*Heregulin/Her-3 ECD interaction. 2: 100 nM M-08-11*Heregulin/Her-3 ECD interaction. 3&4: 100 nM M-05-74 and 100 nM M-08-11*Her-3 ECD interaction. 5: buffer reference.

The FIG. 7 shows the mode of binding of the anti-HER3/HER4 ß-hairpin antibody M-05-74 to the Heregulin-activated Her-3 ECD complex. M-05-74 (see plot 1) captures and prevents the Heregulin dissociation from the complex. M-05-74 is a trap for Heregulin ("Heregulin-sink"). M-05-74 does not compete with Heregulin for a binding site on the Her-3 ECD. For comparison M-08-11 (plot 2) is shown; M-08-11 (VH and VL see SEQ ID NO: 51 and 52) is another HER3 ß-Hairpin binder with no HER4 ECD and HER4 ß-hairpin crossreactivity, which binds to a different epitope than M-05-74.

Ia further experiment also HER1 ECD, T.T.SlyD-cysHer3 and T.T.SlyD-cas without the HER3 ß-hairpin were included in the measurement—results are shown in Table 5b, which substantially reveals the same binding properties of M-05-74.

A Biacore™ T200 instrument (GE Healthcare) was mounted with a CM5 series sensor. The sensor was normalized in HBS-ET buffer (10 mM HEPES pH 7.4, 150 mM NaCl, 3 mM EDTA, 0.05% w/v Tween 20) according to the manufacturer's instructions. The sample buffer was the system buffer supplemented with 1 mg/ml CMD (Carboxymethyldextran, Sigma #86524). The system operated at 25° C. 6500 RU RAM-Fcγ (relative units of Fcγ-fragment RamIgG, GE Healthcare) were immobilized according to the manufacturer's instructions using amine coupling EDC/NHS chemistry on all four flow cells. The sensor was deactivated using 1M ethanolamine. Monoclonal antibodies were captured (CL, Capture Level) on the sensor surface by a 1 min injection at 10 µl/min. Concentration dependent kinetics were measured. A concentration series of the analytes HER-1-ECD, HER-2-ECD, HER-3-ECD, HER-4-ECD, T.T.SlyD-cysHer3 and T.T.SlyD-cas were injected each at 0 nM, 1.1 nM, 3.3 nM, 2×10 nM, 30 nM and 90 nM. Heregulin beta (HRG) was injected at 0 nM, 17 nM, 2×50 nM, 150 nM and 450 nM, 90 nM HER-3 ECD and 90 nM HER-4 ECD were preincubated for 2 hrs with a five-fold molar excess of HRG beta and were injected at HER concentrations steps of 0 nM, 1.1 nM, 3.3 nM, 2×10 nM, 30 nM and 90 nM. All analytes were injected for 5 min association time and 10 min dissociation time at 100 µl/min flow rate. The sensor capture system was regenerated by a 3 min injection at 10 µl/min of 10 mM glycine pH 1.7. Where possible kinetic data was evaluated using the Biacore™ T200 evaluation software. HER-3-ECD, HER-4-ECD and T.T.SlyD-cysHer3 kinetics were evaluated using a Langmuir fitting model. HER-3-ECD-HRG and HER-4-ECD-HRG kinetics of M-5-74, were evaluated according to a Langmuir fitting model.

and d) M-08-11; another HER3 ß-Hairpin binder with no HER4 ECD and HER4 ß-hairpin crossreactivity) was injected for 3 minutes at 30 µl/min. Acidic regeneration of the sensor surface was achieved using three consecutive injections of 10 mM Glycine pH 1.7 at 30 µl/min for 60 sec.

Figure 8:
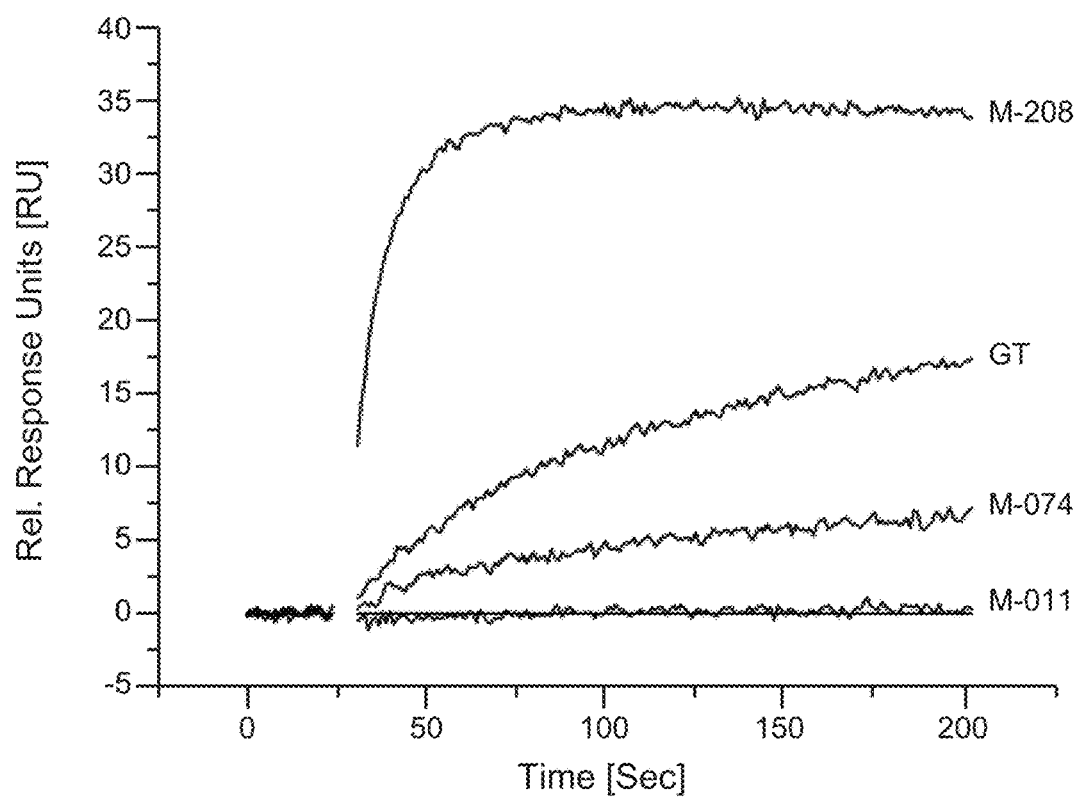
FIG. 8 Sensorgram overlay of the Biacore™ epitope-binning experiment. The primary antibody M-05-74 (M-074 in the Figure) presented the Her-3 ECD to the secondary antibodies M-208, GT (=8B8), M-05-74 and M-08-11 (M-011 in the FIG. 8) (M-. The noise of the measurement was 5 RU.

The noise of the measurement is defined by the rebinding of the secondary M-05-74 injection, which re-saturates the already dissociated primary M-05-74. The experiment showed (see FIG. 8), that M-208 and M-05-74 occupy distinct epitopes on the Her-3 ECD, because the secondary M-208 signal completely saturates the Her-3 ECD in the presence of M-05-74. M-08-11 binding is completely blocked by the presence of M-05-74. The M-08-11 secondary signal is even below noise.

Nevertheless M-08-11 binds to a different epitope than M-05-74 as M-08-11 does not bind to human HER4 ECD TABLE 5b SPR-resolved kinetic data of M-05-74

| Antibody | Analyte in solution | CL (Ab) RU | $k_a$ 1/Ms | kd 1/s | $K_D$ M | RMax RU | MR | Chi$^2$ RU$^2$ | T °C. |
|---|---|---|---|---|---|---|---|---|---|
| M-5-74 | HER1-ECD | 288 | n.d. | n.d. | n.d. | 1 | n.d. | 0 | 25 |
|  | HER2-ECD | 287 | n.d. | n.d. | n.d. | 1 | n.d. | 0 |  |
|  | HER3-ECD | 289 | 9.6E+04 | 1.1E−04 | 1.1E−09 | 19 | 0.1 | 0.05 |  |
|  | HER4-ECD | 285 | 1.6E+04 | 8.2E−04 | 5.1E−08 | 13 | 0.1 | 0.01 |  |
|  | HER3-ECD-HRG | 312 | 1.0E+05 | 2.9E−04 | 2.8E−09 | 195 | 0.8 | 2.2 |  |
|  | HER4-ECD-HRG | 301 | 9.9E+04 | 8.1E−04 | 8.1E−09 | 179 | 0.8 | 1.8 |  |
|  | HRG | 301 | n.d. | n.d. | n.d. | 0 | n.d. | 0.0 |  |
|  | T.T.SlyD-cysHer3 | 486 | 3.0E+04 | 2.4E−04 | 7.8E−09 | 88 | 1.9 | 0.02 |  |
|  | T.T.SlyD-cas | 490 | n.d. | n.d. | n.d. | 0.5 | 0.0 | 0.06 |  |

MR = Molar Ratio, BL = Binding Late, CL = Capture Level; n.d. = not detectable = no bindingM-05-74 binds HER-3-ECD-HRG and HER-4-ECD-HRG with 1:1 stoichiometry and inactive HER-3-ECD and HER-4-ECD with 10:1 stoichiometry. M-05-74 binds HER-3-ECD and HER-3-ECD-HRG with higher affinity than HER-4-ECD and HER-4-ECD-HRG. M-05-74 does not interact with HER-1, HER-2 and HRG. M-05-74 binds T.T.SlyD-cysHer3 with 1:2 stoichiometry and does not interact with T.T.SlyD-cas.

Example 4

Epitope Mapping of Anti-HER3 Antibody M-05-74 and Mode of Action Analysis
M-05-74 with a Unique Epitope (ß-Hairpin of HER3 and HER4)

A Biacore™ 2000 (GE Healthcare) instrument was used to assess the accessible epitopes clone culture supernatants for their binding specificity. A CM5 sensor was mounted into the system and was normalized in HBS-ET buffer (10 mM HEPES pH 7.4, 150 mM NaCl, 3 mM EDTA, 0.005% w/v Tween 20) according to the manufacturer's instructions. The sample buffer was the system buffer supplemented with 1 mg/ml CMD (Carboxymethyldextran, Sigma). The system operated at 37° C. 10000 RU RAM-Fcγ (relative units of Fcγ-fragment Rabbit Anti-Mouse IgG/Jackson Laboratories) were immobilized according to the manufacturer's instructions using EDC/NHS chemistry on all four flow cells. The sensor was deactivated using 1M ethanolamine.

At a flow rate of 10 µl/min the primary antibody 50 nM anti-HER3 M-05-74 was captured for 1 min on all flow cells. The flow rate was set to 30 µl/min and an IgG blocking solution (50 µg/ml IgG (20:2:1 IgG1-Fcγ, IgG2a-Fcγ, IgG2b), Roche) was injected for 5 minutes. The antigen Her-3 ECD was injected at 1.5 µM for 3 min.

Afterwards, 100 nM of each anti-HER3 secondary antibodies (a) M-05-74 b) 8B8 from WO97/35885 (named GT in the Figure) c) M-208 which binds to domainIV of HER3, and HER4 ß-hairpin. (see also below the exact epitope mapping data with the ß-hairpins of HER3 and HER4). The 8B8 (=GT) secondary antibody produces a significant signal in the presence of M-05-74, which is above noise. Therefore the 8B8 (=GT) antibody binds another epitope than M-05-74 and M-08-11.

M-05-74 with Unique Epitope and Mode of Actions

A Biacore™ B3000 instrument (GE Healthcare) was used to kinetically assess the clone culture M-05-74 and the antibody 8B8 (from WO 97/35885, named GT in the Figures) to the "closed" conformation of Her-3 ECD and the "open", Heregulin-activated Her-3 ECD. A CM5 series sensor was mounted into the system and was normalized in HBS-ET buffer (10 mM HEPES pH 7.4, 150 mM NaCl, 3 mM EDTA, 0.005% w/v Tween 20) according to the manufacturer's instructions. The sample buffer was the system buffer supplemented with 1 mg/ml CMD (Carboxymethyldextran). The system operated at 25° C. 10000 RU RAM-Fcγ (relative units of Fcγ-fragment Rabbit Anti-Mouse IgG/Jackson Laboratories) were immobilized according to the manufacturer's instructions using EDC/NHS chemistry on all flow cells. The sensor was deactivated using 1M ethanolamine. Analytes in solution were injected at 100 µl/min at different concentration steps of 0 nM, 1.1 nM, 3.7 nM, 11.1 nM, 33.1 nM and 90 nM for 2 min. The dissociation was monitored for 5 min. Acidic regeneration of the sensor surface was achieved using three consecutive injections of 10 mM Glycine pH 1.7 at 30 μl/min for 60 sec. Kinetic data were evaluated according to a Langmuir fit.

TABLE 6

Langmuir kinetics of M-05-74 in comparison to 8B8 (GT). 8B8 with lower antigen complex stability (t/2diss) and less functionality (MR).

| Antibody | CL (RU) | Analyte in solution | T (° C.) | ka (1/Ms) | t/2-diss (min) | BL (RU) | MR | Chi² (RU²) |
|---|---|---|---|---|---|---|---|---|
| 8B8 | 339.3 | ECD-HRG | 25 | 3.21E+05 | 0.8 | 90 | 0.4 | 2.57 |
| M-074 | 314.7 | ECD-HRG | 25 | 6.6E+04 | 18 | 199 | 0.8 | 0.773 |
| 8B8 | 347.3 | Her-3 ECD | 25 | 1.02E+05 | 5.3 | 13.1 | 0.1 | 0.12 |
| M-074 | 318.2 | Her-3 ECD | 25 | 2.04E+04 | 28 | 36 | 0.2 | 0.122 |
| 8B8 | 476.1 | ttSlyD-Her3 | 25 | n.d. | n.d. | n.d. | n.d. | n.d. |
| M-074 | 468 | ttSlyD-Her3 | 25 | 8.75E+04 | 4.9 | 68.1 | 1.5 | 0.174 |

MR = Molar Ratio, BL = Binding Late, CL = Capture Level

In the table above kinetic data of the antibody clone M-05-74 and the antibody 8B8 are listed. M-05-74 binds to the Heregulin-activated Her-3 ECD with high functionality MR=0.8. M-05-74 and acts as Heregulin trap. (see also Biacore™ sensogram Example 3b and FIG. 7).

The complex stability of the 8B8 antibody with t1/2 diss=0.8 min is weak. 8B8 binds with an, MR=0.4. No separated dissociation phases of the 8B8 antibody and the Heregulin dissociation can be identified. Heregulin completely dissociates off in the same timeframe and with the same velocity, like 8B8. 8B8 antibody does not delay the heregulin dissociation.

M-05-74 functionally binds (MR=1.5) to the *Thermus thermophilus* SlyD FKBP-Her3 comprising th HER3 ß-Hairpin of SEQ ID NO:1 with KD=27 nM. Since the antibody 8B8 does not bind to the HER3 ß-Hairpin comprising *Thermus thermophilus* SlyD FKBP-Her-3 fusion polypeptide this antibody targets another epitope than M-05-74.

Figure 9:
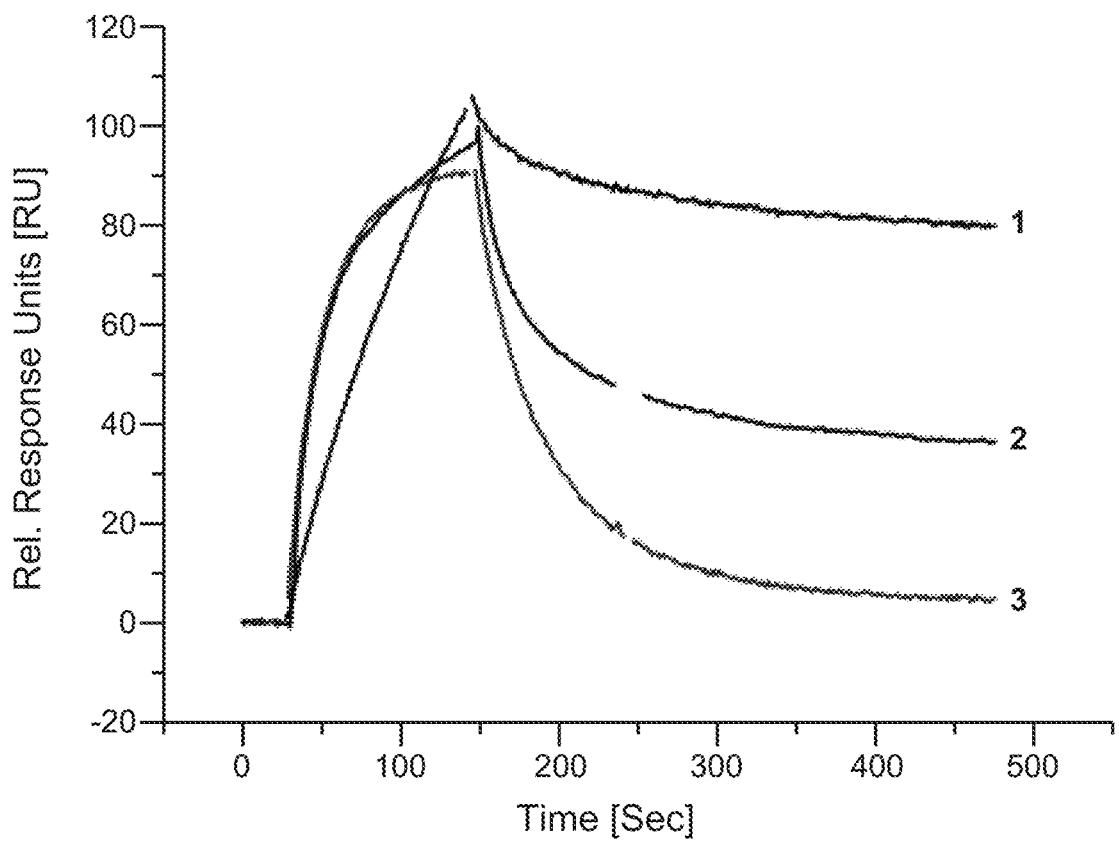
FIG. 9 Biacore™ sensorgram overlay plot. 1: 90 nM Heregulin*Her-3 ECD complex on M-05-74. 2: 90 nM Heregulin*Her-3 ECD complex on M-08-11. 3: 90 nM Heregulin*Her-3 ECD complex on 8B8 antibody.

FIG. 9 is an overlay plot of the Biacore™ sensogramms of anti-HER3/HER4 antibody M-05-74, anti-HER3 antibody M-08-11 and anti-HER3 antibody 8B8 (from WO97/35885) showing the different binding modes of actions. Anti-HER3/HER4 antibody M-05-74 traps the Heregulin-activated Her-3 ECD (1) with t1/2 diss=18 min and acts Heregulin-sink. Anti-HER3 antibody M-08-11 HER3 (ß-Hairpin binder with no HER4 ECD and HER4 ß-hairpin crossreactivity) delays the Heregulin dissociation (2) and produces a complex two-state kinetic. 8B8 antibody (3) is does not trap Heregulin and also not delays the Heregulin dissociation from the Her-3 ECD/Heregulin complex. Since it is a perfect Langmuir interaction, the Heregulin/Her-3 ECD complex quickly and completely dissociates as intact complex from the 8B8 antibody.

Figure 10:
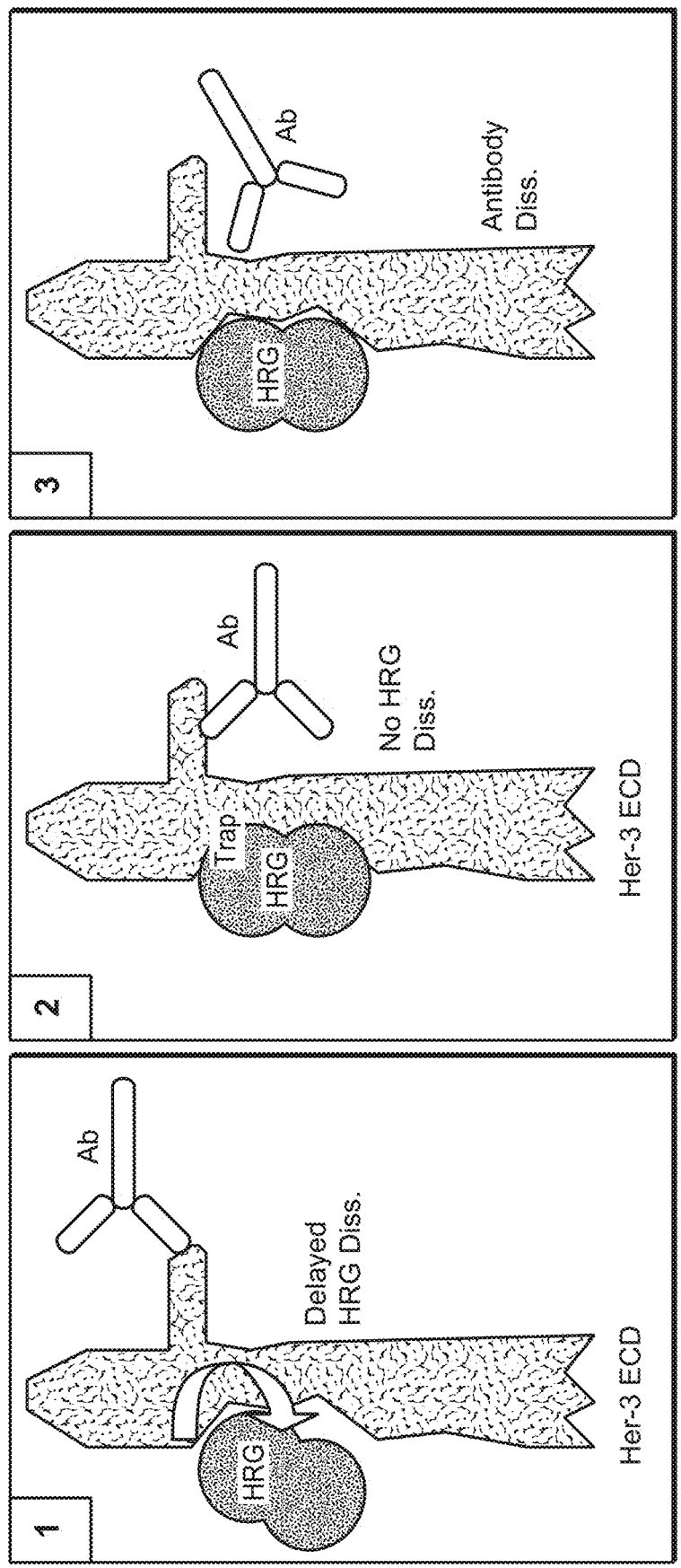
FIG. 10 Schematic Mode of Actions identified by Biacore™ functional assays. 1: M-08-11 binds to the Heregulin activated Her-3 ECD and induces a delayed Heregulin dissociation, whereby M-08-11 stays in the Her-3 ECD receptor complex. 2: M-05-74 binds to the Heregulin activated Her-3 ECD. Heregulin is trapped in the complex and the antibody stays in the complex 3: 8B8 binds the Heregulin activated Her-3 ECD. The whole complex dissociates from the antibody.

In FIG. 10 a scheme of these binding modes of action is shown: 1: M-08-11 binds to the Heregulin activated Her-3 ECD and induces a delayed Heregulin dissociation, whereby M-08-11 stays in the Her-3 ECD receptor complex. 2: M-05-74 binds to the Heregulin activated Her-3 ECD. Heregulin is trapped in the complex and the antibody stays in the complex. 3: 8B8 binds the Heregulin activated Her-3 ECD. The whole complex dissociates from the antibody.

Peptide-Based 2D Epitope Mapping

Figure 11:
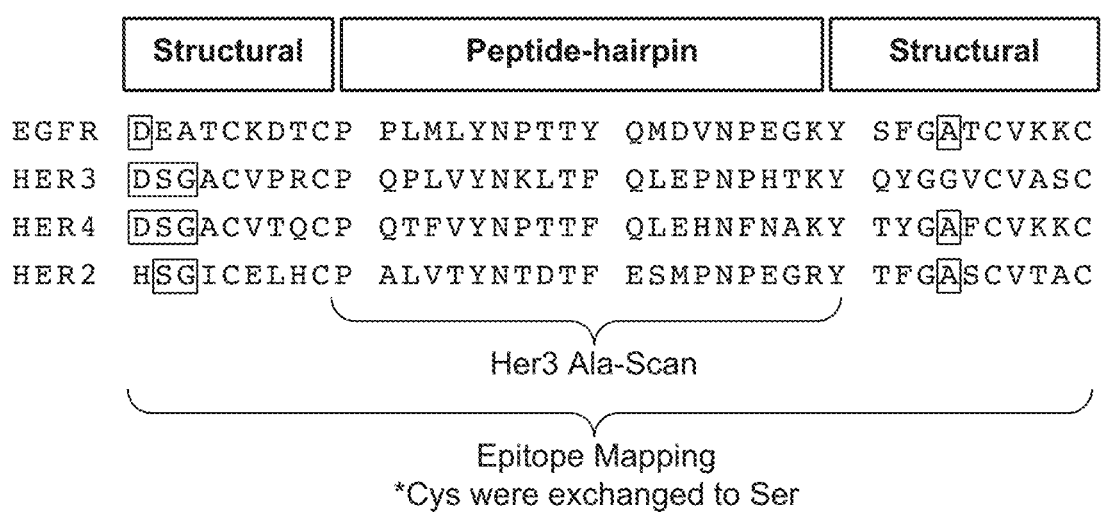
FIG. 11 Strategy of the epitope mapping and alanine-scan approach. The peptide hairpin sequences (peptide hairpin) of EGFR (amino acids 232-271 of SEQ ID NO: 7), Her-2 ECD (amino acids 239-277 of SEQ ID NO: 9), Her-3 ECD (amino acids 232-271 of SEQ ID NO: 4), and Her-4 ECD (amino acids 229-268 of SEQ ID NO: 6), including their structural embeddings (structural) were investigated. Cysteins were replaced by serines.

In another embodiment a peptide-based epitope mapping experiment was done to characterize the Her-3 ECD epitopes by using the CelluSpots™ Synthesis and Epitope Mapping technology. Epitope mappings were carried out by means of a library of overlapping, immobilized peptide fragments (length: 15 amino acids) corresponding to the sequences of human Her-1 ECD, Her-2 ECD, Her-3 ECD and Her-4 ECD peptide hairpins. In FIG. 11, the strategy of the epitope mapping and alanine-scan approach is shown. The peptide hairpin sequences (ß-hairpin) of HER1(EGFR) ECD, HER2 ECD, HER3 ECD and HER4 ECD including their structural embeddings (structural) were investigated. Cysteins were replaced by serines. For antibody selection of the antibodies via binding to such ß-hairpins, the ß-hairpins of HER3 and HER4 are defined by SEQ ID NO:1 and SEQ ID NO:2.

Each peptide synthesized was shifted by one amino acid, i.e. it had 14 amino acids overlap with the previous and the following peptide, respectively. For preparation of the peptide arrays the Intavis CelluSpots™ technology was employed. In this approach, peptides are synthesized with an automated synthesizer (Intavis MultiPep RS) on modified cellulose disks which are dissolved after synthesis. The solutions of individual peptides covalently linked to macromolecular cellulose are then spotted onto coated microscope slides. The CelluSpots™ synthesis was carried out stepwise utilizing 9-fluorenylmethoxycarbonyl (Fmoc) chemistry on amino-modified cellulose disks in a. 384-well synthesis plate. In each coupling cycle, the corresponding amino acids were activated with a solution of DIGHOBt in DMF. Between coupling steps un-reacted amino groups were capped with a mixture of acetic anhydride, diisopropylethyl amine and 1-hydroxybenzotriazole. Upon completion of the synthesis, the cellulose disks were transferred to a 96-well plate and treated with a mixture of trifluoroacetic acid (TEA), dichloromethane, triisoproylsilane (TIS) and water for side chain deprotection. After removal of the cleavage solution, the cellulose bound peptides are dissolved with a mixture of TFA, TFMSA, TIS and water, precipitated with diisopropyl ether and re-suspended in DMSO. The peptide solutions were subsequently spotted onto Intavis CelluSpots™ slides using an Intavis slide spotting robot.

For epitope analysis, the slides prepared as described above were washed with ethanol and then with Tris-buffered saline (TBS; 50 mM Tris, 137 mM NaCl, 2.7 mM KCl, pH 8) before blocking for 16 h at 4° C. with 5 mL 10× Western Blocking Reagent (Roche Applied Science), 2.5 g sucrose in TBS, 0.1% Tween 20. The slide was washed with TBS and 0.1% Tween 20 and incubated afterward with 1 μg/mL of the corresponding IGF1 antibodies in TBS and 0.1% Tween 20 at ambient temperature for 2 h and subsequently washed with TBS+0.1% Tween 20. For detection, the slide was incubated with anti-rabbit/anti-mouse secondary HRP-antibody (1:20000 in TBS-T) followed by incubation with chemiluminescence substrate luminol and visualized with a Lumilmager (Roche Applied Science). ELISA-positive SPOTs were quantified and through assignment of the corresponding peptide sequences the antibody binding epitopes were identified.

Figure 12:
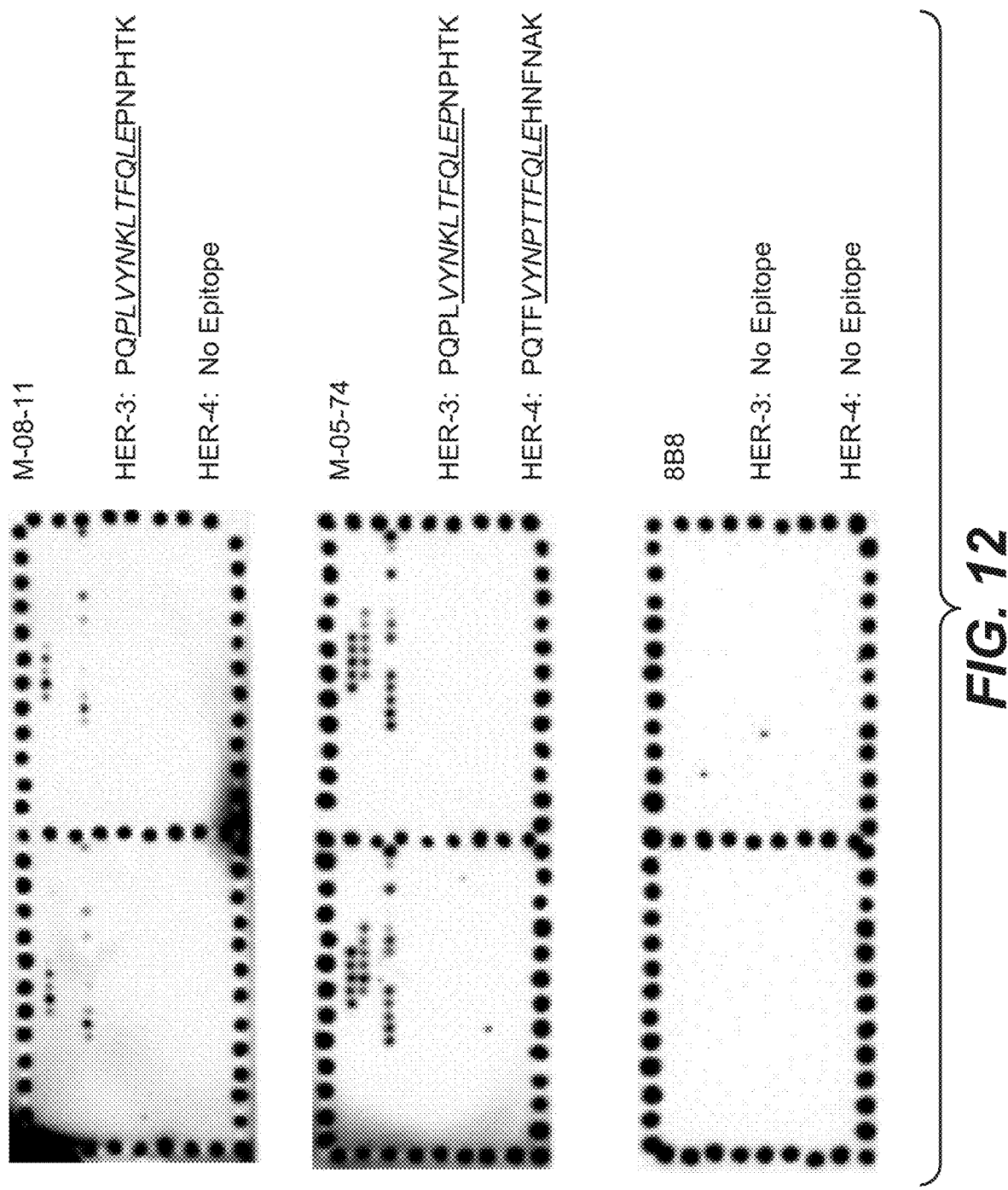
FIG. 12 CelluSpots™ Synthesis and Epitope Mapping of epitopes of antibody M-05-74 on HER3 and HER4. Anti-HER3/HER4 antibody M-05-74 binds to HER3 ECD binding epitope VYNKLTFQLEP (SEQ ID NO:43) and to HER4 ECD binding epitope VYNPTTFQLE (SEQ ID NO:44).
Figure 16:
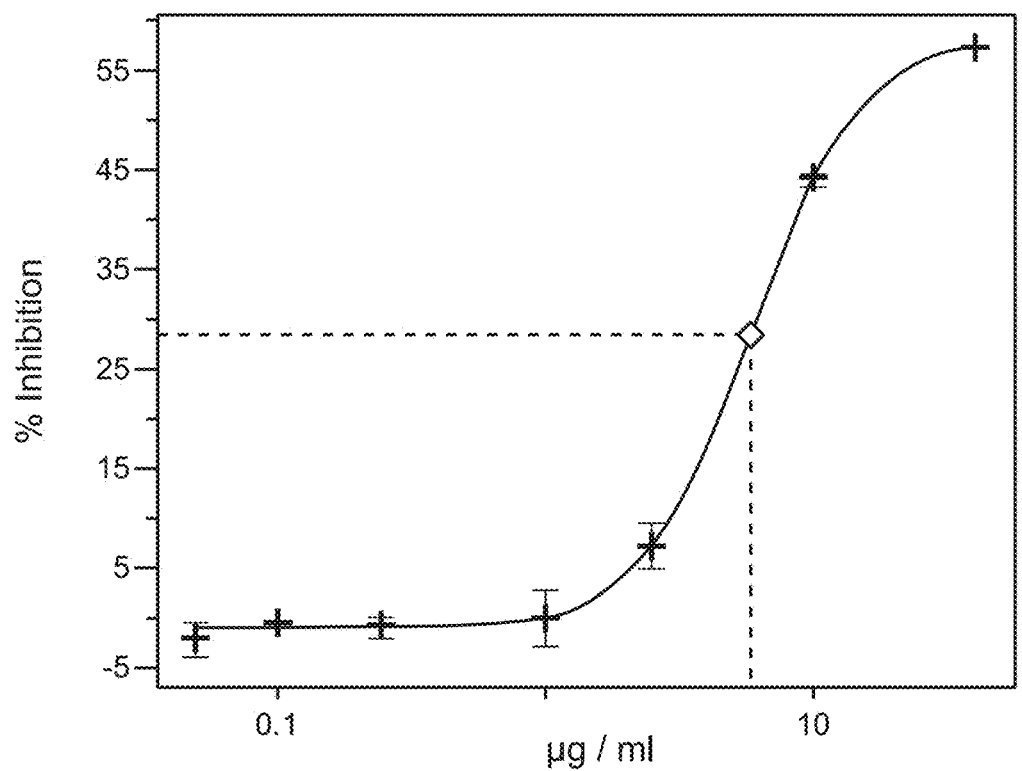
FIG. 16 Treatment of MDA-MB175 cells with M-05-74 resulted in inhibition of cell proliferation.

As depicted in FIG. 12, M-05-74 shows a HER3 ECD epitope with the amino acid sequence VYNKLTFQLEP (SEQ ID NO:43) and a crossreactivity to a HER4 ECD epitope with the amino acid sequence VYNPTTFQLE (SEQ ID NO:44) with no detectable signals versus the hairpin motives in EGFR and the HER2 ECD. No signals at all were detectable with the 8B8 antibody, therefore the 8B8 antibody targets epitopes, different from the hairpin peptide motives. M-08-11 shows a HER3 ECD specific epitope with the amino acid sequence PLVYNKLTFQLE (corresponding to amino acid residues 3-14 of SEQ ID NO:1) with no cross-reactivity detectable to the other hairpin sequences of the Her-family.

In FIG. 13, the amino acids identified by Ala-Scan which are contributing most to the binding of antiHER3/HER4 antibody M-05-74 to its HER3 ECD binding epitope VYNKLTFQLEP (SEQ ID NO:43) and to its HER4 ECD binding epitope VYNPTTFQLE (SEQ ID NO:44) are underlined/bold.

Example 5

Binding of HRG to HER3-ECD in the Presence of HER3 Antibody (ELISA)

A Streptavidin-coated 96-well plate was incubated at 4° C. with cell culture supernatant containing SBP-tagged HER3-ECD. On the next day the wells were washed three times with washing buffer (PBS+0.05% Tween-20) and blocked with PBS containing 1% BSA for one hour. After another three washes with washing buffer, 40 µl antibody solution (in Delfia Binding Buffer) was added to each well as a 2× stock of the desired final concentrations ($10^{-3}$ to $10^3$ nM, alternatively $10^{-4}$ to $10^2$ nM). Immediately 40 µl of 20 nM Europium-labeled Heregulin-beta (PeproTech, Cat. #100-03) was added to achieve a final concentration of 10 nM. The plates were incubated on a shaker at room temperature for two hours. Following three washes with Delfia® Wash Buffer, Delfia® Enhancement Solution was added and incubated on a shaker for 15 minutes (light protected). Finally, the plates were measured in a Tecan Infinite F200 reader using a time-resolved fluorescence measurement protocol. The binding of M-05-74 (named M-074 in FIG. 14) can promote binding of HRG to HER3-ECD until a plateau is reached at a signal of 650. Results are shown in FIG. 14.

Example 6 a) Inhibition of HER3 Phosphorylation in ZR-75-1 Cells

Assays were performed in ZR-75-1 cells according to the following protocol: Seed cells with 500,000 cells/well into Poly-D-Lysine coated 6-well plate in RPMI1640 medium with 10% FCS. Incubate for 24 h. Remove medium by aspirating, incubate overnight with 500 µl/well RPMI 1640 with 0.5% FCS. Add antibodies in 500 µl RPMI 1640 with 0.5% FCS. Incubate for 1 h. Add Heregulin-beta (PeproTech, Cat. #100-03)) (final concentration 500 ng/ml) for 10 min. To lyse the cells remove medium and add 80 µl ice cold Triton-X-100 cell lysis buffer and incubate for 5 minutes on ice. After transferring the lysate into 1.5 ml reaction tube and centrifugation at 14000 rpm for 15 min at 4° C., transfer supernatant into fresh reaction tubes. Samples containing equal amounts of protein in SDS loading buffer were separated on SDS PAGE and blotted by using a semi-dry Western Blot to nitrocellulose membranes. Membranes were blocked by 1×NET-buffer+0.25% gelatine for 1 h hour and pHER3 is detected by the antibody αPhospho-HER3/ErbB3 (Tyr1289) (21D3), Cell Signaling, #4791 and HER3 by the antibody αErbB3 (C-17), Santa Cruz, # sc-285 respectively. After washing and detection of the signals by an POD coupled secondary antibody, bands were densometricaly scanned. Percent (%) inhibition of anti-HER3 antibodies M-05-74 on receptor phosphorylation in zr-75-1 cells is shown below in Table 7.

TABLE 7

| % Inhibition of HER3 phosphorylation in ZR-75-1 cells | |
|---|---|
| antibody | pHER3 % inhibition [10 µg/ml] |
| Ctrl | 0 |
| M-05-74 | 49 | b) Inhibition of HER3 Phosphorylation of the Bivalent Parent M-05-74 and the Fab Fragment of M-05-74 (Fab-74)

MCF-7 cells were seeded into 24-Well-plates (1 ml RPMI, 10% FCS, 3×105 cells per well) and were incubated at 37° C./5% CO2 overnight. After 24 hours the media was replaced with 1 ml media containing 0.5% FCS. After 48 hours the antibodies were added to a final concentration of 10 µg/ml, 1 µg/ml and 0.1 µg/ml (M-05-74) and 6.66 µg/ml, 0.66 µg/ml and 0.066 µg/ml (Fab-074). The plates were incubated at 37° C. for 50 minutes and then Heregulin-beta (PeproTech, Cat. #100-03) was added to a final concentration of 500 ng/ml. The plates were incubated for a further 10 minutes at 37° C./5% CO2. The cells were washed with PBS and lysed in 40 µl Triton Lysis Buffer (1% Triton) containing Aprotinin (10 µg/ml), Orthovanadate (0.4 mM), Phenylmethylsulfonyl fluoride (1 mM). 26 µl of the collected lysates were transferred to reaction tubes and 14 µl Sample Buffer (NuPAGE LDS Sample Buffer 4×, NuPAGE Sample Reducing Agent 10×) was added. The samples were incubated for 10 minutes at 70° C. and then analysed by SDS-PAGE (NuPAGE, 4-12% Bis-Tris-Mini-Gel). Electroblotting was performed using the iBlot Dry Blotting System (Invitrogen). The nitrocellulose membrane was incubated with phospho-HER3 antibody (a Phospho Her3, Cellsignaling #4791, Rabbit 1:1000) followed by incubation with HRP-conjugated secondary antibody (goat anti rabbit 1:5000, BioRad cat: 170-6515). Signal was developed using ECL Detection Reagents (Amersham RPN2209) on X-Ray film (Roche Lumi-Film Chemiluminescent Detection Film 11666657001). The anti-HER3 antibody M-05-74 (full length purified from hybridoma) and the Fab fragment of the antibody Fab-74 (obtained py papain cleavage from full length M-05-74) were investigated in eqimolar amounts. Fab fragments were generated by papain digestion of the antibody. Briefly, 1 ml of app. 2 mg/ml antibody containing solution was supplemented with 25 mM Cystein and 70 µg papain (Roche). After incubation at 37° C. for 1.5 h, the digestion reaction was stopped by addition of iodoacetamide and the reaction mixture was purified by MabSelect SuRe™ (GE Healthcare). The Fab containing flowthrough fraction was further purified by size exclusion chromatography (Superdex™ 200; GE Healthcare).

Percent (%) inhibition of anti-HER3 antibodies on receptor phosphorylation in MCF7 cells is summarised below and in Table 8. The antibody M-05-74 (full length from hybridoma) and the Fab fragment of this antibody Fab-74 can inhibit HER3 phosphorylation in equimolar concentrations to an comparable extent.

TABLE 8

% Inhibition of HER3 phosphorylation in MCF-7 cells

| Antibody | pHER3 % inhibition [6.66 nM] | pHER3 % inhibition [0.66 nM] |
|---|---|---|
| control | 0 | 0 |
| M-05-74 (full length from hybridoma) | 94 | 13 |
| Fab fragment of M-05-74 (Fab-74) | 96 | 14 |

Example 7

Inhibition of HER2/HER3 Heterodimers (Imunoprecipitation and Western Blot) in MCF7 Cells MCF-7 cells were seeded into 6-Well-plates (2 ml RPMI, 10% FCS, 8×105 cells per well) and were grown overnight. On the next day the media was exchanged by 2 ml starving media containing 0.5% FCS. On day three the antibodies were added to a final concentration of 10 µg/ml and the plates were incubated at 37° C. After 50 minutes Heregulin-beta (PeproTech, Cat. #100-03) was added to a final concentration of 500 ng/ml and the plates were incubated for another 10 minutes at 37° C. The cells were washed with PBS and lysed in 250 µl Triton Lysis Buffer containing 1% Digitonin. 60 µl of the collected lysates were transferred to reaction tubes and incubated with 40 µl antibody-coupled Sepharose® (either Herceptin® or HER3-antibody #208) and 500 µl Buffer containing 0.3% Digitonin. The reaction mixes were incubated on a wheel rotator overnight at 4° C. On the next day the reaction mixes were washed three times with 500 µl Buffer containing 0.3% Digitonin. After the last wash the supernatant was discarded and 10 µl 4× Loading Buffer was added. The tubes were incubated for 10 minutes at 70° C. and the supernatants were consequently loaded onto a gel for SDS-PAGE. After the following Semi-Dry Western Blot the membranes containing the samples immunoprecipitated with HER2 antibody were incubated with anti-HER3/HER4 antibody M-05-74 (M-074 in FIG. 15), and vice versa. The membranes were then incubated with HRP-conjugated secondary antibody and the ECL signal was transferred onto X-Ray film. Results are shown in FIG. 15, showing a strong inhibition of the HER2/HER heterodimer formation (HER2/HER heterodimerization) by the M-05-74.

Example 8

Inhibition of Tumor Cell Proliferation of M-05-74 in MDA-MB-175 Cells.

The anti-tumor efficacy of HER3 antibodies M-05-74 in a cell proliferation assay, using MDA-MB-175 cells (VII Human Breast Carcinoma Cells, ATCC catalog no. HTB-25), was assessed. 20,000 cells per well were seeded into sterile 96 well tissue culture plates with DMEM/F12 cell culture medium, containing 10% FCS and incubated at 37° C.±1° C. with 5%±1% $CO_2$ for one day. The cells are slow growing cells with a doubling time of ca. 3 days. Anti-HER3 antibodies were added in dilution series and further incubated for 6 days. Cell viability was then assessed using the alamarBlue® readout. EC50 values were calculated.

TABLE 9

EC50 of the Inhibition of tumor cell proliferation of M-05-74 in MDA-MB-175 cells

| antibody | $EC_{50}$ [µg/ml] |
|---|---|
| M-05-74 | 5.8 |

Example 9

In Vivo Antitumor Efficacy of Anti-HER3 Antibody M-05-74

The in vivo antitumor efficacy of the anti-HER3 antibody M-05-74 (M-074) could be detected in cell based models of various tumor origin (e.g. SCCHN and pancreatic cancer) transplanted on SCID beige. As example data are shown for the SCCHN xenograft model FaDu (cell line based).

Test Agents

M-05-74 was provided as stock solution from Roche, Penzberg, Germany expressed and purified from hybridoma cells. Antibody buffer included histidine. Antibody solution was diluted appropriately in buffer from stock prior injections.

Cell Lines and Culture Conditions

FaDu human HNSCC cells were originally obtained from ATCC. The tumor cell line was routinely cultured in MEM Eagle medium supplemented with 10% fetal bovine serum, 2 mM L-glutamine, 1 mM sodium pyruvate and 0.1 mM NEAA at 37° C. in a water-saturated atmosphere at 5% CO2. Culture passage was performed with trypsin/EDTA 1× splitting every third day.

Animals

Female SCID beige or nude mice were purchased from breeder (e.g. Charles River, Sulzfeld, Germany) and maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum.

Animals were controlled daily for clinical symptoms and detection of adverse effects. For monitoring throughout the experiment body weight of animals was documented.

Animal treatment started after animal randomisation after cell transplantation when median tumor size was about 100-150 mm3. Antibody was administered as single agent at 10 mg/kg i.p. q7d once weekly for several weeks depending of the model. The corresponding vehicle was administered on the same days.

FaDu HNSCC xenograft bearing mice were treated with antibody M-05-74 from study day 10 to 24. As a result, treatment with H-74 antibody showed significant anti-tumor efficacy with nearly tumors stasis of s.c. FaDu xenografts. The Tumor Growth Inhibition (TGI) was calculated at 89%.

Figure 17:
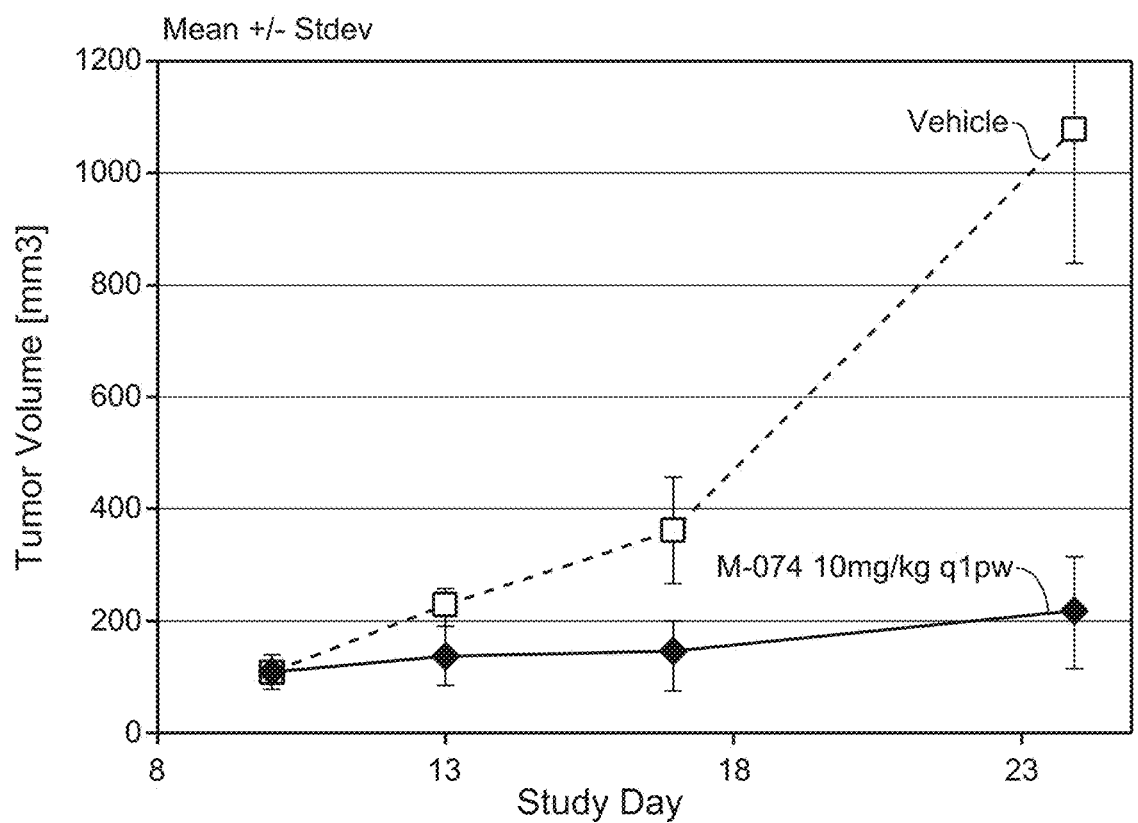
FIG. 17 Treatment with M-05-74 (M-074) (10 mg/kg q7d, i.p.) resulted in tumor stasis a FaDu HNSCC transplanted xenografts.
Figure 18:
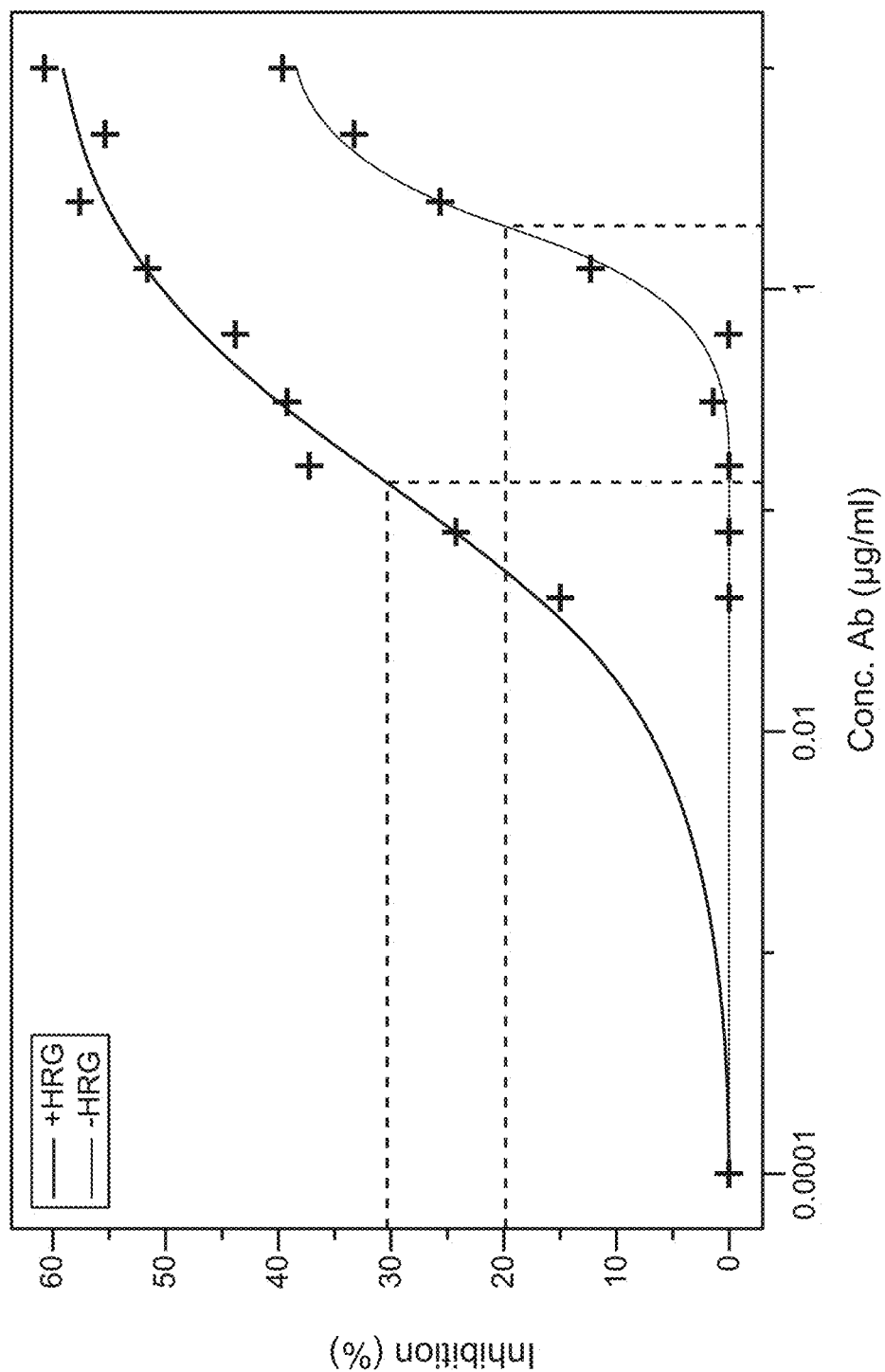
FIG. 18 Treatment with M-05-74-Fab-*Pseudomonas* exotoxin conjugate (M-074-PE) (10 mg/kg q7d, i.p.) resulted in stronger inhibition of cell proliferation in the presence (bold line) of HRG than in the absence (thin line) of HRG.

Treatment with M-05-74 (10 mg/kg q7d×3, i.p.) resulted in nearly tumor stasis of FaDu. Results are shown in FIG. 17, wherein M-05-74 is named M-074.

Example 10

Generation of M-05-74-Fab-*Pseudomonas* Exotoxin Conjugate (M-05-74-PE)

Expression, purification and renaturation of Fab fragment of M-05-74, PE24 variant, and Fab fragment of M-05-74 conjugated to *Pseudomonas* exotoxin variant PE24LR8M based on the Sequences of SEQ ID NO:45, 46, 47, 48 (or 49).

Expression of Fab (e.g. for Sortase Coupling)—Expression Vectors

For the expression of the described Fab fragments, variants of expression plasmids for transient expression (e.g. HEK293-F) cells based either on a cDNA organization with or without a CMV-Intron A promoter or on a genomic organization with a CMV promoter were applied.

Beside the antibody expression cassette the vectors contained:
- an origin of replication which allows replication of this plasmid in *E. coli*, and
- a ß-lactamase gene which confers ampicillin resistance in *E. coli*.

The transcription unit of the antibody gene was composed of the following elements:
- unique restriction site(s) at the 5' end
- the immediate early enhancer and promoter from the human cytomegalovirus,
- followed by the Intron A sequence in the case of the cDNA organization,
- a 5'-untranslated region of a human antibody gene,
- an immunoglobulin heavy chain signal sequence,
- the human antibody chain either as cDNA or as genomic organization with the immunoglobulin exon-intron organization
- a 3' untranslated region with a polyadenylation signal sequence, and
- unique restriction site(s) at the 3' end.

The fusion genes comprising the antibody chains as described below were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The Fab fragments were expressed by transient co-transfection of the expression plasmids of the heavy and the light chain in HEK29-F cells growing in suspension as described below.

Transient Transfections in HEK293-F System

The Fab fragments were generated by transient transfection with the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the four expression plasmids and 293-Free™ (Novagen) or Fectin (Invitrogen). For 2 L shake flask (Corning) HEK293-F cells were seeded at a density of 1.0E*6 cells/mL in 600 mL and incubated at 120 rpm, 8% CO2. The day after the cells were transfected at a cell density of ca. 1.5E*6 cells/mL with ca. 42 mL mix of A) 20 mL Opti-MEM™ (Invitrogen) with 600 µg total plasmid DNA (1 µg/mL) encoding the heavy or modified heavy chain, respectively and the corresponding light chain in an equimolar ratio and B) 20 ml Opti-MEM™+1.2 mL 293-Free™ (Novagen) or Fectin (2 µl/mL). According to the glucose consumption glucose solution was added during the course of the fermentation. The supernatant containing the secreted antibody was harvested after 5-10 days and antibodies were either directly purified from the supernatant or the supernatant was frozen and stored.

Expression of *Pseudomonas* Exotoxin Variant PE24-LR8M for Sortase Coupling—Expression Vector For the expression of PE24-LR8M an *E. coli* expression plasmid was used.

Beside the expression cassette for the *pseudomonas* exotoxin A domain III the vector contained:
- an origin of replication from the vector pBR322 for replication in *E. coli* (according to Sutcliffe, G., et al., Quant. Biol. 43 (1979) 77-90),
- the lacI repressor gene from *E. coli* (Farabaugh, P. J., Nature 274 (1978) 765-769),
- the URA3 gene of *Saccharomyces cerevisiae* coding for orotidine 5'-phosphate decarboxylase (Rose, M. et al. Gene 29 (1984) 113-124) which allows plasmid selection by complementation of *E. coli* pyrF deletion strains (uracil auxotrophy).

The transcription unit of the toxin gene was composed of the following elements:
- unique restriction site(s) at the 5' end,
- the T5 hybrid promoter (T5-PN25/03/04 hybrid promoter according to Bujard, H., et al. Methods. Enzymol. 155 (1987) 416-433 and Stueber, D., et al., Immunol. Methods IV (1990) 121-152) including a synthetic ribosomal binding site according to Stueber, D., et al. (see before),
- the *pseudomonas* exotoxin A domainIII with an N-terminal coupling tag followed by a furin site (SEQ ID NO:45 *Pseudomonas* exotoxin variant PE24LR8M_3G, including a GGG linker for sortase coupling),
- two bacteriophage-derived transcription terminators, the λ-T0 terminator (Schwarz, E., et al., Nature 272 (1978) 410-414) and the fd-terminator (Beck E. and Zink, B. Gene 1-3 (1981) 35-58),
- unique restriction site(s) at the 3' end.

Cultivation and Expression of the *Pseudomonas* Exotoxin A Construct Variant PE24-LR8M_3G in an *E. coli* Fed-Batch Process on Chemical Defined Medium For the expression of PE24-LR8M_3G_Ecoli (25 kDa) the *E. coli* host/vector system which enables an antibiotic-free plasmid selection by complementation of an *E. coli* auxotrophy (PyrF) was employed (EP 0 972 838 and U.S. Pat. No. 6,291,245).

An *E. coli* K12 strain was transformed by electroporation with the expression plasmid. The transformed *E. coli* cells were first grown at 37° C. on agar plates. A colony picked from this plate was transferred to a 3 mL roller culture and grown at 37° C. to an optical density of 1-2 (measured at 578 nm). Then 1000 µl culture where mixed with 1000 µl sterile 86%-glycerol and immediately frozen at −80° C. for long time storage. The correct product expression of this clone was first verified in small scale shake flask experiments and analyzed with SDS-Page prior to the transfer to the 10 L fermenter.

Pre Cultivation:

For pre-fermentation a chemical defined medium has been used. For pre-fermentation 220 ml of medium in a 1000 ml Erlenmeyer-flask with four baffles was inoculated with 1.0 ml out of a primary seed bank ampoule. The cultivation was performed on a rotary shaker for 8 hours at 32° C. and 170 rpm until an optical density (578 nm) of 2.9 was obtained. 100 ml of the pre cultivation was used to inoculate the batch medium of the 10 L bioreactor.

Fermentation:

For fermentation in a 10 l Biostat C, DCU3 fermenter (Sartorius, Melsungen, Germany) a chemical defined batch medium was used. All components were dissolved in deionized water. The alkaline solution for pH regulation was an aqueous 12.5% (w/v) $NH_3$ solution supplemented with 11.25 g/l L-methionine.

Starting with 4.2 l sterile batch medium plus 100 ml inoculum from the pre cultivation the batch fermentation was performed at 31° C., pH 6.9±0.2, 800 mbar back pressure and an initial aeration rate of 10 l/min. The relative value of dissolved oxygen (pO2) was kept at 50% throughout the fermentation by increasing the stirrer speed up to 1500 rpm. After the initially supplemented glucose was depleted, indicated by a steep increase in dissolved oxygen values, the temperature was shifted to 25° C. and 15 minutes later the fermentation entered the fed-batch mode with the start of both feeds (60 and 14 g/h respectively). The rate of feed 2 is kept constant, while the rate of feed 1 is increased stepwise with a predefined feeding profile from 60 to finally 160 g/h within 7 hours. When carbon dioxide off gas concentration leveled above 2% the aeration rate was constantly increased from 10 to 20 l/min within 5 hours. The expression of recombinant PE24-LR8M_3G_Ecoli protein was induced by the addition of 2.4 g IPTG at an optical density of approx. 120. The target protein is expressed soluble within the cytoplasm.

After 24 hours of cultivation an optical density of 209 is achieved and the whole broth is cooled down to 4-8° C. The bacteria are harvested via centrifugation with a flow-through centrifuge (13,000 rpm, 13 l/h) and the obtained biomass is stored at −20° C. until further processing (cell disruption). The yield is 67.5 g dry cells per liter.

Analysis of Product Formation:

Samples drawn from the fermenter, one prior to induction and the others at dedicated time points after induction of protein expression are analyzed with SDS-Polyacrylamide gel electrophoresis. From every sample the same amount of cells ($OD_{Target}$=10) are suspended in 5 mL PBS buffer and disrupted via sonication on ice. Then 100 µL of each suspension are centrifuged (15,000 rpm, 5 minutes) and each supernatant is withdrawn and transferred to a separate vial. This is to discriminate between soluble and insoluble expressed target protein. To each supernatant (=soluble protein fraction) 100 µL and to each pellet (=insoluble protein fraction) 200 µL of SDS sample buffer (Laemmli, U. K., Nature 227 (1970) 680-685) are added. Samples are heated for 15 minutes at 95° C. under intense mixing to solubilize and reduce all proteins in the samples. After cooling to room temperature 5 µL of each sample are transferred to a 4-20% TGX Criterion Stain Free polyacrylamide gel (Bio-Rad). Additionally 5 µl molecular weight standard (Precision Plus Protein Standard, Bio-Rad) were applied.

The electrophoresis was run for 60 Minutes at 200 V and thereafter the gel was transferred the GelDOC™ EZ Imager (Bio-Rad) and processed for 5 minutes with UV radiation. Gel images were analyzed using Image Lab analysis software (Bio-Rad). Relative quantification of protein expression was done by comparing the volume of the product bands to the volume of the 25 kDa band of the molecular weight standard.

Cultivation and Expression of an Antibody Fragment Light Chain Construct (VL) and an Antibody Fragment Heavy Chain Pseudomonas Exotoxin A Variant Fusion (Fab-PE24) in an E. coli Fed-Batch Process on Chemical Defined Medium For the expression of a Fab-light chain (23.4 kDa) and a Fab-heavy chain PE24 fusion (48.7 kDa) the E. coli host/vector system which enables an antibiotic-free plasmid selection by complementation of an E. coli auxotrophy (PyrF) was employed (EP 0 972 838 and U.S. Pat. No. 6,291,245).

An E. coli K12 strain was transformed by electroporation with the respective expression plasmids. The transformed E. coli cells were first grown at 37° C. on agar plates. For each transformation a colony picked from this plate was transferred to a 3 mL roller culture and grown at 37° C. to an optical density of 1-2 (measured at 578 nm). Then 1000 µl culture where mixed with 1000 µl sterile 86%-glycerol and immediately frozen at −80° C. for long time storage. The correct product expression of these clones was first verified in small scale shake flask experiments and analyzed with SDS-Page prior to the transfer to the 10 L fermenter.

Pre-Cultivation:

For pre-fermentation a chemical defined medium has been used. For pre-fermentation 220 ml of medium in a 1000 ml Erlenmeyer-flask with four baffles was inoculated with 1.0 ml out of a primary seed bank ampoule. The cultivation was performed on a rotary shaker for 9 hours at 37° C. and 170 rpm until an optical density (578 nm) of 7 to 8 was obtained. 100 ml of the pre cultivation was used to inoculate the batch medium of the 10 L bioreactor.

Fermentation (RC52#003):

For fermentation in a 10 l Biostat C, DCU3 fermenter (Sartorius, Melsungen, Germany) a chemical defined batch medium was used. The alkaline solution for pH regulation was an aqueous 12.5% (w/v) $NH_3$ solution supplemented with 11.25 g/l L-methionine.

Starting with 4.2 l sterile batch medium plus 100 ml inoculum from the pre cultivation the batch fermentation was performed at 31° C., pH 6.9±0.2, 800 mbar back pressure and an initial aeration rate of 10 l/min. The relative value of dissolved oxygen (pO2) was kept at 50% throughout the fermentation by increasing the stirrer speed up to 1500 rpm. After the initially supplemented glucose was depleted, indicated by a steep increase in dissolved oxygen values, the temperature was shifted to 37° C. and 15 minutes later the fermentation entered the fed-batch mode with the start of both feeds (60 and 14 g/h respectively). The rate of feed 2 is kept constant, while the rate of feed 1 is increased stepwise with a predefined feeding profile from 60 to finally 160 g/h within 7 hours. When carbon dioxide off gas concentration leveled above 2% the aeration rate was constantly increased from 10 to 20 l/min within 5 hours. The expression of recombinant target proteins as insoluble inclusion bodies located in the cytoplasm was induced by the addition of 2.4 g IPTG at an optical density of approx. 40.

After 24 hours of cultivation an optical density of 185 is achieved and the whole broth is cooled down to 4-8° C. The bacteria are harvested via centrifugation with a flow-through centrifuge (13,000 rpm, 13 l/h) and the obtained biomass is stored at −20° C. until further processing (cell disruption). The yield is between 40 and 60 g dry cells per liter.

Analysis of Product Formation:

Samples drawn from the fermenter, one prior to induction and the others at dedicated time points after induction of protein expression are analyzed with SDS-Polyacrylamide gel electrophoresis. From every sample the same amount of cells ($OD_{Target}$=10) are suspended in 5 mL PBS buffer and disrupted via sonication on ice. Then 100 µL of each suspension are centrifuged (15,000 rpm, 5 minutes) and each supernatant is withdrawn and transferred to a separate vial. This is to discriminate between soluble and insoluble expressed target protein. To each supernatant (=soluble protein fraction) 100 µL and to each pellet (=insoluble protein fraction) 200 µL of SDS sample buffer (Laemmli, U.

K., Nature 227 (1970) 680-685) are added. Samples are heated for 15 minutes at 95° C. under intense mixing to solubilize and reduce all proteins in the samples. After cooling to room temperature 5 µL of each sample are transferred to a 4-20% TGX Criterion Stain Free polyacrylamide gel (Bio-Rad). Additionally 5 µl molecular weight standard (Precision Plus Protein Standard, Bio-Rad) and 3 amounts (0.3 µl, 0.6 µl and 0.9 µl) quantification standard with known target protein concentration (0.1 µg/µl) were applied.

The electrophoresis was run for 60 Minutes at 200 V and thereafter the gel was transferred the GelDOC™ EZ Imager (Bio-Rad) and processed for 5 minutes with UV radiation. Gel images were analyzed using Image Lab analysis software (Bio-Rad). With the three standards a linear regression curve was calculated with a coefficient of >0.99 and thereof the concentrations of target protein in the original sample was calculated.

Purification, Sortase Coupling and Renaturation (of Fab Fragment of M-05-74, PE24 Variant, and Fab Fragment of M-05-74 Conjugated to *Pseudomonas* Exotoxin Variant PE24LR8M)

Fab Fragment

The Fab fragment was purified by affinity chromatography (Ni Sepharose® High Perfomance HisTrap™) according to the manufacture's description. In brief, the supernatant was loaded onto the column equilibrated in 50 mM sodium phosphate pH 8.0, 300 mM NaCl. Protein elution was performed with the same buffer at pH 7.0 with a washing step containing 4 mM imidazole followed by a gradient up to 100 mM imidazole. Fractions containing the desired Fab fragment were pooled and dialyzed against 20 mM His, 140 mM NaCl, pH 6.0.

PE24 for Sortase Coupling

*E. coli* cells expressing PE24 were lysed by high pressure homogenization (if details are required: Christian Schantz) in 20 mM Tris, 2 mM EDTA, pH 8.0+Complete protease inhibitor cocktail tablets (Roche). The lysate was filtrated and loaded onto a Q Sepharose® FF (GE Healthcare) equilibrated in 20 mM Tris, pH 7.4. Protein was eluted with a gradient up to 500 mM NaCl in the same buffer. PE24 containing fractions were identified by SDS PAGE. The combined pool was concentrated and applied to a HiLoad™ Superdex™ 75 (GE Healthcare) equilibrated in 20 mM Tris, 150 mM NaCl, pH 7.4. Fractions containing PE24 were pooled according to SDS PAGE and frozen at −80° C.

Sortase Coupling of Fab Fragment to PE24

Fab fragment and PE24 were diafiltrated separately into 50 mM Tris, 150 mM NaCl, 5 mM $CaCl_2$) pH7.5 using Amicon® Ultra 4 centrifugal filter devices (Merck Millipore) and concentrated to 5-10 mg/ml. Both proteins and sortase were combined in a 1:1:0.8 molar ratio. After one hour incubation at 37° C. the mixture was loaded onto a Ni Sepharose® High Perfomance HisTrap™ equilibrated in 50 mM sodium phosphate, pH 8.0, 300 mM NaCl. Elution was performed with a gradient up to 100 mM imidazole in the same buffer pH 7.0. The flow through fractions containing the final product Fab-PE24 was concentrated and loaded onto a HiLoad™ Superdex™ 200 (GE Healthcare) in 20 mM Tris, 150 mM NaCl, pH 7.4. Fractions containing the desired coupled protein were pooled and stored at −80° C. As sortase soluble *S. aureus* sortase A was used (SEQ ID NO: 50). Soluble *S. aureus* sortase A was expressed and purified using the following expression plasmid. The sortase gene encodes an N-terminally truncated *Staphylococcus aureus* sortase A (60-206) molecule. The expression plasmid for the transient expression of soluble sortase in HEK293 cells comprised besides the soluble sortase expression cassette an origin of replication from the vector pUC18, which allows replication of this plasmid in *E. coli*, and a beta-lactamase gene which confers ampicillin resistance in *E. coli*. The transcription unit of the soluble sortase comprises the following functional elements:

the immediate early enhancer and promoter from the human cytomegalovirus (P-CMV) including intron A, a human heavy chain immunoglobulin 5'-untranslated region (5'UTR), a murine immunoglobulin heavy chain signal sequence, an N-terminally truncated *S. aureus* sortase A encoding nucleic acid, and the bovine growth hormone polyadenylation sequence (BGH pA).

Renaturation of Fab-PE24 Derived from *E. coli* Inclusion Bodies

Inclusion bodies of VH-PE24 and VL-$C_{kappa}$ were solubilized separately in 8 M guanidinium hydrochloride, 100 mM Tris-HCl, 1 mM EDTA, pH 8.0+100 mM dithiothreitol (DTT). After 12-16 hours at RT the pH of the solubilisates was adjusted to 3.0, the centrifuged solutions were dialyzed against 8 M guanidinium hydrochloride, 10 mM EDTA, pH 3.0. The protein concentration was determined by Biuret reaction, the purity of inclusion body preparations was estimated by SDS PAGE. Equimolar amounts of both chains were diluted in two steps into 0.5 M arginine, 2 mM EDTA, pH 10+1 mM GSH/1 mM GSSG, to a final concentration of 0.2-0.3 mg/ml. After 12-16 h at 4-10° C. the renaturated protein was diluted with $H_2O$ to <3 mS/cm and loaded onto a Q Sepharose® FF (GE healthcare) equilibrated in 20 mM Tris/HCl, pH 7.4. Elution was performed with a gradient up to 400 mM NaCl in the same buffer. Fractions containing the correct product were identified by SDS-PAGE and analytical size exclusion chromatography (SEC). Pooled fractions were concentrated and loaded onto a HiLoad™ Superdex™ 200 (GE Healthcare) in 20 mM Tris, 150 mM NaCl, pH 7.4 or alternatively in 20 mM histidine, 140 mM NaCl, pH 6.0. Fractions were analyzed and pooled according to analytical SEC and stored at −80° C.

Based on SEQ ID NO:46 and 49 the immunoconjugate of Fab fragment of M-05-74 with *Pseudomonas* exotoxin variant PE24LR8M (M-05-74-PE) can be expressed recombinately, purified and renaturated also as direct PE24LR8M fusion.

Example 11

Cell Killing of Different Tumor Cell Lines by M-05-74-Fab-*Pseudomonas* Exotoxin Conjugate (M-05-74-PE)

HER3 overexpressing A549 cells were seeded into a white 96-well-plate (flat, transparent bottom, 1×10$^4$ cells per well) and were grown in RPMI (10% FCS) overnight. On the next day, the media was exchanged by 50 µl starving media (RPMI, 0.5% FCS). After at least 4 hours, 5 µl Heregulin-beta (PeproTech, Cat. #100-03) (HRG beta) was added to a final concentration of 500 ng/ml. 50 µl Fab-74-PE solution was added to final concentrations of 10, 3.3, 1.1, 0.37, 0.12, 0.04, 0.014, 0.005 and 0.002 µg/ml. Plates were incubated for 72 h. After 24 h and 48 h, 5 µl Heregulin-beta was added again to a final concentration of 500 ng/ml. After 72 h the luminescence was measured in a Tecan Infinite® F200 Reader using the CellTiter-Glo® Luminescent Cell Viability Assay by Promega (Cat. # G7571). The EC50 value for M-05-74-Fab-*Pseudomonas* exotoxin conjugate (M-05-74-PE) in the absence of HRG beta was: 1.93 µg/ml and in the presence 0.13 µg/ml.

TABLE 10

EC50 of Cell killing of A549 cells by M-05-74-Fab-Pseudomonas

| presence (+)/<br>absence (−) of ligand<br>Heregulin-beta<br>(HRG) | EC50 of (M-<br>05-74-PE)<br>(µg/ml) | half max. inhibition |
|---|---|---|
| +HRG beta | 0.13 | 30.3 |
| −HRG beta | 1.93 | 19.85 |

Example 12a

Humanized Variants of Anti-HER3 Antibody M-05-74

The murine antibody M-05-7 heavy chain and light chain variable domains were used to search for similar human antibody variable domains. From the 200 results obtained for each chain about half were rejected as being from a non-human source. All of the remaining human antibodies were analyzed for key residues within the frameworks that are involved in the VH/VL interface, and for residues that are important for the CDR loop structure. As far as possible these key residues important for the VH/VL interface and canonical loop structure have been maintained in the humanized variants, however certain changes of these positions are included sometimes. The CDRs from the murine antibody chains were grafted into these human antibody frameworks. The top five grafted domains were chosen based upon the previous criteria and also on the results of a T-cell epitope in silico screen for further development. Accordingly the mouse anti-HER3 antibody M-05-74 was humanized to give the following humanized variant VH and VL domains of M-05-74:

TABLE 11

VH and VL sequences of humanized variant antibodies of M-05-74

| humanized variant of VH/SEQ ID<br>NO: | humanized variant of light<br>chain variable domain VL//SEQ<br>ID NO: |
|---|---|
| <Her3> M-05-74_VH-A<br>SEQ ID NO: 33 | <Her3> M-05-74_VL-A<br>SEQ ID NO: 38 |
| <Her3> M-05-74_VH-B<br>SEQ ID NO: 34 | <Her3> M-05-74_VL-B<br>SEQ ID NO: 39 |
| <Her3> M-05-74_VH-C<br>SEQ ID NO: 35 | <Her3> M-05-74_VL-C<br>SEQ ID NO: 40 |
| <Her3> M-05-74_VH-D<br>SEQ ID NO: 36 | <Her3> M-05-74_VL_D<br>SEQ ID NO: 41 |
| <Her3> M-05-74_VH-E<br>SEQ ID NO: 37 | <Her3> M-05-74_VL-E<br>SEQ ID NO: 42 |

From the 25 theoretically possible combinations of these five VH and VL domains the most potent binders were selected as follows:

In order to find a most optimized humanized variant of the <Her3> M-05-74 antibody with the favorable kinetic properties, five variants of each heavy and light chain were designed as described above. The obtained sequences were generated in all combinations (25 in total) in a scFv-ribosome display construct.

The 25 scFv constructs were amplified by flanking primers to obtain linear template DNA, necessary for ribosome display. Each PCR product was purified with agarose gel-electrophoresis followed by extraction with the Qiagen MinElute™ Kit according to the manufacturer's instructions. The product DNA concentration was determined and 200 ng of an equimolar mixture of all linear template DNAs was the basis for the in-vitro transcription/translation at 37° C. for 60 min. The utilized kit comprised the PURExpress® in-vitro protein synthesis kit (NEB), including both disulfide bond enhancers (DBE 1 & 2). Two reaction samples were processed, with the doubled reaction amount per sample. The first sample included the biotinylated and heregulin activated target (Her3-ECD) in the subsequent panning step. The second sample was the negative control, without target protein in the panning step. Both samples were treated identically. The obtained pools of ternary complexes (mRNA-ribosome-scFv variant) after transcription and translation were subjected to a pre-panning step with the employed magnetic beads (Streptavidin M-270 Dynabeads, Life Technologies) for 30 min at 4° C. to remove unspecific binding variants. The pre-panning beads were removed by centrifugation and the supernatant with the remaining ternary complexes was added to the prepared target/heregulin mixture to incubate for 30 min at 4° C. in the panning step. The target/heregulin complex was incubated in a 1:6 molar ratio for 60 min previous to the panning step to obtain the open conformation of the receptor domain and to expose the epitope of the 74 parental antibody. The final concentration of biotinylated Her3-ECD in the panning reaction was 100 nM. All employed buffers hereafter contained 300 nM heregulin.

The target and all binding ternary complexes were captured via the targets biotin taq and the above mentioned streptavidin beads. Incubation time for capturing was 20 min at 4° C. Utilizing the magnetic properties of the beads the complexes can be washed by repeated incubation and removal of the wash buffer. In order to remove weak binding variants the wash pressure was increased over the washing steps. In total five washing steps with 500 uL of wash buffer (containing Heregulin) were employed (2, 4, 5, 5 & 1 min) with 2 min of capturing in the magnetic field in between. The last step was used to transfer the remaining strong binding variants in a clean new reaction tube for the elution step (10 min, 4° C., 100 uL elution buffer containing EDTA) followed by centrifugation to remove the beads. The obtained RNA in the supernatant was purified with the Qiagen RNEasy RNA purification kit according to the manufacturer's instructions. In order to ensure the origin of the later produced DNA by reverse transcription, the RNA was beforehand subjected to an DNAse digestion. The digest (Ambion DNA-free Kit) was initiated with 12 uL of purified RNA and incubated for 30 min at 37° C. Following the removal of DNase, three reverse transcription reactions per sample were initiated with 12 uL each and incubated for one hour at 37° C. 12 uL of each digested RNA sample (digested product) were used as negative control for the first PCR to proove the complete removal of DNA traces.

The products of the reverse transcription reactions were pooled for each sample and used to initiate five 100 uL PCR reactions to amplify the DNA selection pools. The products were pooled and purified by gel electrophoresis (1% preparative agarose gel and analytical Agilent DNA 7500 chip with 1 uL sample volume) and the Qiagen MinElute Kit according to the manufacturer's protocols. The obtained gel image in FIG. 1 clearly shows enrichment of selected construct DNA in lane 1 and no enrichment for the negative control—panning without target—in lane 2. The remaining controls are also negative as expected. The DNA digest was complete (lane 3 for target, lane 4 for background). Therefore all obtained DNA in lane 1 is derived from binding variants, selected in the panning step, and their corresponding RNA. Neither the negative control of the reverse transcription, nor the negative control of the PCR is showing bands. Lane 7 shows the product of the pooled PCR reactions after purification.

The PCR product was amplified to produce enough DNA for cloning. The selection pool and the expression vector Her_scFv_huFc (1 ug each) were digested with MfeI-HF and NotI-HF in CutSmart® buffer (all NEB) for one hour at 37° C. The selection insert and the cut vector were first purified and then ligated with NEB Quick Ligase for 30 min at room temperature. The molar ratio of cut insert to vector was 5:1 (25 ng cut insert and 50 ng cut vector). Two microliters of the ligation product were directly used to transform 50 uL of DHSα (Life Technologies) competent cells. Following outgrowth, 50 uL were plated out on LB plates with ampicillin resistance (LBamp) and incubated for 16 hours at 37° C. 34 colonies were used to inoculate 5 mL LBamp media for 16 h at 37° C. The cells were harvested and the DNA isolated with the Qiagen Miniprep Kit according to the manufacturer's instructions and 300 ng plasmid DNA of each sample was sent to Sequiserve GmbH for sequencing.

Results—Most Optimized Humanized Variant of <Her3> M-05-74 Antibody

The sequencing results show an enrichment of one particular variant: VH-A/VL-D. The corresponding sequence was obtained six times from the 34 samples, which clearly indicates the most potent binding properties to HER-ECD in the assay described above.

Also the combinations VH-A/VH-B and VH-A/VH-E occurred twice and hence showed some superior binding properties to HER3 ECD as compared to the remaining less enriched VH/VLcombinations.

Surpisingly all enriched variants included VH-A. Consequently VH-A is a key feature of all HER3 binding humanized variants of <Her3> M-05-74., especially in the preferred combinations VH-A/VL-D, VH-A/VH-B and VH-A/VH-E.

The remaining 24 sequences were all different and featured minor deletions and/or a combination of point mutations. Three sequences could not perfectly be edited and were not analyzed.

Each of the combinations VH-A/VL-D, VH-A/VH-B and VH-A/VH-E. is expressed in a human IgG1 isotype (with Ckappa light chain constant domain) or alternatively e.g. as fusion protein with a *Pseudomonas* exotoxin (immunotoxin) as described above. Binding characteristics and biological properties are determined as describe above e.g. in Example 2, 3, 5, 6, 7, 8, 9, 11 or described in Example 13 below.

Example 12b

Binding of Humanized Variants of Anti-HER3 Antibody M-05-74

To investigate the binding of the humanized variant VH-A/VL-D of anti-HER3 antibody M-05-74 (described in Example 12a) to the HER3-ECD and the HER4-ECD, in presence and absence of the ligand Heregulin, SPR analysis were conducted at 37° C., using a Biacore™ 3000 device (GE Healthcare) (Table 11).

TABLE 11a

SPR analysis of humanized variant VH-A/VL-D at 37°C.:
Binding of humanized DIB-74 to HER3-ECD and HER4-ECD
in presence and absence of the ligand FRG, investigated
using a Biacore ™ 3000 device (GE Healthcare)

| Analyte | $k_a$ (M$^{-1}$s$^{-1}$) | $k_d$ (s$^{-1}$) | $t_{1/2diss}$ (min) | $K_D$ (nM) | $R_{max}$ (RU) | MR | Chi$^2$ (RU$^2$) |
|---|---|---|---|---|---|---|---|
| HER3-ECD | 1.9E+04 | 4.4E−04 | 26 | 23 | 80 | 0.7 | 0.2 |
| HER4-ECD | n. d. | n. d. | n. d. | n. d. | n. d. | n. d. | n. d. |
| HER3-ECD/HRG | 1.9E+05 | 2.0E−03 | 6 | 10 | 198 | 0.8 | 1.4 |

TABLE 11a-continued

SPR analysis of humanized variant VH-A/VL-D at 37°C.:
Binding of humanized DIB-74 to HER3-ECD and HER4-ECD
in presence and absence of the ligand FRG, investigated
using a Biacore ™ 3000 device (GE Healthcare)

| Analyte | $k_a$ (M$^{-1}$s$^{-1}$) | $k_d$ (s$^{-1}$) | $t_{1/2diss}$ (min) | $K_D$ (nM) | $R_{max}$ (RU) | MR | Chi$^2$ (RU$^2$) |
|---|---|---|---|---|---|---|---|
| HER4-ECD/HRG | 1.8E+05 | 3.8E−02 | 0.3 | 211 | 183 | 0.8 | 0.5 |

TABLE 11b

Direct comparison with parent murine anti-HER3 antibody M-05-74

| Analyte | $k_a$ (M$^{-1}$s$^{-1}$) | $k_d$ (s$^{-1}$) | $t_{1/2diss}$ (min) | $K_D$ (nM) | $R_{max}$ (RU) | MR | Chi$^2$ (RU$^2$) |
|---|---|---|---|---|---|---|---|
| HER3-ECD | 2.1E+04 | 8.1E−05 | 144 | 4 | 104 | 0.6 | 0.2 |
| HER4-ECD | n.d. | n.d. | n.d. | n.d. | n.d. | n.d. | n.d. |
| HER3-ECD/HRG | 7.9E+04 | 5.7E−04 | 20 | 7 | 225 | 0.7 | 2.6 |
| HER4-ECD/HRG | 5.8E+05 | 3.3E−03 | 4 | 6 | 289 | 0.9 | 5.4 |

The humanized variant VH-A/VL-D of anti-HER3 antibody M-05-74 preferentially bound to the ligand activated ECD complexes, due to increased epitope accessibility. It bound with an affinity of $K_D$ 10 nM to the HER3-ECD/HRG complex Surpisingly the humanized variant VH-A/VL-D of anti-HER3 antibody M-05-74 showed a strongly reduced HER4-ECD/HRG reactivity ($K_D$ 211 nM) compared to the parent antibody M-05-74 (($K_D$ 4 nM)) while retaining its HER3-ECD/HRG reactivity ($K_D$ 10 nM compared to $K_D$ 7 nM).

Example 13

In Vivo Tumor Cell Growth Inhibition by M-05-74-Fab-*Pseudomonas* Exotoxin Conjugate (M-05-74-PE)

The human A431-B34 non-small cell lung cancer cell line cell line, which was stably transfected with an expression vector encoding human HER3, was subcutaneously inoculated into the right flank of female SCID beige mice (1×10$^7$ cells per animal).

On day 21 after tumor inoculation, the animals were randomized and allocated into the treatment group and one vehicle group, resulting in a median tumor volume of ~110 mm$^3$ per group. On the same day, animals were treated intravenously for 2 cycles, each cycle consisting of 3q7d (every other day), with M-05-74-Fab-*Pseudomonas* exotoxin conjugate (M-05-74-PE) (1.0 mg/kg). Controls received vehicle (Tris buffer). The two cycles were separated by a one week off-treatment.

Primary tumor volume (TV) was calculated according to the NCI protocol (TV=(length×width$^2$)/2), where "length" and "width" are long and short diameters of tumor mass in mm (Corbett et al., 1997). Calculation was executed from staging (day 21 after tumor inoculation) until day 42 after tumor inoculation, and values were documented as medians and inter-quartile ranges (IQR) defined as differences of the third and first quartile.

For calculation of percentage tumor growth inhibition (TGI) during the treatment period, every treated group was compared with its respective vehicle control. TV$_{day\ z}$ represents the tumor volume of an individual animal at a defined study day (day z) and TV$_{day\ x}$ represents the tumor volume of an individual animal at the staging day (day x).

The following formula was applied:

$$TGI\ [\%] = 100 - \frac{\text{median } (TV \text{ (treated)}_{day\ z} - TV \text{ (treated)}_{day\ x})}{\text{median } (TV \text{ (resp. control)}_{day\ z} - TV \text{ (resp. control)}_{day\ x})} \times 100$$

Figure 19:
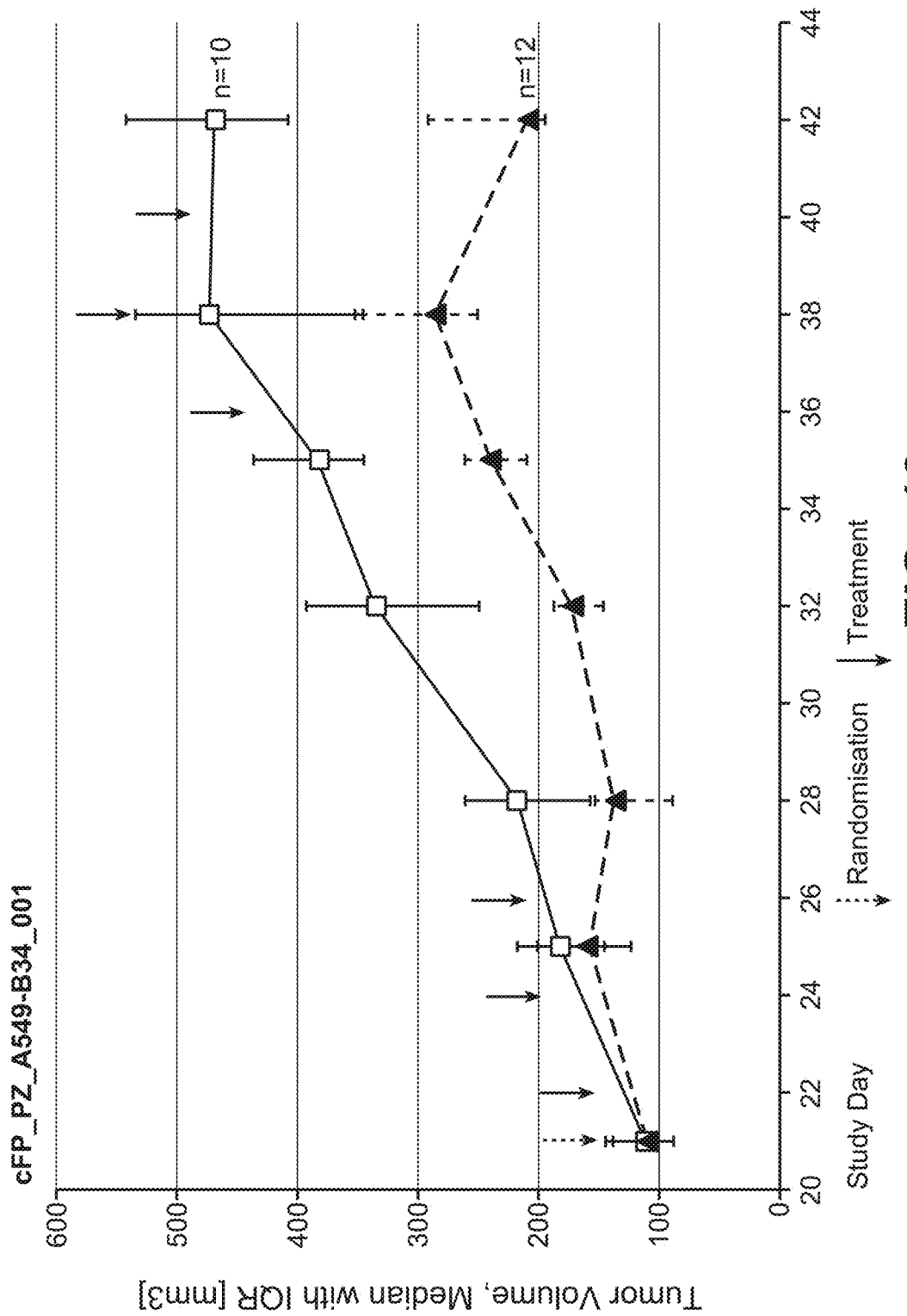
FIG. 19 In vivo tumor cell growth inhibition by M-05-74-Fab-*Pseudomonas* exotoxin conjugate (M-05-74-PE). Legend: closed line (vehicle); dotted line (M-05-74-Fab-*Pseudomonas* exotoxin conjugate (M-05-74-PE)).

Calculations of treatment to control ratio (TCR) with confidence interval (CI) were applied using non-parametric methods. Results of median tumor volumes with inter-quartile ranges are shown in FIG. 19. Tumor growth inhibition was 66% of M-05-74-Fab-*Pseudomonas* exotoxin conjugate (M-05-74-PE) with a TCR of 0.509 (CI:0.33-0.734).

Example 14

Binding of the Antibody M-05-74 (1) to TtSlyDcys-Her3 (SEQ ID NO: 18) in Comparison with Anti-HER3 Antibody MOR09823 (2) Described in WO2012/22814.

A Biacore™ T200 instrument (GE Healthcare) was mounted with CM5 series sensor and was normalized in HBS-ET+ buffer (10 mM HEPES pH 7.4, 150 mM NaCl, 3 mM EDTA, 0.05% w/v Tween 20) according to the manufacturer's instructions. The sample buffer was the system buffer supplemented with 1 mg/ml CMD (Carboxymethyldextran). The system operated at 37° C. A double antibody capture system was established on the sensor surface. 6500 RU mAb<M-IgG>R was immobilized according to the manufacturer's instructions using EDC/NHS chemistry on all flow cells. The sensor was deactivated using 1M ethanolamine. Flow cell 1 served as a reference and was captured for 1 min at 10 µl/min with anti-TSH IgG1 antibody. On flow cell 2 M-5-74 was captured for 1 min at 10 µl/min. On flow cell 3 a murine anti-human FC pan antibody was captured 1 min at 10 µl/min followed by the injection of the anti-HER3 antibody M-05-74 (1) or of anti-HER3 antibody MOR09823 antibody for 1 min at 10 µl/min. The flow rate was set to 60 µl/min. The analyte in solution TtSlyDcys-HER3 (SEQ ID NO: 18) was injected at concentrations of 0 nM and 150 nM for 5 min and the dissociation was monitored for 600 sec. The sensor was fully regenerated by one injection at 10 µl/min for 3 min with 10 mM glycine pH 1.7 buffer.

Figure 20:
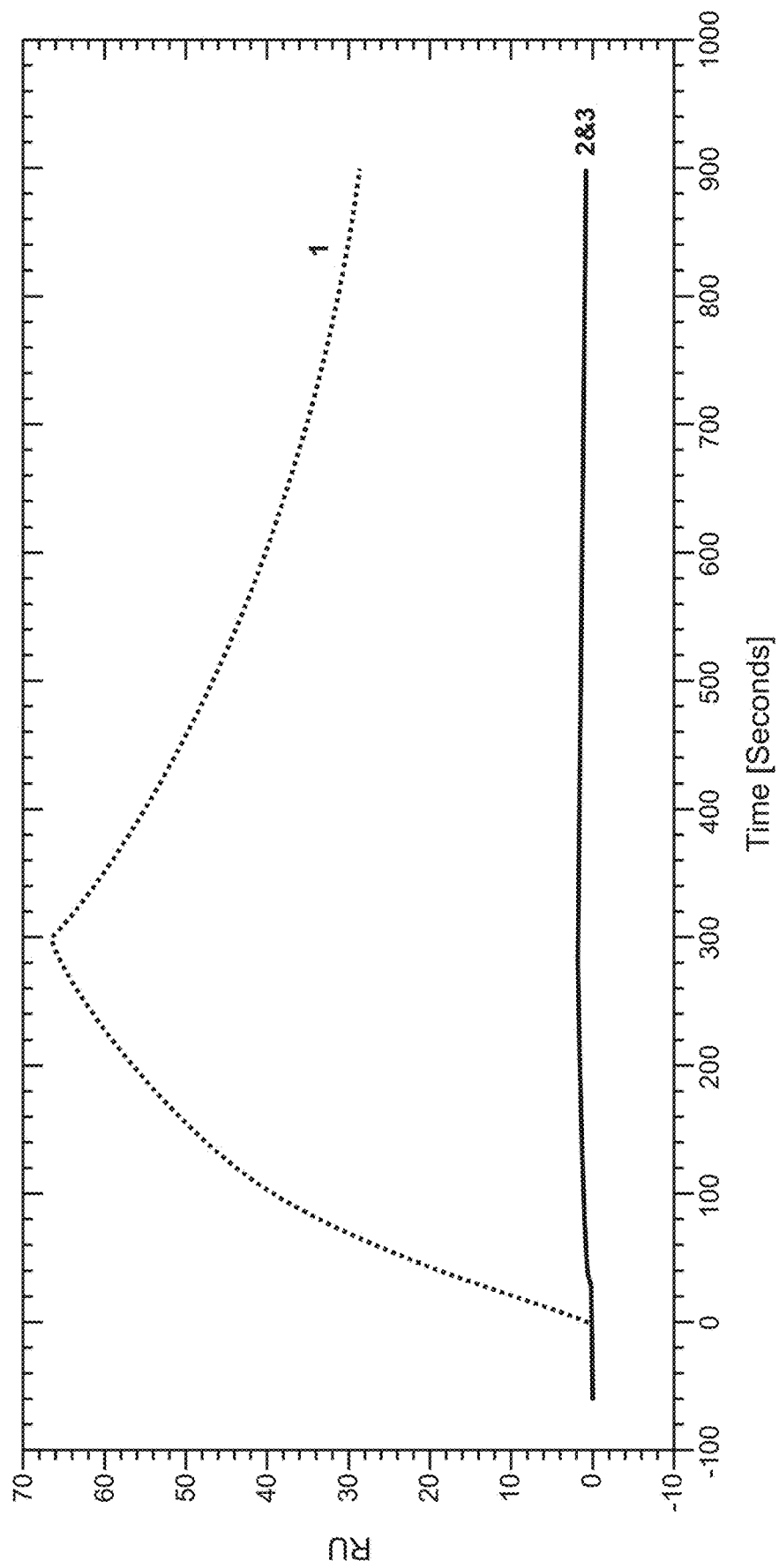
FIG. 20 Biacore™ sensorgram overlay plot: binding of the antibody M-05-74 (1) of the present invention to TtSly-Dcys-Her3 (SEQ ID NO: 18) in comparison with anti-HER3 antibody MOR09823 (2) described in WO2012/22814. While the antibody of the present M-05-74 (1) shows a clear binding signal to TtSlyDcys-Her3 (SEQ ID NO: 18), the antibody anti-HER3 antibody MOR09823 (2) shows no binding at all to TtSlyDcys-Her3 (SEQ ID NO: 18). Control measurement (3) without antibody at all did not show any binding to TtSlyDcys-Her3 (SEQ ID NO: 18).
Figure 21:
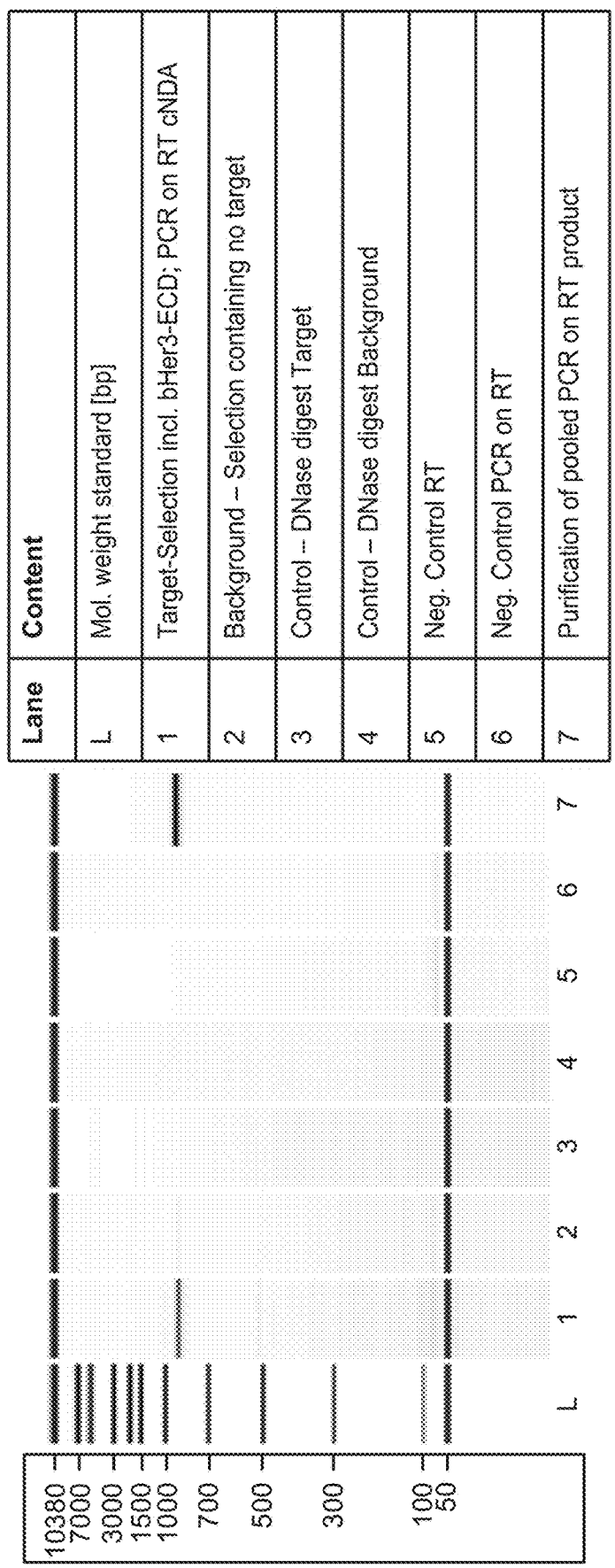
FIG. 21 Selection of optimized humanized M-05-74 antibody via ribosome display: Analytical DNA chip electrophorese of PCR products obtained after reverse transcription of the enriched RNA during display selection. The obtained gel image shows enrichment of selected construct DNA in lane 1 and no enrichment for the negative control—panning without antigen—in lane 2. The remaining controls are also negative as expected. The DNA digest was complete (lane 3 for target, lane 4 for background). Therefore all obtained DNA in lane 1 is derived from binding variants, selected in the panning step, and their corresponding RNA. Neither the negative control of the reverse transcription, nor the negative control of the PCR is showing bands. Lane 7 shows the product of the pooled PCR reactions after purification.
Figure 22:
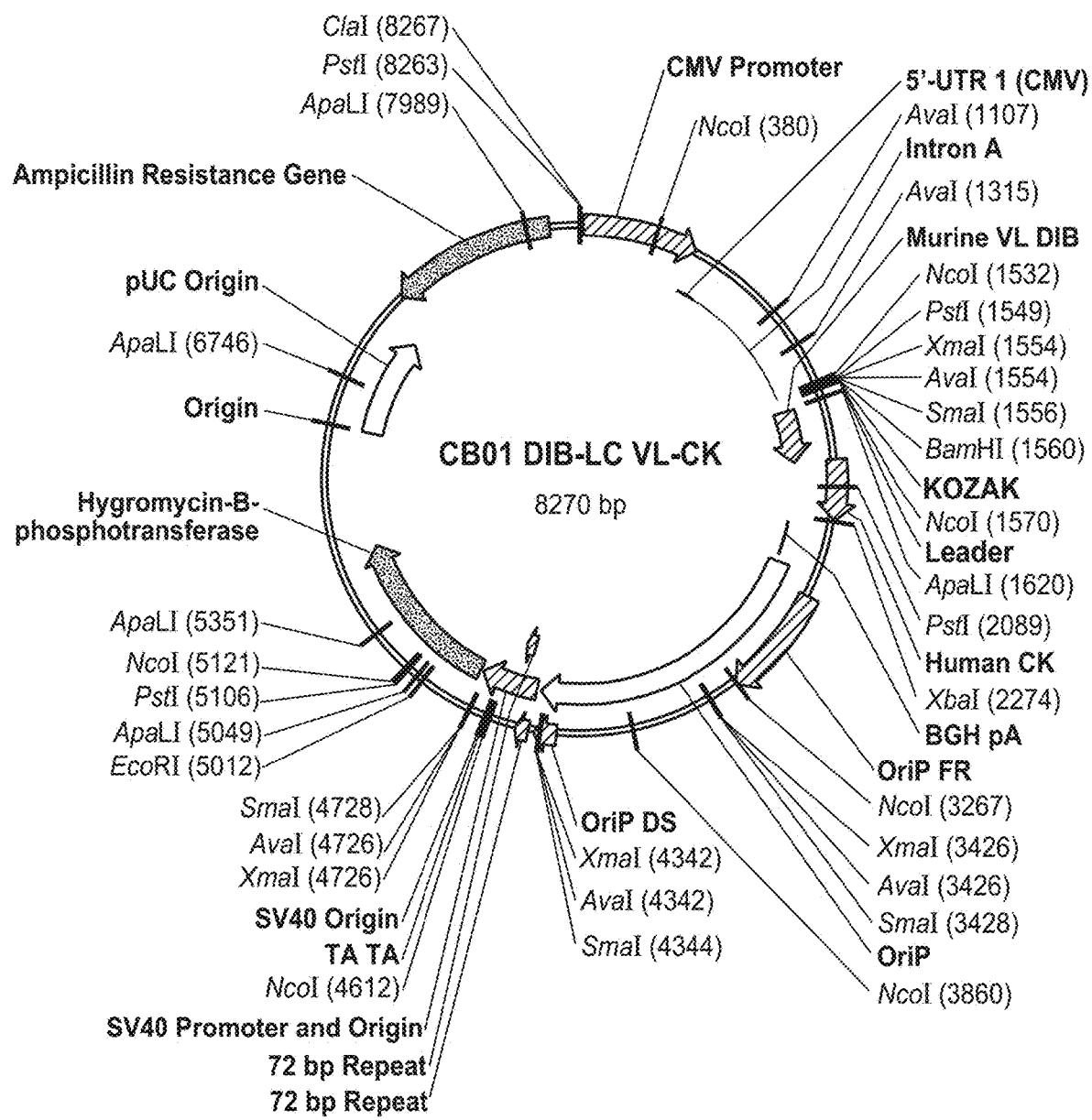
FIG. 22 Expression vector construct-DIB light chain (VL-CK).
Figure 23:
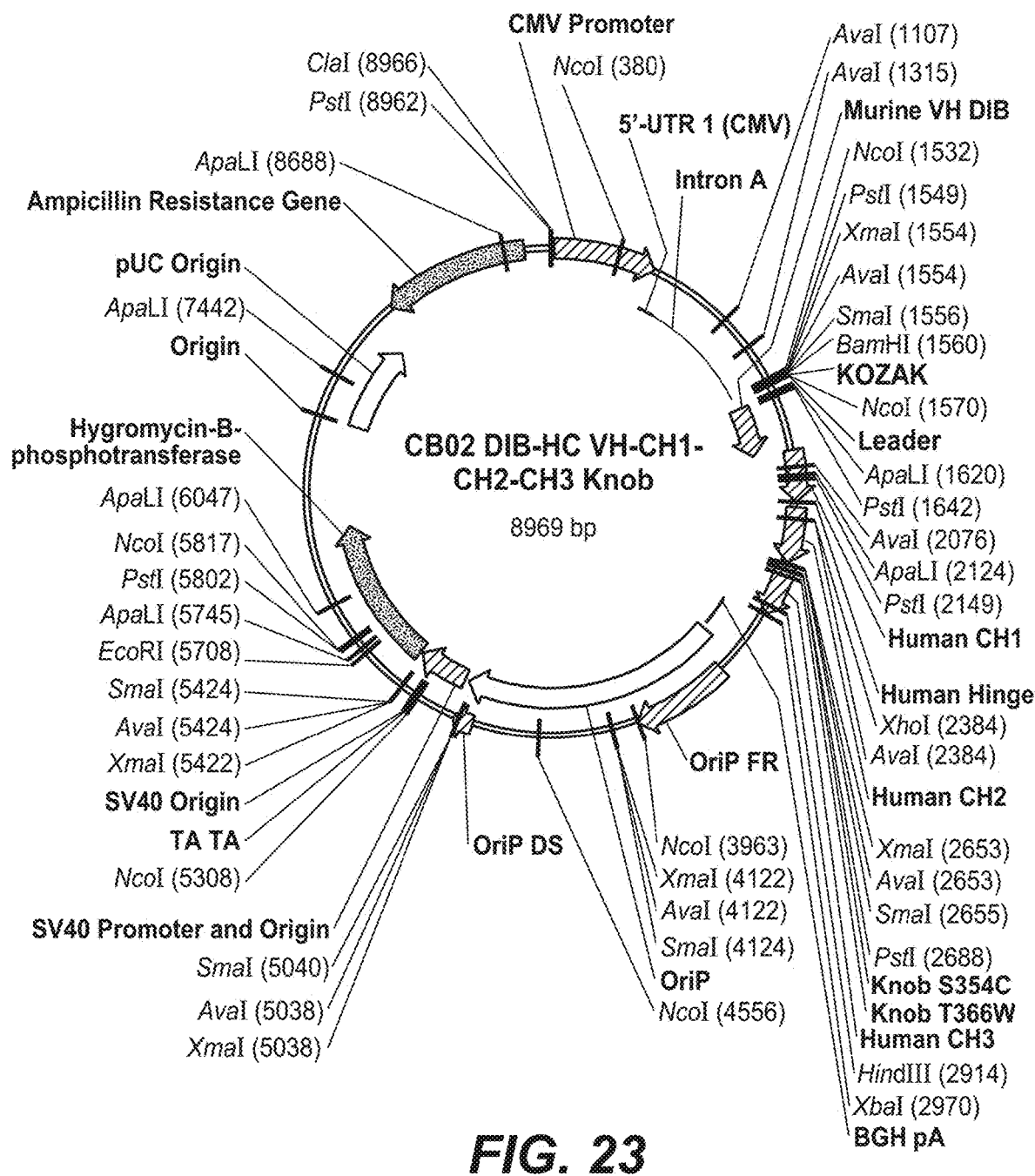
FIG. 23 Expression vector construct-DIB heavy chain with 'knob' amino acid in CH3 (VH-CH1-CH2-CH3 (knob)).
Figure 24:
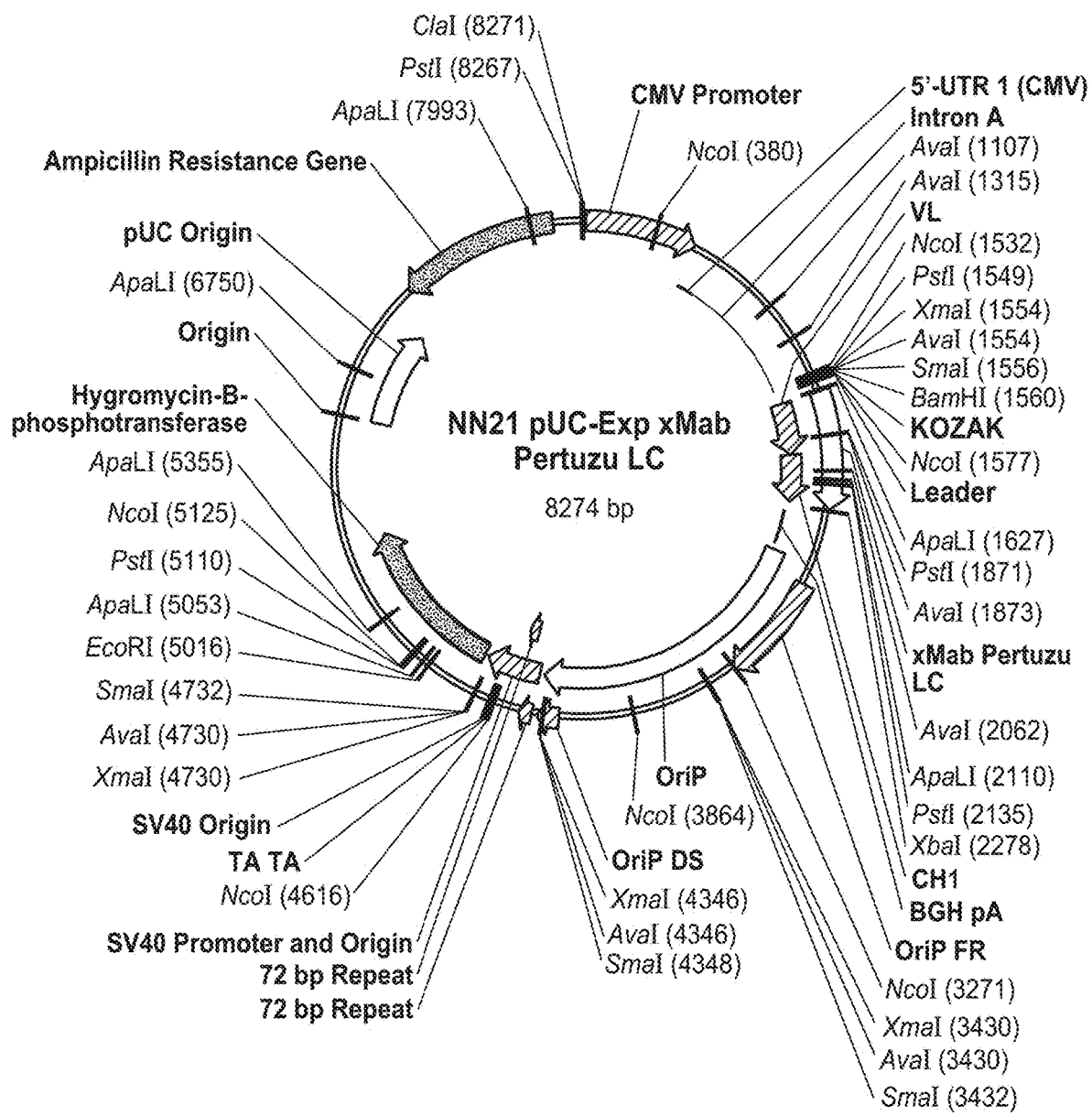
FIG. 24 Expression vector construct-Pertuzumab crossed light chain (VL-CH1).

FIG. 20 depicts a sensorgram overlay plot showing binding signals at 150 nM of, TtSlyDcys-Her3 and buffer. The overlay plot above shows the antibody M-5-74 binding at 150 nM TtSlyDcys-Her3 (1). MOR09823 antibody does not bind TtSlyDcas-Her3 (2). (3) shows the background binding signal of the TtSlyDcas-HER3 versus the mAb<M-IgG>R capture surface. The anti-HER3 antibody MOR09823 (2) described in WO2012/22814 does not show any interaction at 150 nM TtSlyDcys-Her3. The positive control antibody M-05-74 (1) shows significant binding versus TtSlyDcas-Her3. No interaction could be determined with both antibodies when injecting 150 nM TtSlyDcys (no HER-3 insertion) (data not shown).

Example 15

Figure 25:
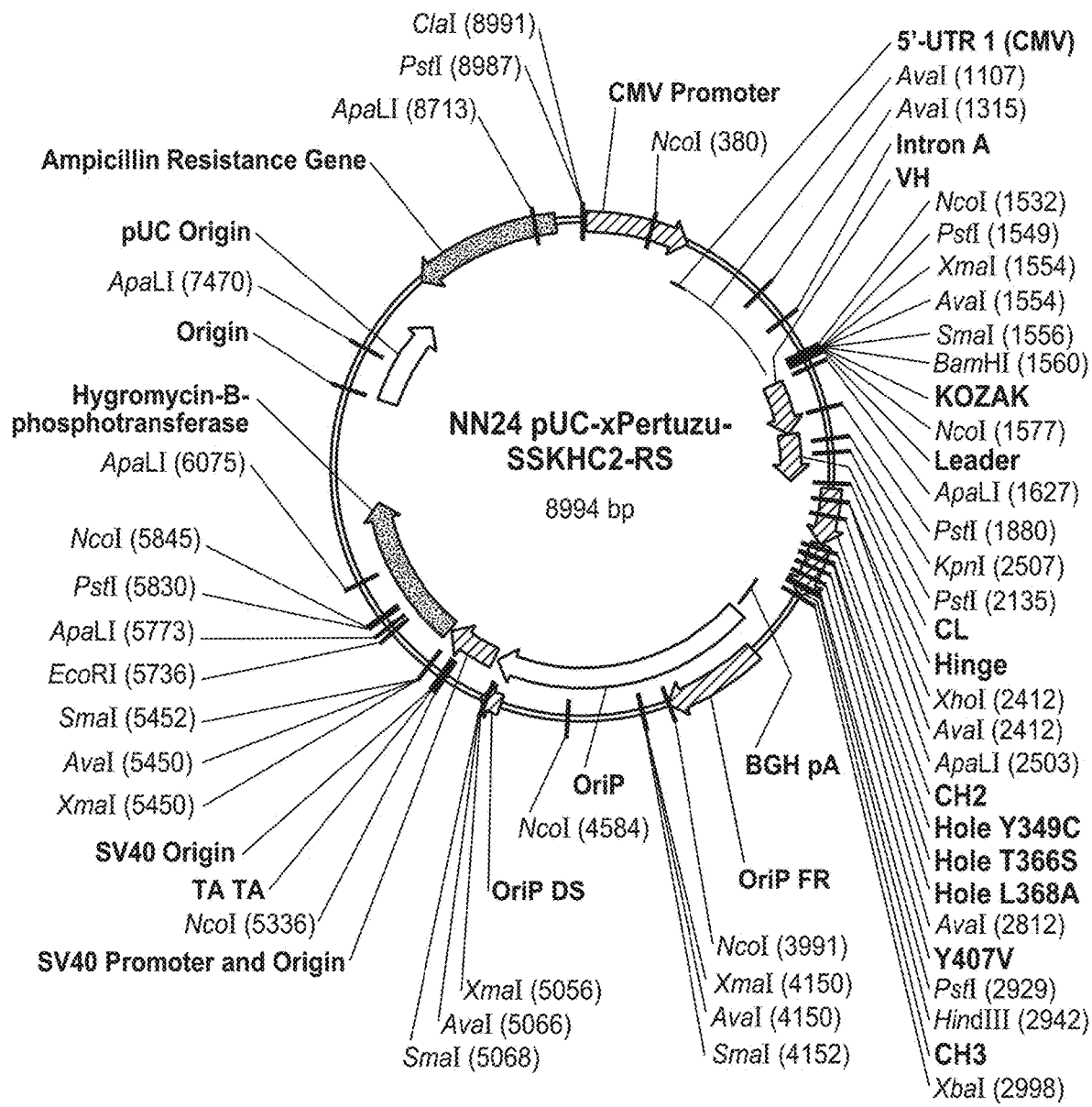
FIG. 25 Expression vector construct-Pertuzumab crossed heavy chain with 'hole' mutation in CH3 (VH-CK-CH2-CH3(hole)).
Figures 26A, 26B:
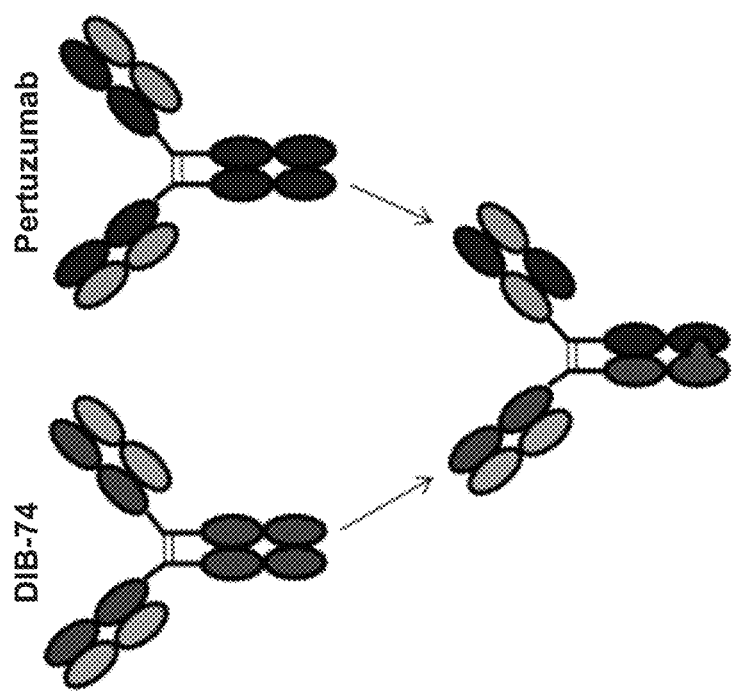
FIGS. 26A-B (A) Layout of the bispecific CrossMab DIBxPERT as a hybrid of DIB-74 and Pertuzumab: The Scheme shows the bispecific CrossMab DIBxPERT and its parental antibodies DIB-74 and Pertuzumab. DIB-74 and Pertuzumab bind to the β-hairpins of the HER3-ECD and the HER2-ECD, respectively. Dark colors indicate Ig heavy chains, light colors Ig light chains. The CH3 Ig domains contain 'knob' or 'hole' mutations, according to the 'knob-into-hole' technology. A domain cross-over of CH1 and CK of the Pertuzumab heavy and light chain was designed to facilitate the correct light chain-heavy chain assimilation. (B) Scheme of DIB-MoAb, an artificial monovalent antibody format as a derivative of DIB-74. The 'knob-into-hole' technology and a CH1-CK domain cross-over were applied.

Generation and Evaluation of HER3/HER2 Bispecific Antibody DIBxPERT Binding to the Beta-Hairpin of HER3 and Domain II of HER2
Material and Methods
Recombinant DNA Techniques Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.
Gene Synthesis Desired gene synthesis fragments were ordered according to given specifications at Geneart (Regensburg, Germany). The 600-1500 bp long gene segments, which were flanked by singular restriction endonuclease cleavage sites, were cloned via the indicated restriction sites into a pUC expression vector, e.g. BamHI/XbaI, BamHI/XhoI (FIGS. 22-25). The DNA sequences of the subcloned gene fragments were confirmed by DNA sequencing.
DNA Sequence Determination DNA sequences were determined by double strand sequencing performed at Sequiserve GmbH (Vaterstetten, Germany).
DNA and Protein Sequence Analysis and Sequence Data Management Infomax's Vector NT1 Advance® suite version 11.5.0 was used for sequence creation, mapping, analysis, annotation and illustration.
CrossMab Design The CrossMab technology (Schaefer et al. 2011) combines two heavy and light chains of different parental antibodies with different specificities into one IgG-like format. To facilitate heterodimerization of two different heavy chains, the 'knob-into-hole' technology is applied, whereby one smaller amino acid is exchanged by a larger amino acid in one CH3 domain ('knob'). In the CH3 domain of the second antibody, a larger amino acid is exchanged by smaller amino acids ('hole'). To ensure the correct assimilation of light chains with corresponding heavy chains, the CH1 domain of one heavy chain is exchanged with the CKappa (CK) domain of the respective light chain. The end product in general is called CrossMab. Here, the M-05-74 (DIB-74) antibody light (FIG. 22) and heavy chain (FIG. 23) were used, whereby a 'knob' mutation was introduced into the CH3 domain of the DIB heavy chain. As a second parental antibody Pertuzumab was used. Here, the crossing-over was induced between the CK domain of the light chain (FIG. 24) and the CH1 domain of the heavy chain (FIG. 25). In the CH3 domain 'hole' mutations were introduced. The resulting CrossMab is called DIBxPERT (see sequences SEQ ID NOs 68-71, whereby the x in front of PERT (Pertuzumab) indicates, that the cross-over was introduced in the Pertuzumab site (FIG. 26).
Expression of DIBxPERT For the expression of DIBxPERT by HEK293F cells, plasmid DNA was obtain by QIAGEN Plasmid Plus Maxi Kit (Qiagen, Hilden, Germany), according to the manufacturer's indications. Cells were seeded with 1.0E+06 cells per ml Gibco® FreeStyle™ 293 Expression Medium. One liter of cells was transfected with 22 pmol of each of the four plasmids (CB01_DIB-LC_VL-CK, CB02_DIB-HC_VH-CH1-CH2-CH3_knob, NN21 pUC-Exp_xMab_Pertuzu_LC, NN24 pUC-xPertuzu-SSKHC2-RSE), using the 293-Free™ Transfection Reagent, according to the manufacturer's instructions. Cells were incubated for seven days at 37° C., 8% CO2 and 80% air humidity, shaking at 150 rpm (LabTherm LT-XC, Kühner AG, Birsfelden, Schweiz). After incubation, 50 mM PMSF (Sigma-Aldrich, Steinheim, Germany), 1 ng MgCl2 (Merck GmbH, Darmstadt, Germany) and 10 U/ml DNaseI (Roche Diagnostics GmbH, Mannheim, Germany) were added and cells were incubated for 30 minutes. The antibody containing supernatant was harvested by pelleting the cells for 30 minutes at 890×g (Rotanta 460R, Andreas Hettich GmbH, Tuttlingen, Germany). Until purification, the supernatant was stored at −20° C.

Purification of DIB×PERT

Figures 27A, 27B, 27C:
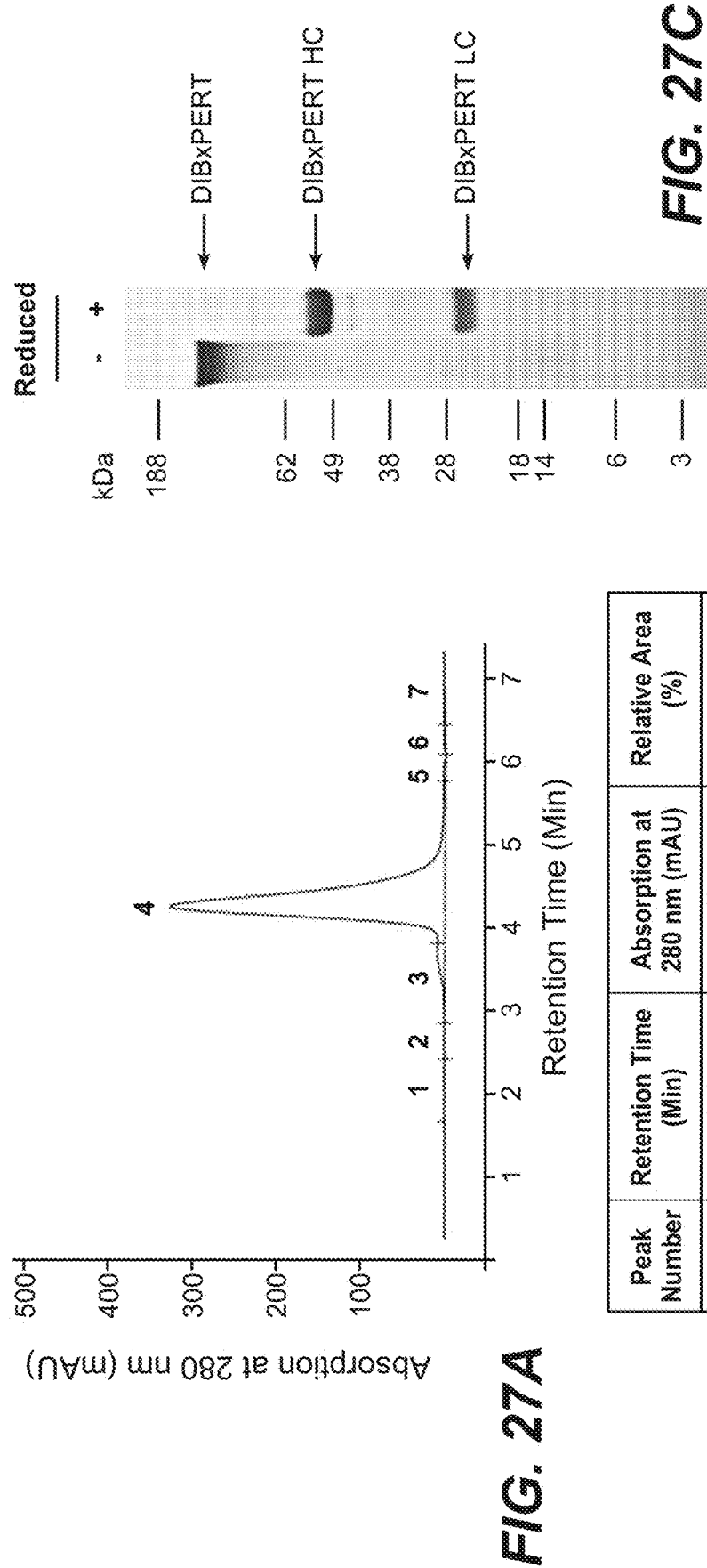
FIGS. 27A-C Qualitative analytic of the purified DIBx PERT CrossMab by GPC and SDS-PAGE: The DIBxPERT end product quality was assessed, using GPC and SDS-PAGE. (A) Analytic GPC peaks were numbered consecutively (1-7). (B) Tabular presentation of all seven GF30 peaks, listing retention times, absorption at 280 nm and the relative peak area in percentage. (C) The Coomassie staining of a 4-12% SDS-PAGE showing the DIBxPERT end product under reducing (+) and non-reducing (−) conditions. DIBx PERT and DIBxPERT heavy and light chains are indicated by arrows.

The antibody was isolated using an ÄktaAvant instrument (GE Healthcare, München, Germany). A protein A HiTrap MabSelect SuRe™ (5 ml) (GE Healthcare, München, Germany) was equilibrated with 50 mM $KH_2PO_4$, 150 mM KCl, pH 7.4 system buffer. The supernatant was filtered with 0.22 µm sterile filter units beforehand and then applied onto the column with a flow rate of 0.9 ml/min overnight. Subsequently, unbound material was removed, using the system buffer at a flow rate of 2 ml/min. Then, bound antibodies were eluted from the column using 0.1 M Na-Citrate pH 3.7 at a flow rate of 1 ml/min and directly neutralized with 1 M L-Arginine buffer. Desired fractions were pooled and purified by gel permeation chromatography (GPC), thereby dialyzing the buffer into 20 mM Histidine, 140 mM NaCl, pH 6.0 storage buffer. The DIB×PERT end-product quantity was analyzed by spectroscopy at 280 nm. The quality was controlled by GPC, using a TSK-Gel® QC-PAK GF30 column (Tosoh Bioscience GmbH, Stuttgart, Germany) and a UltiMate™ 3000 Dionex instrument (Fisher Scientific GmbH, Schwerte, Germany) (FIGS. 27 A and B). As a second quality control a 4-12% Bis-Tris SDS-PAGE (Life Technologies GmbH, Darmstadt, Germany) was used, with reducing and non-reducing conditions (FIG. 27 C). By reducing conditions the covalent disulfidbridges between heavy and light chains are disrupted.

To assess the purity and aggregation state of DIB×PERT, an analytical GPC was conducted, using a TSK-Gel® QC-PAK GF30 column (Tosoh Bioscience, Stuttgart, Germany). DIB×PERT was purified with a relative GPC peak area of 96% (FIG. 27 A). Comparison with the standard curve reference confirmed a molar mass of 145 kDa. The SDS-PAGE (FIG. 27 B) revealed a protein band at approximately 145 kDa under non-reducing condition. Under reducing-condition the disulfide bonds between heavy and light chains are disrupting. Therefore, two bands were found in the SDS-PAGE, which could be assigned to the heavy (approx. 50 kDa) and light (approx. 25 kDa) antibody chains (FIG. 27 C). The purity of the DIB×PERT end product was adequate for subsequent experiments and analyses.

Example 16

Determination of HER3/HER2 Bispecific Antibody DIB×PERT Kinetic Features by SPR Analyses In its equilibrium state, the HER3-ECD is in its "closed confirmation", which does mean, the heterodimerization HER3 β-hairpin motive is tethered via non-covalent interactions to the HER3-ECD domain IV. It is supposed, that the "closed" HER3 conformation can be opened via the binding of the ligand heregulin at a specific HER3 heregulin binding site. This takes place at the HER3 interface formed by the HER3-ECD domains I and domain III. By this interaction it is believed, that the HER3 receptor is activated and transferred into its "open conformation". When this occurs, the HER3 β-hairpin is accessible for the described antibodies. This mode of action can be simulated in vitro by a Biacore™ experiment.

To investigate, if the kinetic features of parental antibodies DIB-74 and Pertuzumab were retained by DIB×PERT, real-time data were collected, using SPR analyses, a Biacore™ B3000 instrument (GE Healthcare) was used to kinetically assess the monoclonal antibodies at 25° C. for their behavior to the heregulin-activated HER3 Extracellular Domain (HER3-ECD) and the constitutive open HER2-ECD. A CM5 series sensor was mounted into the system and was normalized in HBS-ET buffer (10 mM HEPES pH 7.4, 150 mM NaCl, 3 mM EDTA, 0.005% w/v Tween 20) according to the manufacturer's instructions. The sample buffer was the system buffer supplemented with 1 mg/ml CMD (Carboxymethyldextran, Sigma #86524). The system operated at 25° C. 10000 RU monoclonal murine anti-human Fc antibody (MAK<h-Fc>M-R10Z8E9, Roche Diagnostics GmbH, Penzberg, Germany) were immobilized using EDC/NHS chemistry on all four flow cells. The sensor was deactivated using 1M ethanolamine.

Figure 28:
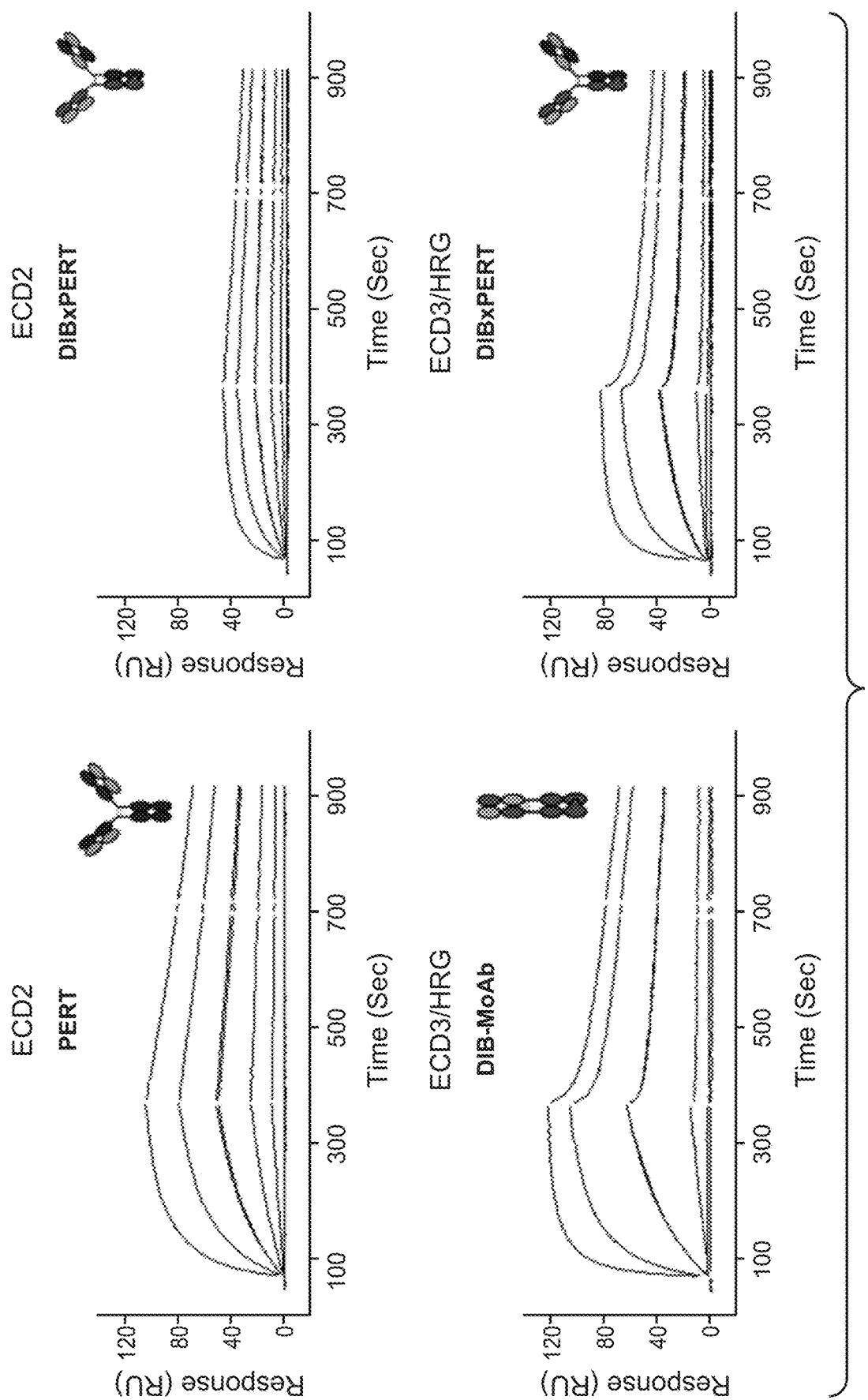
FIG. 28 Comparison of kinetic characteristics of DIBx PERT and the parental antibodies by SPR: Antibodies were captured on a CM5 sensor chip surface and kinetic interactions at 25° C. with soluble analytes were measured, using a Biacore™ B3000 instrument (GE Healthcare, Munchen, Germany). Analytes were injected for 5 minutes and dissociation was recorded for 10 minutes. The analytes HER2-ECD and HER3-ECD/HRG1β were injected in a five-step 1:3 series dilution with a highest concentration of 270 nM.
Figure 29A:
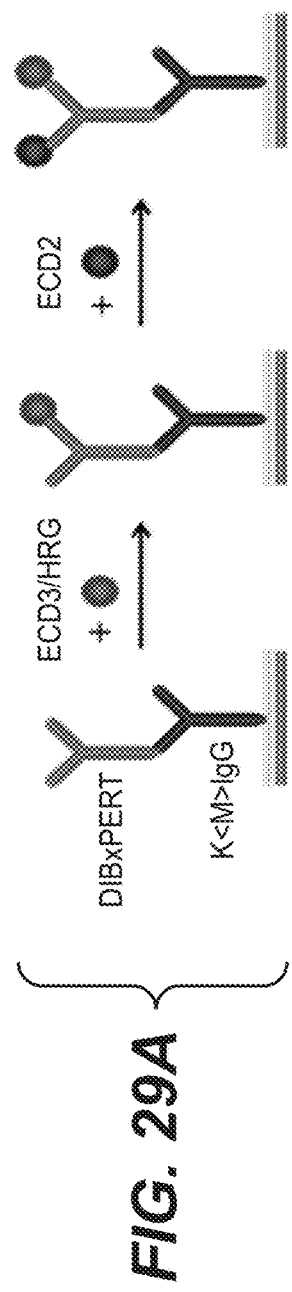
FIGS. 29A-D Simultaneous complex-formation of HER2-ECD and activated HER3-ECD by DIBxPERT in solution: Antibodies were captured on a CM5 sensor chip surface and kinetic interactions at 25° C. with soluble analytes were measured, using a Biacore™ B3000 instrument (GE Healthcare, Munchen, Germany). Analytes HER2-ECD and HER3-ECD/HRG1β were sequentially injected for 8 minutes and dissociation was recorded for 5 minutes. (A and C) Assay setup for sensorgrams (B) and (D), respectively. (B and D) The sensorgrams show the sequential binding of both analytes. Analyze injections and the molar ratio are indicated with arrows and 'MR', respectively.
Figure 29B:
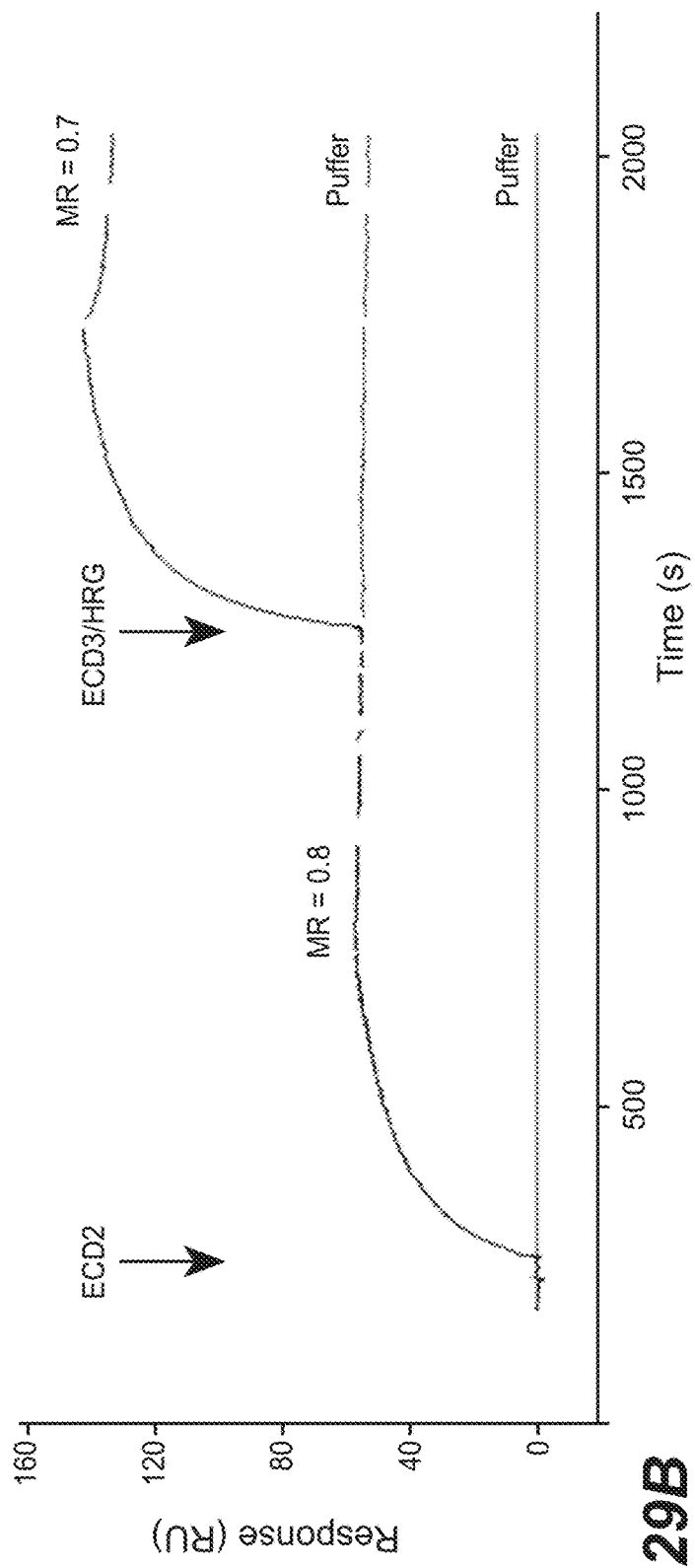
Figure 29C:
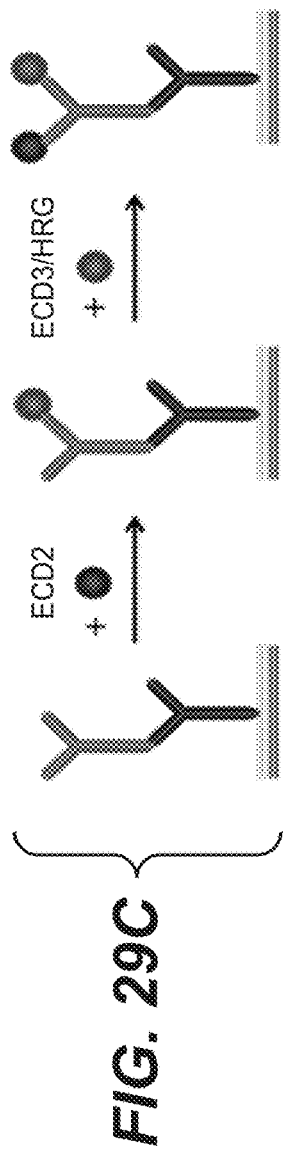
Figure 29D:
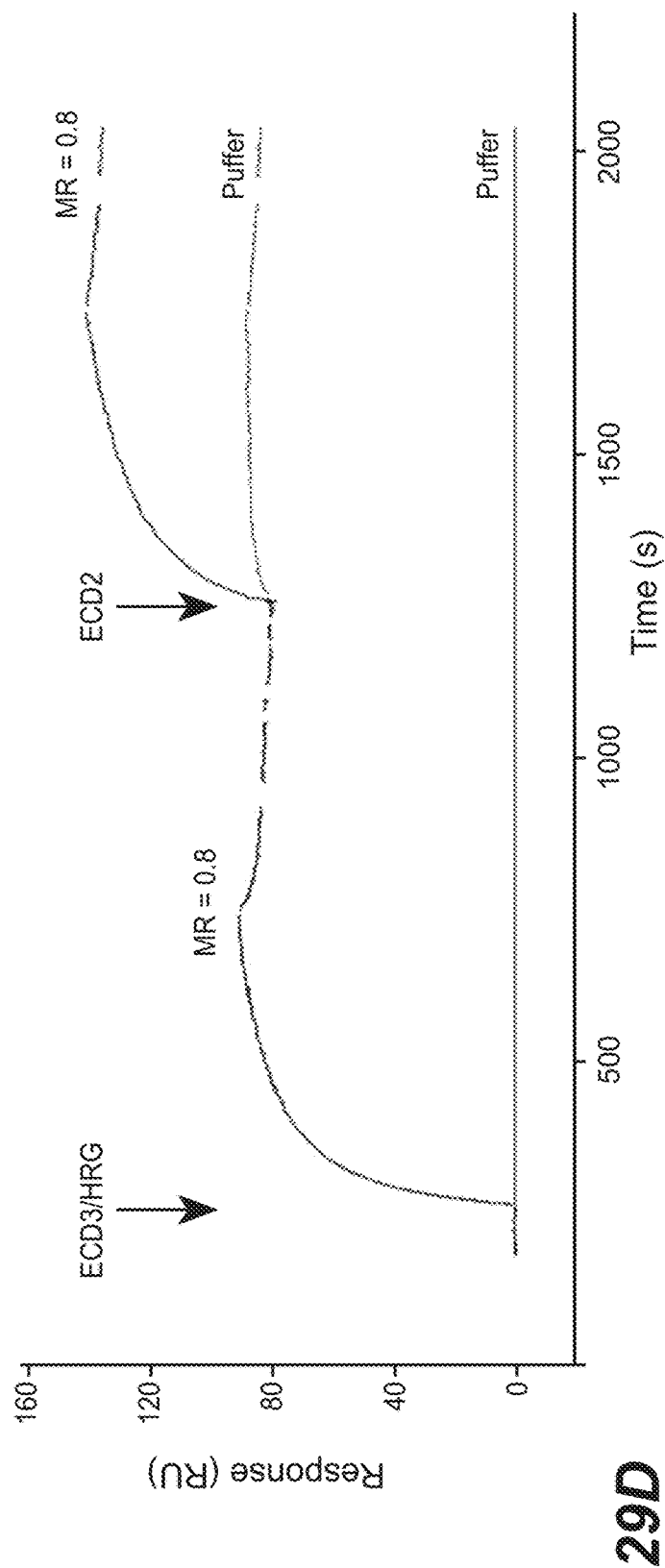

The analytes in solution tested were 270 nM human recombinant HER2-ECD (69.6 kDa) and 270 nM human recombinant HER3-ECD (68 kDa) which was incubated with a 3-fold molar excess of human Heregulin1β (HRG1β) a 44 kDa homodimeric protein, for 60 min at room temperature resulting in HER3-ECD/HRG1β complex. Analytes in solution were injected at different concentration steps of 0 nM, 3.3 nM, 10 nM, 30 nM, 90 nM and 270 nM for 5 min at a flow rate of 30 µl/min (FIG. 28). The dissociation was monitored for 10 min. Kinetic signatures were evaluated, where possible, according to a Langmuir fit.

For assessing the simultaneous binding capacity of DIB×PERT to both HER2-ECD and the HER3-ECD/HRG1β complex, a second assay setup was used. Herein, the analytes HER2-ECD (270 nM) and HER3-ECD/HRG1β complex (270 nM HER3-ECD with a threefold surplus of HRG1β) were injected subsequently, or vice versa (FIG. 29). The association and dissociation rates were monitored for 10 minutes and 8 minutes, respectively.

DIB×PERT Retained the Specificity of the Parental Antibodies

DIB×PERT and the parental antibodies DIB-74 in the monovalent MoAb format and Pertuzumab in the bivalent IgG format, were compared, using SPR analyses. DIB×PERT retained the specificities of its parental antibodies Pertuzumab and DIB-74 and bound to the HER2-ECD as well as the HER3-ECD/HRG1β complex (FIG. 7). The data show, that the affinity of Pertuzumab for the HER2-ECD ($K_D$ 1.7 nM) was retained in DIB×PERT ($K_D$ 1.6 nM). The Molar Ratio of Pertuzumab (MR=1.3) was two-fold higher than of DIB×PERT (MR=0.6 nM). The ability to bind the open HER3-ECD (HER3-ECD/HRG1β) was also retained in DIB×PERT. The affinity of DIB×PERT to the HER3-ECD/HRG1β complex ($K_D$ 3.9 nM) was comparable to that of the DIB-MoAb to the HER3-ECD/HRG1β complex ($K_D$ 2.1 nM). Both antibodies bound with a substoichiometric molar ratio of 0.6 and 0.5, respectively (Table 12).

TABLE 12

Kinetic parameters of DIBxPERT and the parental antibodies DIB-MoAb and Pertuzumab, determined by SPR analyses, using a B3000 Biacore instrument (Ge Healthcare).

| Ligand | Analyte | CL (RU) | $R_{max}$ (RU) | $k_a$ (1/Ms) | $k_d$ (1/s) | $t_{1/2-diss}$ (min) | $K_D$ (nM) | MR |
|---|---|---|---|---|---|---|---|---|
| PERT | HER2-ECD | 160 | 99 | 6.9E+04 | 1.2E−04 | 100 | 1.7 | 1.3 |
| DIBxPERT | HER2-ECD | 165 | 46 | 8.5E+04 | 1.4E−04 | 83 | 1.6 | 0.6 |

TABLE 12-continued

Kinetic parameters of DIBxPERT and the parental antibodies DIB-MoAb and Pertuzumab, determined by SPR analyses, using a B3000 Biacore instrument (Ge Healthcare).

| Ligand | Analyte | CL (RU) | $R_{max}$ (RU) | $k_a$ (1/Ms) | $k_d$ (1/s) | $t_{1/2\text{-}diss}$ (min) | $K_D$ (nM) | MR |
|---|---|---|---|---|---|---|---|---|
| DIB-MoAb | HER3-ECD/HRG1β | 121 | 81 | 1.1E+05 | 2.3E−04 | 51 | 2.1 | 0.6 |
| DIBxPERT | HER3-ECD/HRG1β | 162 | 64 | 8.4E+04 | 3.3E−04 | 35 | 3.9 | 0.5 |

CL: Capture level in Response Units, $R_{max}$: maximal binding level of the analytes, $k_a$: association rate constant in 1/Ms, $k_d$: dissociation rate constant in 1/s, $t_{1/2\text{-}diss}$: complex half-life period in minutes, $K_D$: equilibrium dissociation constant, MR: molar ratio.

Simultaneous Binding of DIBxPERT to Soluble HER2-ECD and HER3-ECD/HRG1β Complex

The simultaneous binding capacity of DIBxPERT to the soluble HER2-ECD and HER3-ECD/HRG1β complex was assessed using SPR analyses (FIG. 29). We found, that DIBxPERT was able to bind the HER3-ECD/HRG1β complex with one valence (MR=0.7), even when already bound to the HER2-ECD with the second valence (MR=0.8). Reciprocal, DIBxPERT bound the HER2-ECD with one valence (MR=0.8), when already bound to the HER3-ECD/HRG1β complex with the second valence (MR=0.8). The data show, that DIBxPERT is able to bind both targets (HER2-ECD and HER3-ECD/HRG1β) at the same time, when using soluble analytes.

Example 17

Figure 30A:
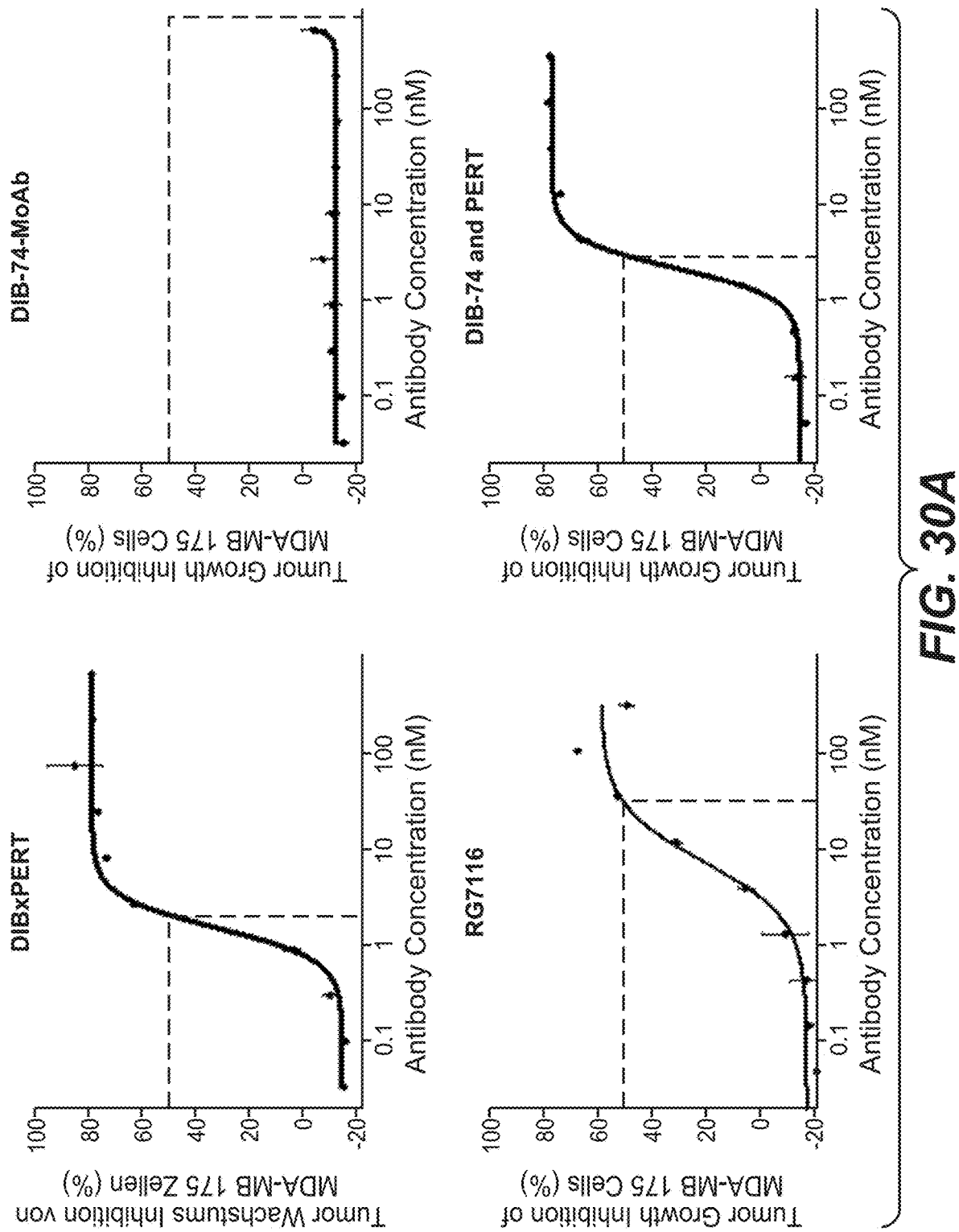
FIGS. 30A-B Growth proliferation inhibition of MDA-MB-175 VII cancer cells by DIBxPERT in comparison to parental antibodies. MDA-MB-175 VII breast cancer cells were incubated for 6 days with a series dilution of either of the following antibodies: DIBxPERT, DIB-MoAb, DIB-74, Pertuzumab (PERT), RG7116, DIB-74 and Pertuzumab, RG7116 and Pertuzumab and an Isotype control. $EC_{50}$ values were calculated using means of triplicates for each antibody concentration. Depicted are normalized four-parameter sigmoidal dose-response curves. Standard deviations are indicated as error bars.
Figure 30B:
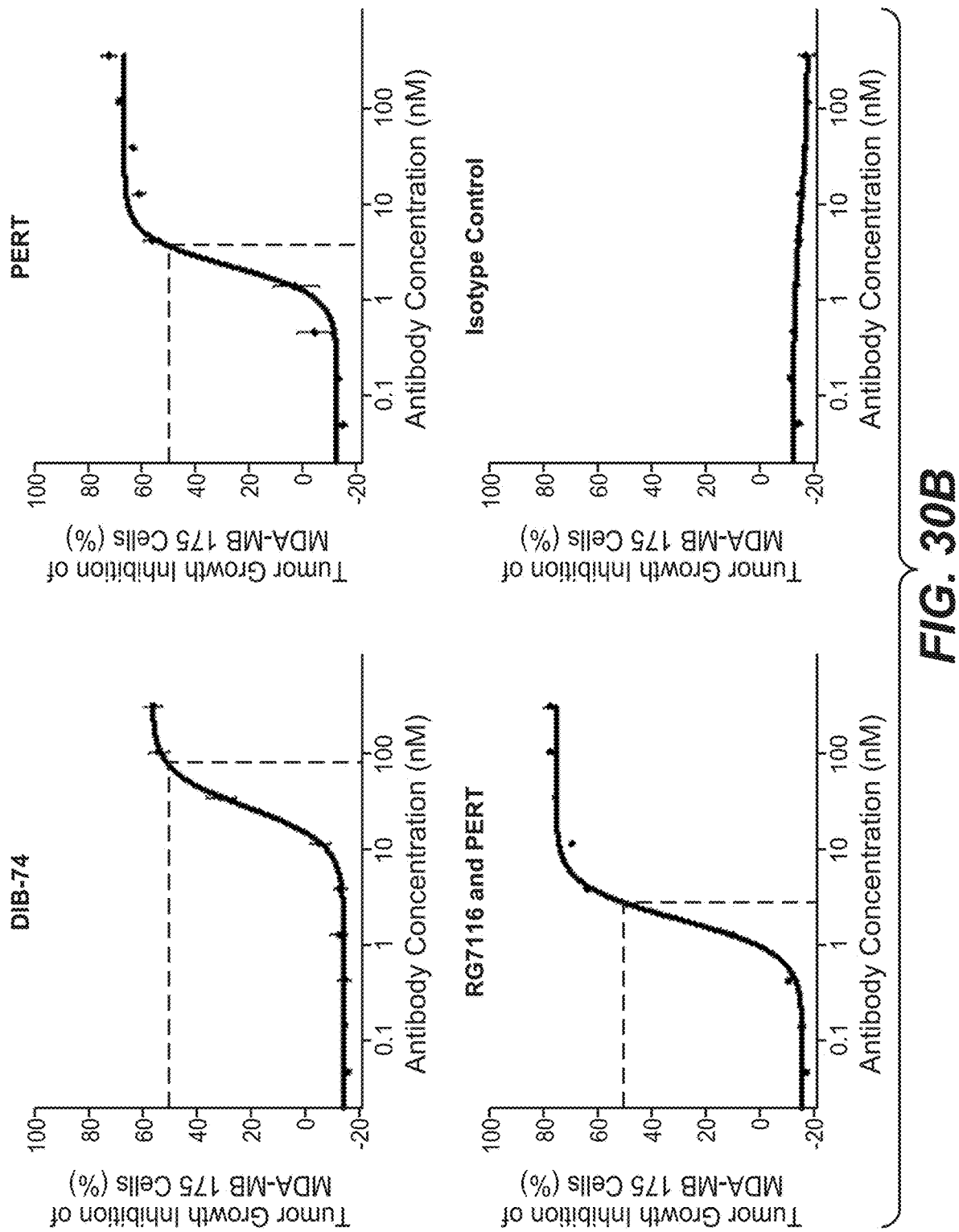

Inhibition of Tumor Cell Proliferation of HER3/HER2 Bispecific Antibody DIBxPERT in MDA-MB-175 VII Cells The anti-tumor efficacy of DIBxPERT was assessed in a cell proliferation assay, using MDA-MB-175 cells (VII Human Breast Carcinoma Cells, ATCC catalog no. HTB-25). 20,000 cells per well were seeded into sterile 96 well tissue culture plates with DMEM/F12 cell culture medium, containing 10% FCS and 2 mM L-Glutamine and incubated at 37° C. with 5% $CO_2$ for one day. The cells are slow growing cells with a doubling time of approximately 3 days. Cells were starved with 0.5% FCS containing DMEM/F12 cell culture medium, containing 2 mM L-Glutamine. DIBxPERT and control antibodies were added in dilution series and further incubated for 6 days. The applied antibodies are listed in table 13. Cell viability was then assessed using the alamarBlue® readout. $EC_{50}$ values were calculated using means of triplicates for each antibody concentration (FIG. 30).

TABLE 13

Antibodies used for the inhibition of tumor cell proliferation in MDA-MB-175 VII cells in vitro.
Additionally to the below mentioned single treatments, the combination treatments of DIB-74 with Pertuzumab and RG7116 with Pertuzumab were applied in vitro.

| Antibody | Format | Valence | Specificity |
|---|---|---|---|
| DIBxPERT | CrossMab | bivalent | anti-HER2 subdomain II anti-HER3 β-hairpin |
| DIB-MoAb (monovalent antibody based on M-05-74) | MoAb | monovalent | anti-HER3 β-hairpin |
| DIB-74 (M-05-74) | Monoclonal IgG | bivalent | anti-HER3 β-hairpin |
| Pertuzumab | Monoclonal IgG | bivalent | anti-HER2 subdomain II |
| RG7116 (<HER3> Mab binding to domain I) | Monoclonal IgG | bivalent | anti-HER3 subdomain I |
| Isotype control | Polyclonal IgG | bivalent | no specific target |

Inhibition of Tumor Cell Proliferation of DIBxPERT in MDA-MB-175 VII Cells

The inhibition of tumor cell proliferation of DIBxPERT was examined in vitro, using MDA-MB-175 VII cells. In the MDA-MB-175 VII cell line (doubling time 3 days) the oncogenic signal arises from an autocrine HRG growth loop. Cells were incubated with the series diluted antibodies DIBxPERT, DIB-MoAb, DIB-74, Pertuzumab, RG7116, the combinations of DIB-74 and Pertuzumab and of RG7116 and Pertuzumab and an Isotype control (FIG. 30). After 6 days, the maximal growth inhibition of 79% was achieved by DIBxPERT, in contrast to the other mono and combination treatments (Table 14). The second highest maximum inhibitory effect was seen with the combinations of DIB-74 and Pertuzumab (76%) and RG7116 and Pertuzumab (76%) treated cells. The $EC_{50}$ for DIBxPERT-mediated growth inhibition was 1 nM and thereby superior to the $EC_{50}$ of control antibodies. Pertuzumab mono-treatment or Pertuzumab in combination with DIB-74 or RG7116 showed growth inhibition $EC_{50}$ of 2 nM. Compared to that, RG7116 ($EC_{50}$ 7 nM) and DIB ($EC_{50}$ 26 nM) alone mediated a lower tumor growth inhibition in vitro.

TABLE 14

Inhibition of tumor cell proliferation of DIBxPERT in MDA-MB-175 VII cells.

| Antibody | Tumor cell proliferation inhibition (%) | | EC50 (nM) |
|---|---|---|---|
| | minimum | maximum | |
| DIBxPERT | −14 | 79 | 1 |
| DIB-MoAb monovalent M-05-74 | −12 | n/a | n/a |

TABLE 14-continued

Inhibition of tumor cell proliferation of DIBxPERT in MDA-MB-175 VII cells.

| Antibody | Tumor cell proliferation inhibition (%) | | EC50 (nM) |
|---|---|---|---|
| | minimum | maximum | |
| DIB (M-05-74) | −15 | 56 | 26 |
| PERT | −12 | 67 | 2 |
| RG7116 | −17 | 58 | 7 |
| Combination of DIB and PERT | −15 | 76 | 2 |
| Combination RG7116 and PERT | −16 | 76 | 2 |
| Isotype control | −19 | −13 | n/a |

DIB: murine DIB-74 IgG;
PERT: Pertuzumab IgG;
RG7116: humanized anti-HER3 subdomain I IgG;
Isotype control: polyclonal human antibody;
n/a: not applicable.

The invention claimed is:

1. An isolated bispecific antibody which binds to human HER3 and to human HER2, wherein the antibody binds to an epitope of human HER3 within the amino acid sequence of PQPLVYNKLTFQLEPNPHT (SEQ ID NO:1) which is comprised in the polypeptide of SEQ ID NO: 18 and binds to domain II of human HER2 comprising the amino acid sequence of SEQ ID NO: 59.

2. The bispecific antibody according to claim 1, wherein the bispecific antibody is bivalent.

3. An isolated nucleic acid encoding the bispecific antibody according to claim 1.

4. A host cell comprising the nucleic acid of claim 3.

5. A method of producing a bispecific antibody according to claim 3, said method comprising culturing the host cell of claim 4 so that the antibody is produced.

6. A pharmaceutical formulation comprising the bispecific antibody according to claim 1 and a pharmaceutically acceptable carrier.

* * * * *